(12) United States Patent
Cink et al.

(10) Patent No.: US 10,085,435 B2
(45) Date of Patent: Oct. 2, 2018

(54) PEST CONTROL AND DETECTION SYSTEM WITH CONDUCTIVE BAIT MATRIX

(71) Applicant: BASF CORPORATION, Florham Park, NJ (US)

(72) Inventors: James H. Cink, Wake Forest, NC (US); Greggory K. Storey, Cary, NC (US); Kyle K. Jordan, Durham, NC (US); James W. Austin, Wake Forest, NC (US); Charles E. Evanhoe, Dayton, OH (US); Bart Ivy, Prattville, AL (US); Daniel W. Engels, Colleyville, TX (US); Daniel Freeman, Springfield, OH (US); Kenneth Lauffenburger, Dallas, TX (US); Thomas Dills, Warners Robins, GA (US); Kenneth S. Brown, Apex, NC (US); Cheryl Leichter, Durham, NC (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/523,312

(22) PCT Filed: Jul. 13, 2016

(86) PCT No.: PCT/US2016/042126
§ 371 (c)(1),
(2) Date: Apr. 28, 2017

(87) PCT Pub. No.: WO2017/011574
PCT Pub. Date: Jan. 19, 2017

(65) Prior Publication Data
US 2018/0132468 A1    May 17, 2018

Related U.S. Application Data

(60) Provisional application No. 62/191,830, filed on Jul. 13, 2015, provisional application No. 62/191,857, (Continued)

(51) Int. Cl.
*A01M 1/02* (2006.01)
*A01N 25/10* (2006.01)
*A01M 1/20* (2006.01)

(52) U.S. Cl.
CPC .......... *A01M 1/026* (2013.01); *A01M 1/2011* (2013.01); *A01N 25/10* (2013.01)

(58) Field of Classification Search
CPC .......... A01M 1/00; A01M 1/02; A01M 1/026; A01M 1/2005; H01B 1/20
See application file for complete search history.

(56) References Cited

U.S. PATENT DOCUMENTS 5,815,090 A * 9/1998 Su .................. A01M 1/026
340/870.16
6,166,641 A * 12/2000 Oguchi .......... A01M 1/026
340/573.1
(Continued)

FOREIGN PATENT DOCUMENTS

EP    965615 B1    11/2002
EP    937120 B1    9/2004
(Continued)

OTHER PUBLICATIONS

International Search Report issued in International Application No. PCT/US2016/042126 dated Nov. 1, 2016, 3 pages.
(Continued)

*Primary Examiner* — Mark Kopec
(74) *Attorney, Agent, or Firm* — Armstrong Teasdale LLP

(57) ABSTRACT

A pest control and detection system generally includes an electrically conductive bait matrix including at least one
(Continued)

carrier material that is at least one of palatable, a phagostimulant, consumable, and displaceable by pests, and a plurality of electrically conductive particles. The electrically conductive particles are substantially randomly interspersed throughout the at least one carrier material. The at least one carrier material includes at least one of a thermoplastic material and a resin.

6 Claims, 28 Drawing Sheets

Related U.S. Application Data filed on Jul. 13, 2015, provisional application No. 62/270,747, filed on Dec. 22, 2015.

(56) References Cited

U.S. PATENT DOCUMENTS

| | | | |
|---|---|---|---|
| 6,304,185 B1* | 10/2001 | Tuttle | A01M 1/026 340/10.1 |
| 2009/0288335 A1 | 11/2009 | Cink | |
| 2010/0043276 A1* | 2/2010 | Eger, Jr. | A01M 1/026 43/131 |
| 2013/0276354 A1 | 10/2013 | Eger, Jr. et al. | |
| 2015/0305326 A1 | 10/2015 | Hill et al. | |
| 2016/0135443 A1* | 5/2016 | Donaldson | A01M 29/28 43/98 |
| 2016/0219858 A1* | 8/2016 | Cink | A01M 1/026 |

FOREIGN PATENT DOCUMENTS

| | | |
|---|---|---|
| EP | 947559 B1 | 10/2004 |
| EP | 950689 B1 | 10/2004 |
| EP | 1656423 B1 | 4/2008 |
| EP | 1838784 B1 | 6/2008 |
| WO | 1992009654 A2 | 6/1992 |
| WO | 1994014870 A1 | 7/1994 |
| WO | 1996015173 A1 | 5/1996 |
| WO | 1996015174 A1 | 5/1996 |
| WO | 1996015175 A1 | 5/1996 |
| WO | 1996015176 A1 | 5/1996 |
| WO | 1996021689 A2 | 7/1996 |
| WO | 1996021690 A1 | 7/1996 |
| WO | 1996021691 A1 | 7/1996 |
| WO | 1996025446 A1 | 8/1996 |
| WO | 1996025448 A1 | 8/1996 |
| WO | 1998012242 A1 | 3/1998 |
| WO | 2009127556 A1 | 10/2009 |
| WO | 2015036934 A1 | 3/2015 |

OTHER PUBLICATIONS

Written Opinion of the International Searching Authority issued in International Application No. PCT/US2016/042126 dated Nov. 1, 2016, 3 pages.

* cited by examiner

PEST CONTROL AND DETECTION SYSTEM WITH CONDUCTIVE BAIT MATRIX

CROSS REFERENCE TO RELATED APPLICATIONS

The present patent document claims the benefit of the filing date under 35 U.S.C. § 119(e) of Provisional U.S. Patent Application Ser. Nos. 62/191,830, filed Jul. 13, 2015, 62/191,857 filed Jul. 13, 2015, and 62/270,747, filed Dec. 22, 2015, which are hereby incorporated by reference in their entirety.

BACKGROUND

The present invention relates generally to a pest control and/or detection system and, more particularly, to a pest control and/or detection system with remote monitoring capability.

Pests can cause damage to raw materials, structures, crops, food, livestock, and other human concerns. Conventional pest control apparatuses often facilitate locating, detecting, deterring, and/or eradicating pests by deploying an attractant (or bait) that the pests are inclined to chew for purposes of collection and/or consumption.

Many conventional pest control apparatuses must be physically inspected (e.g., manually disassembled) to visually determine whether pests are present, and to what extent, the pests are chewing (or otherwise depleting) the bait. For example, in current termite monitoring and control systems, a bait matrix (or matrices) is typically inserted into a physical station housing that is itself inserted into a cavity in the ground. During foraging, termites searching for food encounter the stations, enter the interior of the station housings and begin feeding on the consumable bait matrix or matrices. The bait typically consists of non-toxic materials, or alternatively a mixture of non-toxic and toxic materials (i.e., a pesticide active ingredient).

To determine if termites are present in the stations and actively feeding on the bait matrix, a technician generally must open the station and in some instances remove and visually inspect the bait matrix. Prior to opening the station, the technician is unaware of and to what extent feeding has occurred. Such an inspection process can be time-consuming for the technician, and can be disruptive to the site at which the stations are deployed. In some instances, this disruption can cause termites to leave the station before a toxic material can be placed within the station. Some weaknesses of the existing pest control apparatuses or systems may include, but are not limited to, false indication of the presence or absence of pests, higher labor costs, need for expensive detection equipment, poor reliability, use of cumbersome equipment, incompatibility with other technologies, and incomplete information for service providers.

There is a need, therefore, for a pest control and/or detection system which accurately and effectively allows the bait matrix of a station to be monitored from the exterior of the station, and in particular from a location remote from the site of the station. Greater reliability and/or accuracy, decreased costs (including but not limited to labor and/or energy), objective more consistent monitoring, continual monitoring combined with an option for constant access, increased eco-friendliness by limiting the presence of toxicants in the environment, automated data collection and analysis, proactive monitoring and flexible treatment options when pests are detected. In addition, it is advantageous to have a pest control and/or detection system that does not require the actual consumption of the bait matrix but is effective based on either the displacement of the bait matrix and/or the consumption of the bait matrix.

SUMMARY

In one embodiment, a pest control and/or detection system generally comprises an electrically conductive bait matrix comprising at least one carrier material that is at least one of palatable, acts as a phagostimulant and/or consumable and/or displaceable by pests, and a plurality of electrically conductive particles. The electrically conductive particles are substantially randomly interspersed throughout at least one carrier material. The at least one carrier material comprises a thermoplastic material and/or a resin.

In one preferred embodiment, the thermoplastic material is or comprises a thermoplastic polyester.

In another embodiment, a pest control and/or detection system generally comprises a magnetically conductive bait matrix comprising at least one carrier material that is, at least one of, palatable, phagostimulant and/or consumable and/or displaceable by pests, and a plurality of magnetically conductive particles. The magnetically conductive particles may be substantially randomly interspersed throughout the at least one carrier material. The at least one carrier material comprises a thermoplastic material and/or a resin.

In one preferred embodiment, the thermoplastic material is or comprises a thermoplastic polyester.

In another aspect, a pest control and/or detection system generally comprises an electrically conductive bait matrix comprising at least one carrier material that is at least one of palatable, phagostimulant and/or consumable and/or displaceable by pests, and a plurality of electrically conductive particles that may also be consumable or displaceable by pests. It may be preferred that at least a portion of the bait matrix 124 be electrically conductive. The electrically conductive particles are substantially randomly interspersed throughout the at least one carrier material. The bait matrix may have a first end and a second end. A first electrode is in electrically conductive contact with the bait matrix at the first end thereof, and a second electrode is in electrically conductive contact with the bait matrix at the second end thereof, with the bait matrix, the first electrode and the second electrode being held in assembly. A biasing member may be used to urge the first electrode against the first end of the bait matrix and further urges the second electrode against the second end of the bait matrix. It is to be understood that the first end and second end may be on the top, bottom and/or sides of the bait matrix, or any other such configuration so long as a conductive portion of the bait matrix is located between the electrodes or electrical plates. It is to be understood that a bait matrix or matrices as used herein may comprise a palatable material(s) that is consumable and/or displaceable and which typically consists of non-toxic materials, or alternatively a mixture of non-toxic and toxic materials (i.e., a pesticide active ingredient). It is to be further understood that the bait matrix may or may not be digestible.

In yet another aspect, the pest control and/or detection system generally comprises an electrically conductive bait matrix comprising at least one carrier material that is at least one of palatable, phagostimulant and/or consumable and/or displaceable by pests, and a plurality of electrically conductive particles. The electrically conductive particles are substantially randomly interspersed throughout the at least one carrier material. A control unit is held in assembly with the bait matrix and is operable to energize the bait matrix. The control unit is further operable to transmit signals indicative of at least one characteristic of the bait matrix. An environmental sensor is operable to sense at least one environmental characteristic of an environment in which the bait matrix is located. It is to be understood that the term conductive as used herein means a material having the ability to conduct a current, electrical or otherwise. Conductivity is a quantifiable property of a material or component and the level of change in conductivity is a measurable characteristic of a material or component. It is to be further understood that another measurable characteristic of a material is the level of resistivity in a material. The term resistivity as used herein means how strongly a given material opposes the flow of a current. The resistance of a component, such as the bait matrix, is a measurable characteristic as well. Resistance as used herein means the degree to which a substance or device opposes the passage of a current, electrical or otherwise. This may be calculated using Ohm's law.

Yet another aspect, of the pest control and/or detection system generally comprises an electrically conductive bait matrix comprising at least one carrier material that is at least one of palatable, phagostimulant and/or consumable and/or displaceable by pests, and a plurality of electrically conductive particles as well as a non-conductive bait matrix comprising at least one carrier material that is at least one of palatable, phagostimulant and/or consumable and/or displaceable by pests. The electrically conductive particles are substantially randomly interspersed throughout the at least one carrier material and a pair of electrodes are positioned at opposite ends or opposing sides of the conductive bait matrix. A control unit is held in assembly with the bait matrix and may be operable to energize the bait matrix. The control unit is further operable to transmit signals indicative of at least one characteristic of the bait matrix. An environmental sensor may be operable to sense at least one environmental characteristic of an environment in which the bait matrix is located.

DETAILED DESCRIPTION

Figure 1:
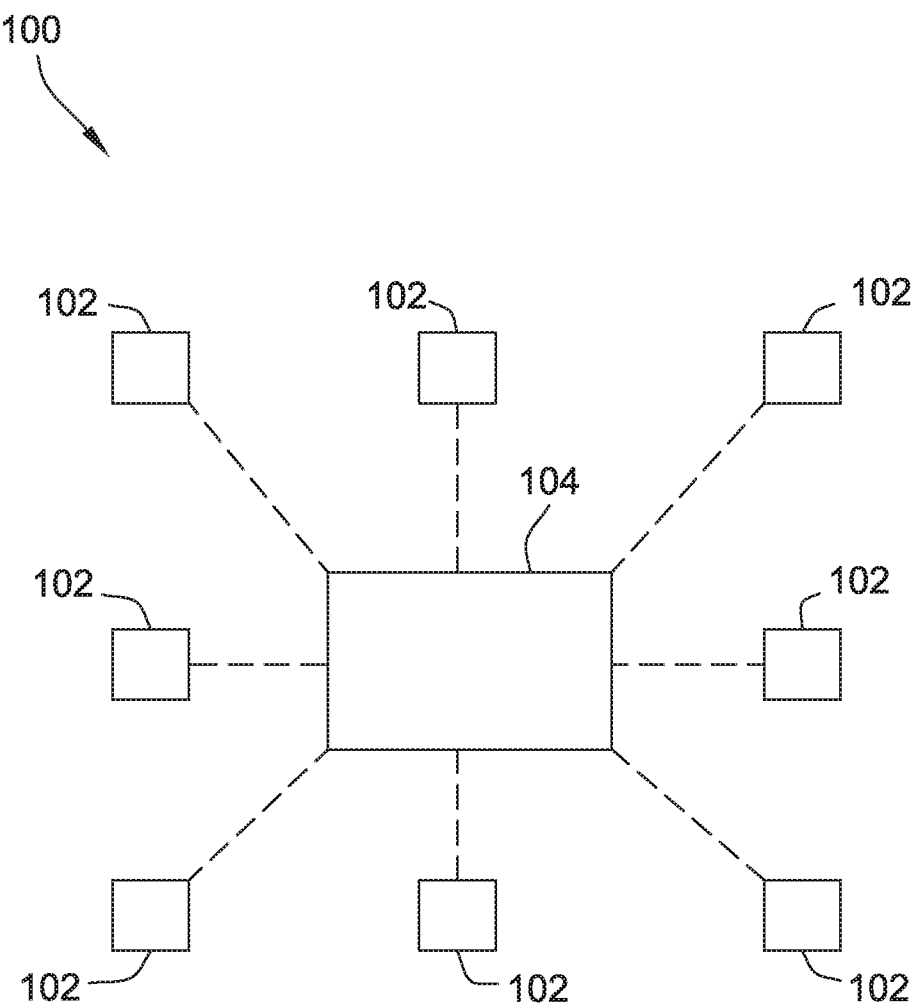
FIG. 1 is a schematic illustration of one embodiment of a pest control and/or detection system.

Referring now to the drawings, and in particular to FIG. 1, a pest control and/or detection system according to one embodiment is generally indicated by reference numeral 100. In the illustrated embodiment, the system 100 is configured for at least monitoring and/or detecting, and in some embodiments controlling, termites. In other contemplated embodiments, however, the system 100 may be configured for remotely monitoring and/or detecting, and in some embodiments controlling, other pests such as, for example and without limitation, cockroaches, ants or other insects, rats, mice, voles or other rodents, birds, bats, etc.

The illustrated pest control and/or detection system 100 includes at least one bait station 102 and at least one data collection system 104 capable of communicating with the bait station(s) 102 by receiving signals from and/or in some embodiments for transmitting signals to, the bait station(s) 102 as set forth in more detail below. Suitably, the at least one data collection system 104 may include a processor-based or microprocessor-based device with associated memory (such as a computer or a microcontroller); or any suitable configuration of a reduced instruction set circuit(s) (RISC), an application-specific integrated circuit(s) (ASICs), and/or a logic circuit(s). Alternatively, the at least one data collection system 104 may suitably include any circuit and/or processor that is capable of executing the functions of the at least one data collection system 104 as described herein. As used herein, the term "signal" is not limited to a particular type of signaling methodology but, rather, broadly refers to any suitable type of wireless signaling, for example, WiFi or cellular. It is to be understood that a plurality of collection systems 104 may be employed. It is also to be understood that the at least one data collection system 104 may also function as a bait station 102.

For example, in one contemplated embodiment, the pest control and/or detection system 100 may include a plurality of bait stations 102 deployed at a site for monitoring and/or detecting pest activity (e.g., the perimeter around a home), and the at least one data collection system 104 may be located remote from and stationary relative to the site and may communicate with the bait stations 102 from the remote location as set forth in more detail below. Alternatively, the data collection system 104 may be configured for use at the site (e.g., the at least one data collection system 104 may be readable by a suitable handheld device that is moveable relative to the data collection system 104).

Figure 2:
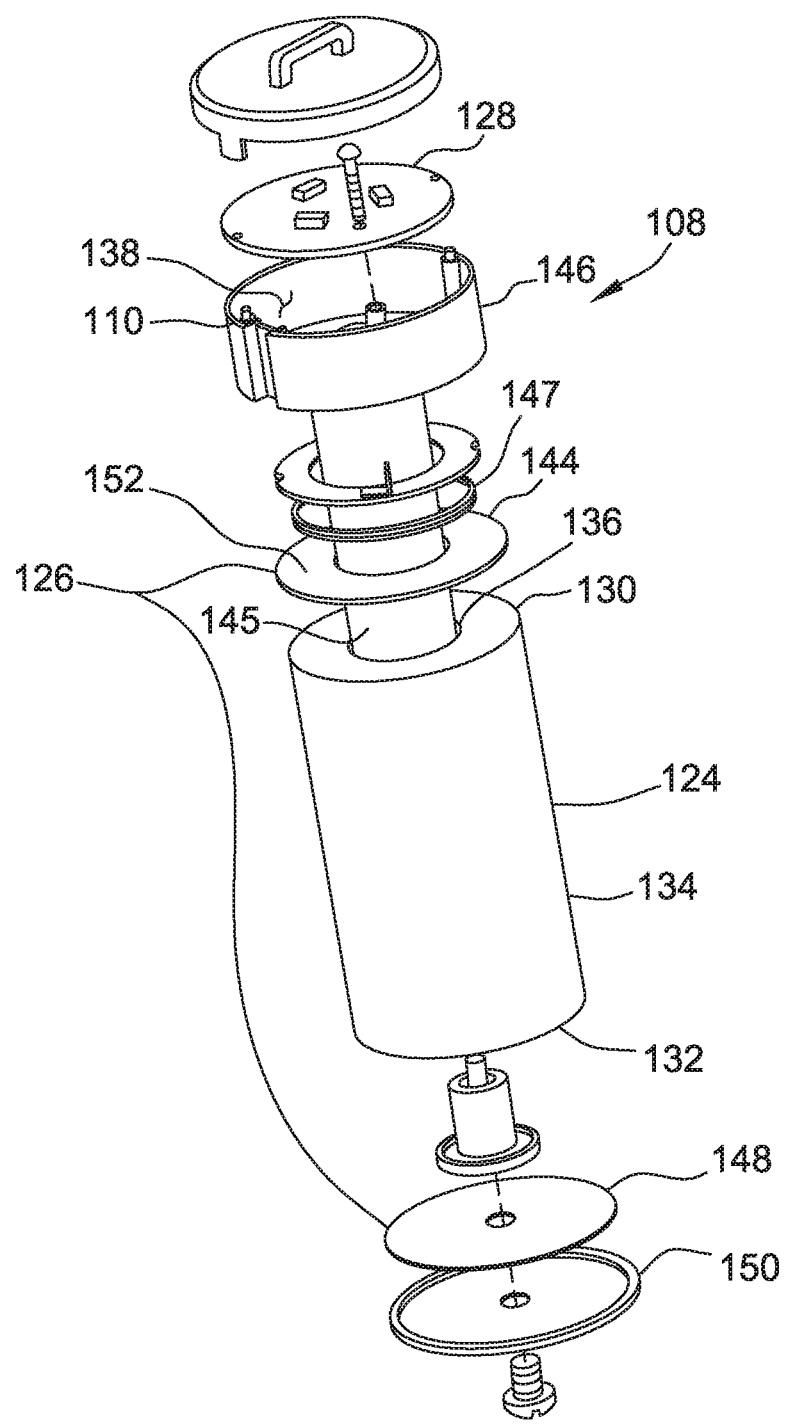
FIG. 2 is an exploded view of a bait station 102 of the pest control and/or detection system of FIG. 1.
Figure 3:
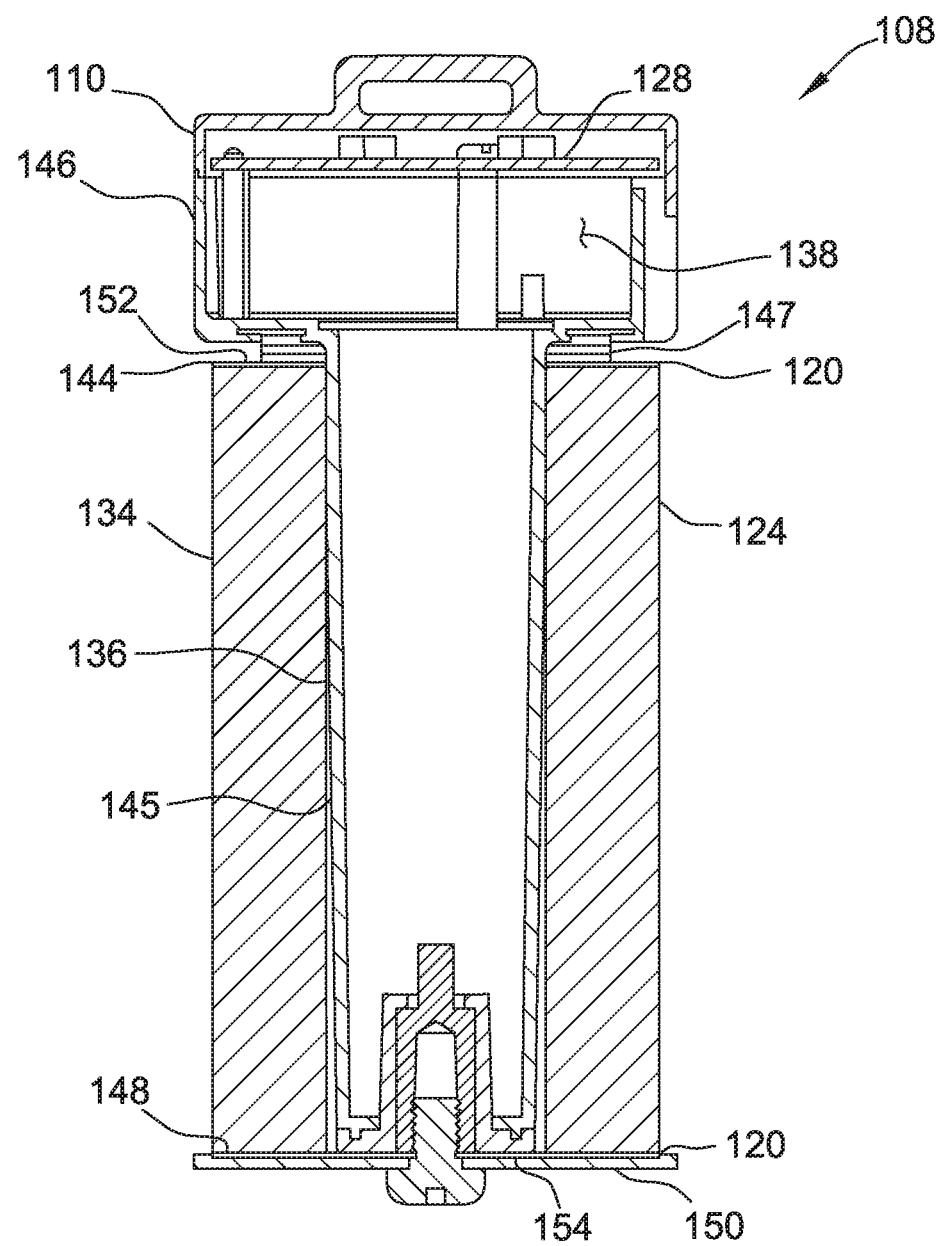
FIG. 3 is a longitudinal cross-section of the bait station of FIG. 2.

Referring to FIGS. 2 and 3, each bait station 102 includes a sensor assembly (indicated generally by reference numeral 108) and, optionally, a suitable station housing (not shown) for enclosing and/or housing the sensor assembly 108 at the placement location (e.g. in the ground) and permitting the ingress and egress of termites into and out of the station housing (e.g., via slits or holes in the station housing) and thereby enabling the termites to feed on the bait matrix 124 comprised with the sensor assembly 108 as set forth in more detail below. It is to be understood that a station housing is not required for bait station 102 and/or for data collection system 104.

The illustrated sensor assembly 108 generally comprises a sensor holder 110, a bait matrix 124, an electrode assembly 126, and a control unit 128. As set forth in more detail below, the electrode assembly 126 is electrically connected to the bait matrix 124, and the control unit 128 is configured for selectively supplying the bait matrix 124 with electrical current via the electrode assembly 126. In particular embodiments, the control unit 128 is also operable to transmit a signal indicative of at least one characteristic of the bait matrix 124 as a function of electrical current being supplied to the bait matrix 124. In this manner, the control unit 128 facilitates remote monitoring by the data collection system 104, which is capable of receiving the signals transmitted by the control unit 128.

The illustrated bait matrix 124 is preferably tubular (e.g., generally cylindrical in the illustrated embodiment) having a first end surface 130, a second end surface 132, a circumferential outer surface 134, and a circumferential inner surface 136 defining an internal cavity of the bait matrix. It is understood, however, that the bait matrix 124 may be of other suitable shapes. For example, the bait matrix 124 may have a tubular shape that is not generally cylindrical (e.g., the tubular shape may have a substantially polygonal cross-section), and/or the cavity may not extend from the first end surface 130 to the second end surface 132. Alternatively, the bait matrix 124 may not be tubular but, rather, may be generally shaped like a sphere, pyramid, cube, square, star or any other suitable shape.

It is also understood that the thickness (i.e., the transverse width from the outer surface 134 to the inner surface 136) of the tubular bait matrix 124 shown in the Figs. is for illustration purposes. The thickness of the bait matrix 124 according to one particularly suitable embodiment is substantially greater than that illustrated in the Figs. The thickness of the bait matrix 124, however, may be any suitable thickness without departing from the scope of this invention.

Figure 11:
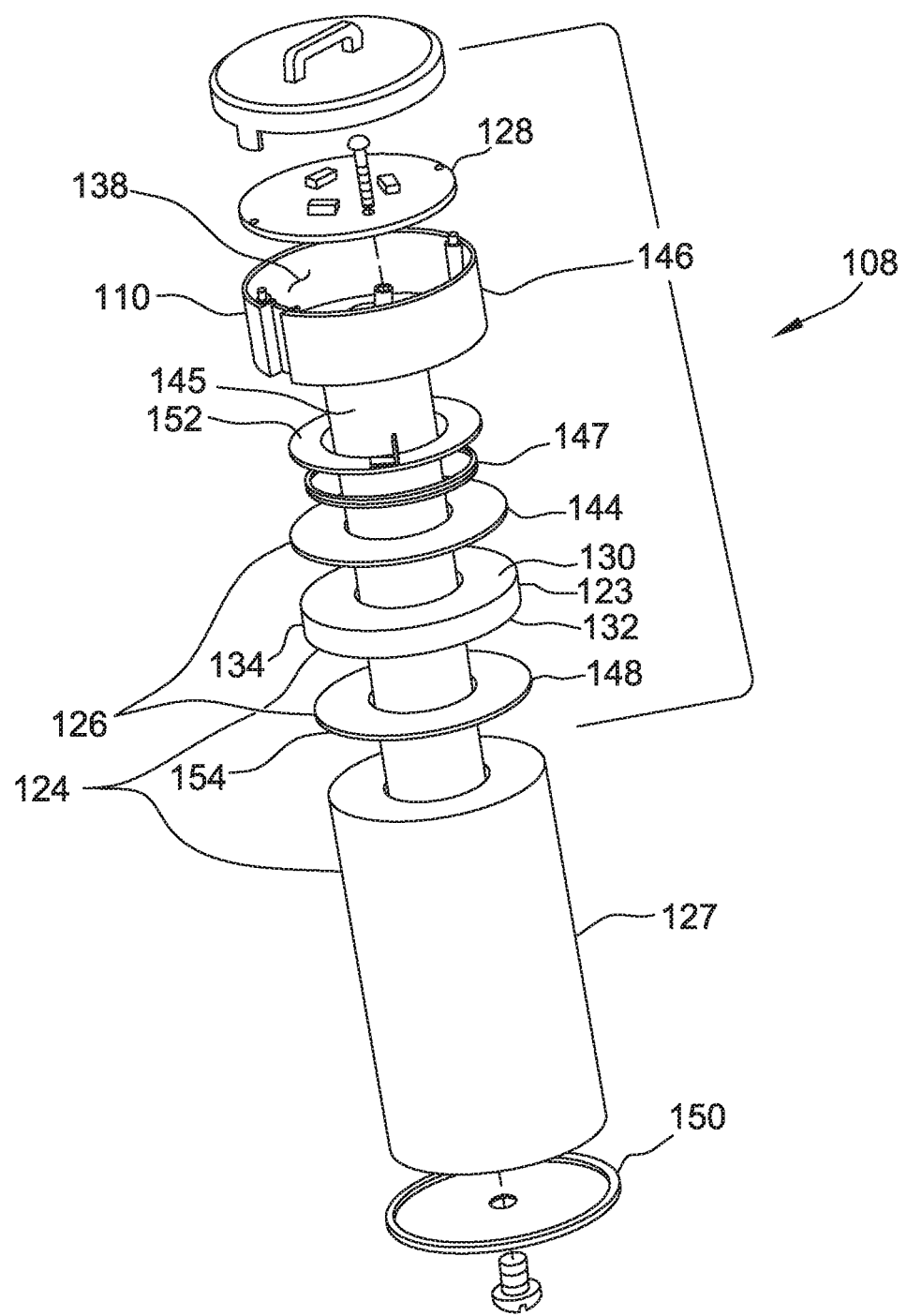
FIG. 11 is an exploded view of a bait station 102 of the pest control and/or detection system of FIG. 1 comprising a conductive bait matrix as well as a non-conductive bait matrix.
Figure 12:
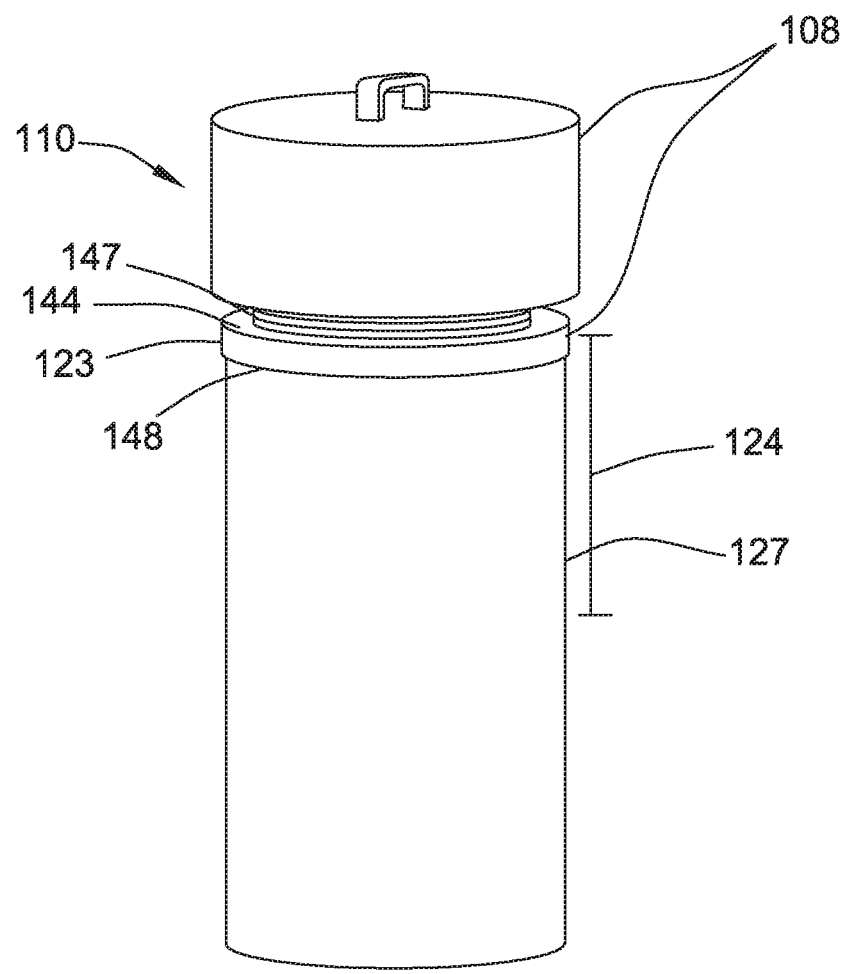
FIG. 12 is a view of a bait station of the pest control and/or detection system of FIG. 1 comprising a conductive bait matrix as well as a non-conductive bait matrix.

The bait matrix 124 may be conductive. It may be preferred that the bait matrix 124 may include one or more sections wherein at least one section may comprise a conductive bait matrix 123 and a second section may comprise a non-conductive bait matrix 127 as shown in FIGS. 11 and 12. The one or more sections of the bait matrix 124 comprising the conductive bait matrix 123 may have at least two electrical contacts such as electrical plates, gels, electrodes, caulks, grease, or the like 144, 148 at opposing locations of the conductive bait matrix 123 relative to each other in order to generate a current through the conductive bait matrix 123. It is to be understood that these terms electrical contacts, electrodes, electrical plates etc. . . . may be used interchangeably throughout this application to mean the group of potential electrical contacts as a whole and as illustrated by 144/148 in the Figures. It is also to be understood that if the conductive current is chosen to not be electrical in nature other forms of contacts may be used to make the bait conductive in nature.

The conductive bait matrix 123 may comprise up to 5% of the size of the total bait matrix 124 (conductive portion 123 plus the non-conductive portion 127), up to 10% of the total bait matrix, up to 15% total bait matrix 124, up to 30% of the total bait matrix 124, up to 50% of the total bait matrix 124, up to 75% of the total bait matrix 124, and/or up to 100% of the total bait matrix 124. It may be preferable to have a smaller percentage of the bait matrix 124, such as less than 10% of the size of the entire bait matrix 124 (conductive portion 123 plus non-conductive portion 127), as the conductive bait matrix 123 of the bait matrix 124 to allow for greater accuracy and sensitivity to the detection of pests when the conductive bait is displaced and/or consumed.

The benefit of having the non-conductive bait matrix 127 is to keep the pests in the location of the bait station 102 and encourage recruitment and removal of the conductive bait matrix 123. The conductive bait matrix 123 may be preferred for consumption or displacement by the pests as shown in Table 2 below and as set forth in more detail in Example 1 herein.

In addition it has been found that a larger cellulosic resource will recruit more termites proportionally to that larger resource. (Glenn et al. 2008 and Su et al. 2001). This will accordingly increase the monitor and/or detection systems ability to accurately, quickly and more effectively detect the presence of pests. Subterranean termites have been demonstrated to prefer cellulose materials of a particular dimension (Lenz et al. 2009) and diameter (Waller 2007).

The bait matrix 124 according to one embodiment is of a generally solid construction. In other embodiments the bait matrix 124 may instead be semi-solid (e.g., in the form of a gel), or it may be generally in a liquid state (e.g., in the form of a fluid suspension). In a particularly suitable embodiment, the bait matrix 124 is an extruded bait matrix.

The bait matrix 124 and/or the conductive bait matrix 123 according to one suitable embodiment comprises a carrier material and a plurality of electrically conductive particles. It is to be understood that the non-conductive bait matrix 127 may not contain sufficient conductive particles to carry an electrical charge and/or may not have electrical contacts 144, 148 located at opposing sides of the non-conductive bait matrix. It is also to be understood that the conductive bait matrix 123 may be only a portion (conductive portion 123) of the bait matrix 124 or the entire bait matrix 124. The electrically conductive particles according to one embodiment may be metal particles such as, without limitation, iron, zinc, magnesium, copper or aluminum. The particles may be in any suitable particulate form such as dust, oxide, filings, slag, flakes or other suitable particle form. In other embodiments, the electrically conductive particles are semi-metal or non-metal electrically conductive particles. Suitable examples according to one embodiment include carbon-based particles such as, without limitation, graphite, carbon nanotube fragments, carbon black, coke and carbonized-charcoal powder.

In one particularly suitable embodiment, the electrically conductive particles are particles of graphite. Graphite is available in different types such as e.g. flake graphite, amorphous graphite, vein graphite, expandable graphite, or highly oriented pyrolytic graphite (HOPG).

Graphite is commercially available in a variety of grades for different applications such as EDM Grades (as e.g. described in "Properties and Characteristics of Graphite, For the EDM Industry", Fifth Printing—February 2002, 1987 Poco Graphite, Inc., POCO Graphite, Inc. 300 Old Greenwood Rd. Decatur, Tex. 76234), Industrial Grades (as e.g. described in "Industrial Material Solutions", Poco Graphite Inc., brochures IND-92480-0514, 6204-7085INK-0414, all 2014) Semiconductor Grades, Ion Implant Grades, Biomedical Grades (as e.g. described in "Biomedical Grade Graphites", Poco Graphite Inc., Brochure IND-7334-0514), and Glassmate Grades (as e.g. described in "Glassmate", Poco Graphite Inc., brochure GLA 102930-0214, 2014).

It is well known that different types and grades of graphite differ in one or more of their properties like e.g. density, Shore hardness, Rockwell Hardness, flexural strength, thermal expansion, thermal conductivity, heat capacity, emissivity, compressive strength, electrical resistivity, or average particle size.

In general, any kind and any grade of graphite may be used for the purpose of the invention, provided that its incorporation into the bait matrix facilitates an electrical conductivity of the bait matrix. In a preferred embodiment of the invention, the material comprising electrically conductive particles is graphite provided by graphite manufacturers like e.g. Asbury Graphite Mills, Inc., as conductive filler for the manufacture of electrically conductive polymers. In one embodiment the material comprising conductive particles is ultra fine graphite and/or ultra high surface area graphite.

In one embodiment of the invention, the graphite mean particle size may measure from 1 μm to 20 μm, 1 μm to 15 μm, 1 μm to 10 μm, 1 μm to 5 μm, 1 μm to 3 μm. Methods to determine the average particle size are well known to the person skilled in the art. In one embodiment of the invention the graphite has a surface area in the range from 1 $m^2/g$ to 500 $m^2/g$, from 20 $m^2/g$ to 400 $m^2/g$, from 50 $m^2/g$ to 300 $m^2/g$.

Electrical resistivity (also known as resistivity, specific electrical resistance, or volume resistivity) is an intrinsic property that quantifies how strongly a given material opposes the flow of electric current. The skilled person is familiar with methods to measure electrical resistivity. For example one standard method of measuring the electrical resistivity of a graphite sample is described in ASTM C611-98. In one embodiment of the invention, the electrical resistivity of the material comprising conductive particles, preferably graphite, is at least 0.01 Ω*cm, at least 0.05 Ω*cm, at least 0.1 Ω*cm and up to 1 Ω*cm, up to 0.5 Ω*cm, up to 0.3 Ω*cm.

TABLE 1

Graphite types provided by Asbury Graphite Mills Inc. for the manufacture of conductive polymers
Asbury ® Ultra Fine/Ultra High Surface Area Graphite

| Grade | Type | Mean Particle Size (μm) | Surface Area (m²/gram) | Resistivity (Ohm*cm) |
|---|---|---|---|---|
| 4118 | Synthetic | <3.0 | 100-150 | 0.14 |
| 3725 | Natural | <2.5 | Nominal 180 | 0.23 |
| 2299 | Natural | <2.0 | Nominal 400 | 0.65 |
| 4827 | Synthetic | <2.0 | 225-275 | 0.21 |
| 4848 | Synthetic | <2.0 | 225-275 | 0.25 |
| 4847 | Synthetic | <1.5 | 275-325 | 0.25 |
| 4849 | Synthetic | <1.5 | 275-325 | 0.38 |
| TC 306 | Synthetic | <1.5 | 325-375 | 0.26 |
| TC 307 | Synthetic | <1.5 | 325-375 | 0.26 |

In one embodiment of the invention, the conductive bait matrix 123 contains an amount of electrically conductive particles, preferably graphite, that is sufficient to induce an electrical resistance of the conductive bait matrix 123 in the range from 1 kΩ to 500 kΩ, from 10 kΩ to 100 kΩ, preferably from 40 kΩ to 80 kΩ, more preferably from 1 kΩ to 20 kΩ. it is to be understood that the preferred level of resistance may vary based upon other factors such as the desired battery life and battery provided, the preferred resistance and the materials being used to create the sensor assembly 108 and/or the bait station 102.

Figure 23:
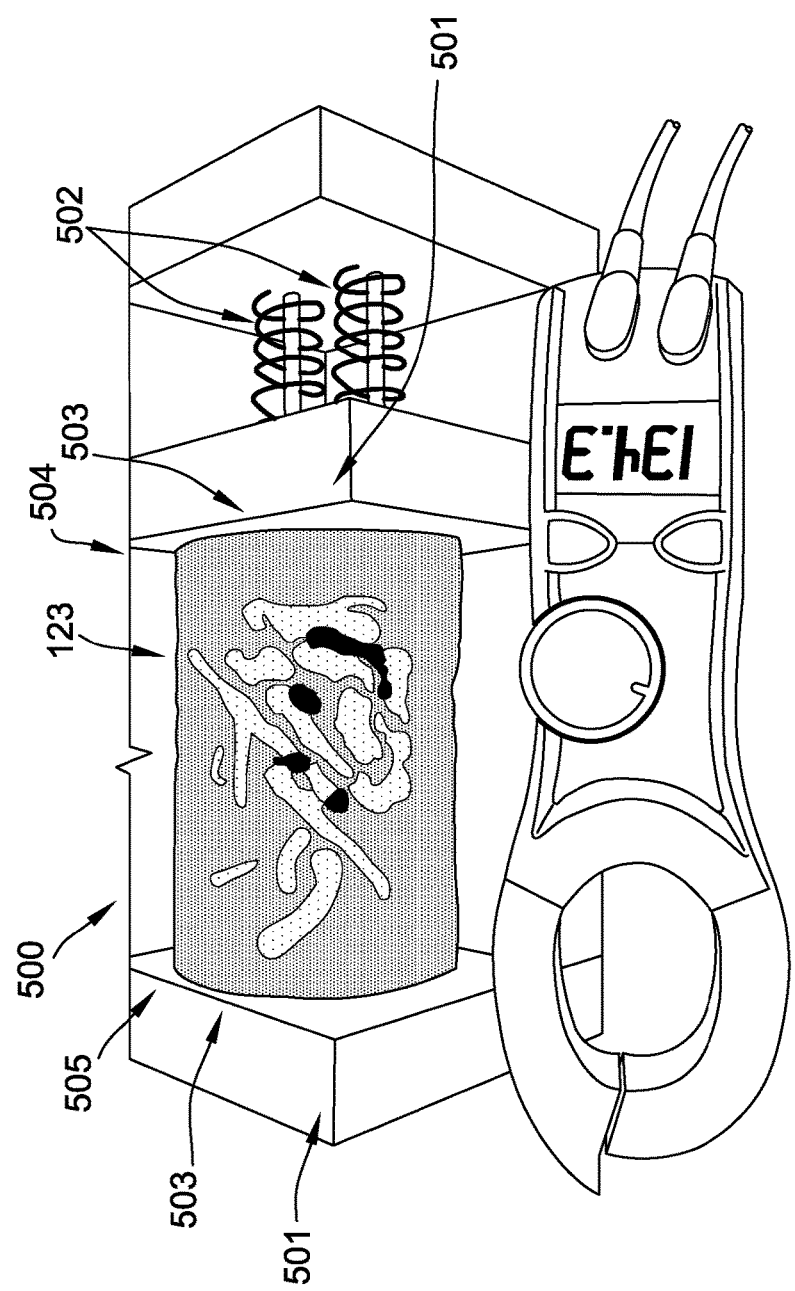
FIG. 23 shows the apparatus 500 to measure the resistance of the conductive bait matrix 123.

To measure the resistance of the conductive bait matrix 123, the conductive bait matrix 123 is placed in a testing apparatus 500 (FIG. 23). The apparatus 500 is built from standard yellow pine lumber that is cut and assembled to form a press. The purpose of the press mechanism is to hold a sample of a conductive bait matrix 123 in place using a nut and bolt configuration 502 to produce an inwardly adjustable force. C110 copper plates 503 are attached to wooden surfaces 501 of the press in opposing positions onto which wire leads 504 and 505 are individually soldered to a corner of each copper plate 503. The leads are connected to a commercially available multimeter, such as for example a model 61-746manufactured by Ideal Industries, Inc. or, alternately, the MM2000 manufactured by Klein Tools.

Testing is conducted on extruded conductive bait matrix samples 123 shaped in the form of a cylinder measuring e.g. approximately 57 mm in diameter, 102 mm in length. The cylinder has a void formed in the center of the matrix that runs along the length of the matrix resulting in a wall thickness of approximately 16 mm. A light coating of commercially available conductive grease (for example MG 846 produced by MG Chemicals) is applied to both ends of the bait matrix 123 to increase the electrical contact between the copper plates 503 and the conductive bait matrix 123. To measure the resistance of the conductive bait matrix 123 sample the multimeter function switch is placed in the proper setting or position for measurements of resistance. After turning on, the multimeter is allowed to stabilize for about 10 seconds for each resistance measurement. Resistance measurements are taken at temperatures between 21 and 24° C. and at relative humidity between 35 and 65%.

In one embodiment of the invention, the conductive bait matrix 123 contains from about 2% to about 25%, preferably about 5% to about 15%, more preferably about 8% to about 12% by weight graphite particles as compared to the weight of the total conductive bait matrix 123. The remainder of the conductive bait matrix 123 in such embodiments would be the carrier material. In other embodiments, a toxicant such as an active ingredient may also be included in the bait matrix and may reduce the concentration of the graphite particles, the concentration of carrier material, or both. Other suitable electrically conductive particles may also be used and remain within the scope of this invention.

The carrier material of the bait matrix 124 according to one embodiment comprises a consumable material (e.g., a material that is consumable and digestible by a pest being monitored using the bait matrix). For example, in one particularly suitable embodiment the carrier material comprises polysaccharide material (e.g., a cellulosic material such as wood flour, alpha cellulose, microcrystalline cellulose or other suitable cellulose material consumable by termites). It is understood that the carrier material may comprise other consumable materials without departing from the scope of this invention.

It is also contemplated that the carrier material may instead, or additionally, comprise a consumable, but non-digestible or essentially non-digestible, material (e.g., a material that is consumable, but not digestible, by a pest being monitored using the bait matrix 124). In one example, a suitable consumable and non-digestible or essentially non-digestable material used as a carrier material is a thermoplastic material and/or a resin-type material. Such a material is capable of melting and being mixed with the electrically conductive particles (and the digestible material, if present) for extrusion together to form the bait matrix 124.

By "essentially non-digestable" it is understood that less than 50% by weight, preferably less than 10% by weight, more preferably less than 1% by weight, still more preferably less than 0.1% by weight of the orally acquired material are subsequently digested by the pest being monitored using the bait matrix 124. Digestible for purposes of this application means capable of being broken down to a simpler form by the consumer after consumption.

It is also contemplated that the carrier material may instead, or additionally, comprise a displaceable material, i.e. a material that can be dislodged by the pest without the pest eating and/or digesting it.

Thermoplastic materials in general are well known materials that become pliable or moldable above a specific temperature and solidify upon cooling. There are many examples of suitable thermoplastic materials including but not limited to High Temperature Thermoplastics like polyphthalamide (PPA), Polyphenylene sulfide (PPS), Liquid-crystal polymers (LCP), Polyether ether ketone (PEEK), Polyetherimid (PEI), Polyarylsulphones (PSU), Polyethersulfone (PES), Polyphenylsulfone (PPSU)

Eingineering thermoplastics like syndiotactic polystyrene (SPS), Polyethylene terephthalate (PET), Polybutylene terephthalate (PBT), Polyoxymethylene (POM), Polyamide (PA), polypropylene (PP), polycarbonate (PC), Poly(p-phenylene oxide)(PPE), Poly(methyl methacrylate) (PMMA), Acrylonitrile butadiene styrene (ABS), styrene-acrylonitrile copolymer (SAN), Acrylonitrile Styrene Acrylate (ASA)

Standard thermoplastics like High-density polyethylene (HDPE), Low-density polyethylene (LDPE), Linear low-density polyethylene (LLDPE), poly(butylene adipate-co-terephthalate)(PBAT), Acrylonitrile butadiene styrene (ABS).

The carrier material in one embodiment comprises a thermoplastic material that has a melting point of below about 220° C., or below about 180° C., or below about 160° C., or below about 140° C.

In one embodiment of the invention, the conductive bait matrix 123 also comprises at least one pesticide active ingredient.

If the conductive bait matrix 123 also comprises a pesticide active ingredient, the processing temperature used to melt or soften the thermoplastic material when making the carrier material is preferably a temperature less than that at which the functionality of the pesticide active ingredient is nullified.

Suitable thermoplastic materials include, without limitation, cellulose acetate propionate (CAP), cellulose acetate butyrate (CAB), or a polyester. US 2015/0305326 A1, which is herewith incorporated by reference, describes particularly suitable thermoplastic materials in chapters [0077] and [0078]. In one particularly suitable embodiment, the thermoplastic carrier material is a polyester having a relatively low melt temperature, e.g. where the melt temperature is below 170° C., where the melt temperature is below 160° C., where the melt temperature is below 150° C., where the melt temperature is below 140° C., where the melt temperature is below 130° C. Suitable polyesters are for example the polyesters disclosed in WO-A 92/09654 and WO-A 96/15173, which are hereby incorporated by reference.

Preferred suitable polyesters are aliphatic or aliphatic/aromatic (semiaromatic) compostable polyesters with intrinsic viscosities to DIN 53728 of from 150 to 320 cm3/g and acid numbers to DIN EN 12634 smaller than 1.2 mg KOH/g, preferably smaller than 1.0 mg KOH/g.

Other preferred polyesters are compostable semiaromatic polyesters with intrinsic viscosities greater than 160 cm3/g and acid numbers smaller than 1.0 mg KOH/g, and with melt volume-flow rate (MVR) smaller than 6.0 cm3/10 min (measured at 190 degrees centigrade, with a weight of 216 kg).

The aforementioned preferred compostable semiaromatic polyesters and their process of manufacture are disclosed in WO-A 09/127556, which is hereby incorporated by reference. The thermoplastic material may also comprise mixtures of biodegradable semiaromatic polyesters with polymers that are susceptible to hydrolysis, examples being PLA (polylactide); PHA (polyhydroxyalkanoates), PBS (polybutylene succinate), and starch. One particularly suitable polyester is sold by BASF SE under the tradename Ecoflex®. This material is a compostable, statistical, aliphatic-aromatic copolyester based on the monomers 1.4-butanediol, adipic acid and terephthalic acid in the polymer chain. The melt temperature of Ecoflex® is approximately 110-120° C.

The thermoplastic polymer can include a single polymer or a mixture of at least two different polymers. For example, in one embodiment, the thermoplastic polymer includes a mixture of a relatively high molecular weight polymer and a relatively low molecular weight polymer. Polyesters like e.g. Ecoflex®, their manufacture and uses are i.a. described in patent applications EP-A 1656423, EP-A 937120, EP-A 950689, EP-A 1838784, EP-A 947559, EP-A 965615, which are herewith incorporated by reference. In one embodiment, the thermoplastic polymer comprises a mixture of Ecoflex® and Poly lactic acid (PLA) like e.g. Ecovio®.

One advantage of using a lower melt temperature polyester polymer (e.g., as opposed to, e.g., CAP or CAB) as the carrier material is in extruding a bait matrix that includes an active ingredient which decomposes at higher temperatures like e.g. above 160° C., above 180° C., above 200° C. For example, CAP and CAB typically have a melt temperature closer to about 180° C. Extruding at this higher temperature may have more of a negative impact on an active ingredient than extruding at the lower temperature of the polyester polymer, e.g., the Ecoflex®. It is to be understood that a melt temperature of greater than 180° C. may be used. Additionally, it is believed, based on preliminary studies, that termites show a preference to a conductive bait matrix comprised of graphite and Ecoflex® than to a conductive bait matrix comprised of graphite and CAB or CAP, in the same relative concentrations as shown in Tables 3 and 4 and set forth in more detail in Example 2.

As used herein, a substance or a mixture of substances is considered to be "biodegradable" if this substance or the mixture of substances has a percentage degree of biodegradation of at least 60% in the processes defined in DIN EN 13432. Other methods of determining biodegradability are described by way of example in ABNT 15448-1/2 and ASTM D6400. As used herein, a substance or a mixture of substances is considered to be "compostable" if this substance or mixture of substances may be degraded by microorganisms or other biological processes during composting to yield $CO_2$, water, inorganic compounds, and biomass at a rate consistent with other known compostable materials and that leaves no visible, distinguishable or toxic residues and/or a substance or mixture of substances meets the criteria set forth in the any of the following compostable standards EP—DIN EN 13432, US—ASTM D 6400 or JP—GreenPla standard.

The result of the biodegradability and/or compostability is generally that the substance, as e.g. the polyester breaks down within an appropriate and demonstrable period. The degradation may be brought about enzymatically, hydrolytically, oxidatively, and/or via exposure to electromagnetic radiation, such as UV radiation, and is mostly predominantly caused by exposure to microorganisms, such as bacteria, yeasts, fungi, and algae. An example of a method of quantifying the biodegradability mixes polyester with compost and stores it for a particular time. By way of example, according to DIN EN 13432, $CO_2$-free air is passed through ripened compost during the composting process and the compost is subjected to a defined temperature profile. Biodegradability is defined here by way of the ratio of the net amount of $CO_2$ liberated from the specimen (after deducting the amount of $CO_2$ liberated by the compost without the specimen) to the maximum possible amount of $CO_2$ liberated by the specimen (calculated from the carbon content of the specimen), this ratio being defined as the percentage biodegradability. Even after a few days of composting, biodegradable polyesters or biodegradable polyester mixtures generally show marked signs of degradation, for example fungal growth, cracking, and perforation.

Polyesters are well known polymers. They comprise monomers in polymerized form, such as diols and diacids (or diesters), or hydroxyacids (or hydroxyesters). Suitable polyester are for example aliphatic polyester. These include homopolymers of aliphatic hydroxycarboxylic acids or lactones, and also copolymers or block copolymers of different hydroxycarboxylic acids or lactones or mixtures of these. These aliphatic polyesters may also contain units of diols and/or of isocyanates. The aliphatic polyesters may also contain units which derive from tri- or polyfunctional compounds, for example from epoxides, from acids or from triols. The aliphatic polyesters may contain the latter units as individual units, or a number of these, possibly together with the diols and/or isocyanates. Processes for preparing aliphatic polyesters are known to the skilled worker. In preparing the aliphatic polyesters it is, of course, also possible to use mixtures made from two or more comonomers and/or from other units, for example from epoxides or from polyfunctional aliphatic or aromatic acids, or from polyfunctional alcohols. The aliphatic polyesters generally have molar masses (number-average) of from 10,000 to 100,000 g/mol.

Examples of aliphatic polyesters are polymeric reaction products of lactic acid, poly-3-hydroxybutanoates, or polyesters built up from aliphatic or cycloaliphatic dicarboxylic acids and from aliphatic or cycloaliphatic diols. The aliphatic polyesters may also be random or block copolyesters which contain other monomers. The proportion of the other monomers is generally up to 10 percent by weight. Preferred comonomers are hydroxycarboxylic acids or lactones or mixtures of these.

Polymeric reaction products of lactic acid are known per se or may be prepared by processes known per se. Besides polylactide, use may also be made of those copolymers or block copolymers based on lactic acid with other monomers. Linear polylactides are mostly used. However, branched lactic acid polymers may also be used. Examples of branching agents are polyfunctional acids or alcohols. Polylactides which may be mentioned as an example are those obtainable essentially from lactic acid or from its C1-C4-alkyl esters or mixtures of these, with at least one aliphatic C4-C10 dicarboxylic acid and with at least one C3-C10 alkanol having from three to five hydroxyl groups.

Poly-3-hydroxybutanoates are homopolymers or copolymers of 3-hydroxybutanoic acid or mixtures thereof with 4-hydroxybutanoic acid and with 3-hydroxyvaleric acid, in particular with a proportion by weight of up to 30 percent, preferably up to 20 percent, of the last-named acid. Suitable polymers of this type also include those with R-stereospecific configuration. Polyhydroxybutanoates or copolymers of these can be prepared microbially.

Processes for the preparation from various bacteria and fungi are known as well as a process for preparing stereospecific polymers. It is also possible to use block copolymers of the above-mentioned hydroxycarboxylic acids or lactones, or of their mixtures, oligomers or polymers.

Suitable polyesters built up from aliphatic or cycloaliphatic dicarboxylic acids and from aliphatic or cycloaliphatic diols are those built up from aliphatic or cycloaliphatic dicarboxylic acids or from mixtures of these, and from aliphatic or cycloaliphatic diols, or from mixtures of these. According to the invention either random or block copolymers may be used.

Suitable aliphatic dicarboxylic acids generally have from 2 to 10 carbon atoms. They may be either linear or branched. Cycloaliphatic dicarboxylic acids as used herein are generally those having from 7 to 10 carbon atoms, and in particular those having 8 carbon atoms. However, in principle use may also be made of dicarboxylic acids having a larger number of carbon atoms, for example having up to 30 carbon atoms. Examples include, without limitation: malonic acid, succinic acid, glutaric acid, adipic acid, pimelic acid, azelaic acid, sebacic acid, fumaric acid, 2,2-dimethylglutaric acid, suberic acid, 1,3-cyclopentanedicarboxylic acid, 1,4-cyclohexanedicarboxylic acid, 1,3-cyclohexanedicarboxylic acid, diglycolic acid, itaconic acid, maleic acid and 2,5-norbornanedicarboxylic acid, preferably adipic acid. Mention should also be made of ester-forming derivatives of the abovementioned aliphatic or cycloaliphatic dicarboxylic acids, which may likewise be used, in particular the di-C1-C6-alkyl esters, such as dimethyl, diethyl, di-n-propyl, diisopropyl, di-n-butyl, diisobutyl, di-tert-butyl, di-n-pentyl, diisopentyl and di-n-hexyl esters. Anhydrides of the dicarboxylic acids may likewise be used.

The dicarboxylic acids or ester-forming derivatives of these may be used individually or as a mixture of two or more of these.

Suitable aliphatic or cycloaliphatic diols generally have from 2 to 10 carbon atoms. They may be either linear or branched. Examples are 1,4-butanediol, ethylene glycol, 1,2- or 1,3-propanediol, 1,6-hexanediol, 1,2- or 1,4-cyclohexanediol or mixtures of these.

Examples of aliphatic polyesters are aliphatic copolyesters as described in WO 94/14870, in particular aliphatic copolyesters made from succinic acid, from its diesters, or from mixtures with other aliphatic acids or, respectively, diesters, for example glutaric acid and butanediol, or mixtures made from this diol with ethylene glycol, propanediol or hexanediol or mixtures of these. In another embodiment, preferred aliphatic polyesters include polycaprolactone.

As used herein, semiaromatic polyesters refers to polyester, which comprise aliphatic and aromatic monomers in polymerizied form. The term semiaromatic polyesters is also intended to include derivatives of semiaromatic polyesters, such as semiaromatic polyetheresters, semiaromatic polyesteramides, or semiaromatic polyetheresteramides. Among suitable semiaromatic polyesters are linear non-chain-extended polyesters (WO 92/09654). Preference is given to chain-extended and/or branched semiaromatic polyesters. The latter are disclosed in, for example, WO 96/15173, WO 96/15174, WO 96/15175, WO 96/15176, WO 96/21689, WO 96/21690, WO 96/21691, WO 96/21689, WO 96/25446, WO 96/25448, and WO 98/12242, expressly incorporated herein by way of reference. Mixtures of different semiaromatic polyesters may also be used. In particular, the term semiaromatic polyesters is intended to mean products such as Ecoflex® (BASF SE) and Eastar® Bio and Origo-Bi (Novamont).

Among particularly preferred semi-aromatic polyesters are polyesters which comprise the following significant components A) an acid component composed of a1) from 30 to 99 mol % of at least one aliphatic, or at least one cycloaliphatic, dicarboxylic acid, or its ester-forming derivatives, or a mixture of these a2) from 1 to 70 mol % of at least one aromatic dicarboxylic acid, or its ester-forming derivative, or a mixture of these, and a3) from 0 to 5 mol % of a compound comprising sulfonate groups, and B) a diol component selected from at least one C2-C12 alkanediol and at least one C5-C10 cycloalkanediol, or a mixture of these. If desired, the semi-aromatic polyester may also comprise one or more components selected from C) and D), wherein C) is a component selected from c1) at least one dihydroxy compound comprising ether functions and having the formula I

where n is 2, 3 or 4 and m is a whole number from 2 to 250, c2) at least one hydroxycarboxylic acid of the formula IIa or IIb

where p is a whole number from 1 to 1500 and r is a whole number from 1 to 4, and G is a radical selected from the group consisting of phenylene, $(CH_2)_q$—, where q is a whole number from 1 to 5, —C(R)H and —C(R)HCH$_2$, where R is methyl or ethyl, c3) at least one amino-C2-C12 alkanol, or at least one amino-C5-C10 cycloalkanol, or a mixture of these, c4) at least one diamino-C1-C8 alkane, c5) at least one 2,2'-bisoxazoline of the formula III

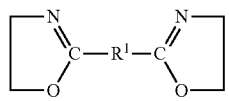

where $R^1$ is a single bond, a (CH2)z-alkylene group, where z=2, 3 or 4, or a phenylene group, c6) at least one aminocarboxylic acid selected from the group consisting of the naturally occurring amino acids, polyamides obtainable by polycondensing a dicarboxylic acid having from 4 to 6 carbon atoms with a diamine having from 4 to 10 carbon atoms, compounds of the formulae IVa and IVb

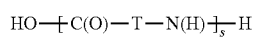

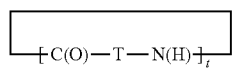

where s is a whole number from 1 to 1500 and t is a whole number from 1 to 4, and T is a radical selected from the group consisting of phenylene, $(CH_2)_u$—, where u is whole number from 1 to 12, C(R2)H and C(R2)HCH2, where R2 is methyl or ethyl, and polyoxazolines having the repeat unit V

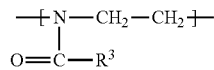

where R3 is hydrogen, C1-C6-alkyl, C5-C8-cycloalkyl, phenyl, either unsubstituted or with up to three C1-C4-alkyl substituents, or tetrahydrofuryl, or a mixture composed of c1) to c6), and wherein D) is a component selected from d1) at least one compound having at least three groups capable of ester formation, d2) at least one isocyanate, d3) at least one divinyl ether, or a mixture composed of d1) to d3).

The acid component A of the semiaromatic polyesters may comprise from 30 to 70 mol %, in particular from 40 to 60 mol %, of a1, and from 30 to 70 mol %, in particular from 40 to 60 mol %, of a2.

Aliphatic acids and the corresponding derivatives a1 which may be used are generally those having from 2 to 10 carbon atoms. They may be either linear or branched. The cycloaliphatic dicarboxylic acids are generally those having from 7 to 10 carbon atoms and in particular those having 8 carbon atoms. In principle, however, it is also possible to use dicarboxylic acids having a larger number of carbon atoms, for example having up to 30 carbon atoms. Examples include, without limitation: malonic acid, succinic acid, glutaric acid, 2 methylglutaric acid, 3-methylglutaric acid, adipic acid, pimelic acid, azelaic acid, sebacic acid, fumaric acid, 2,2-dimethylglutaric acid, suberic acid, 1,3-cyclopentane¬dicarboxylic acid, 1,4-cyclohexanedicarboxylic acid, 1,3-cyclohexanedicarboxylic acid, diglycolic acid, itaconic acid, maleic acid, brassylic acid, and 2,5-norbornanedicarboxylic acid. Ester-forming derivatives of the abovementioned aliphatic or cycloaliphatic dicarboxylic acids which may also be used and which may be mentioned are in particular the di-C1-C6-alkyl esters, such as dimethyl, diethyl, di-n-propyl, diisopropyl, di-n-butyl, diisobutyl, di-tert-butyl, di-n-pentyl, diisopentyl or di-n-hexyl esters. It is also possible to use anhydrides of the dicarboxylic acids.

Dicarboxylic acids or their ester-forming derivatives may be used individually or in the form of a mixture composed of two or more of these.

In another embodiment, succinic acid, adipic acid, azelaic acid, sebacic acid, brassylic acid, or respective ester-forming derivatives thereof, or a mixture of these may be used. Aliphatic dicarboxylic acid may comprise sebacic acid or a mixture of sebacic acid with adipic acid, if polymer mixtures with "hard" or "brittle" components for example polyhydroxybutyrate or in particular polylactide, are prepared. In another embodiment, the aliphatic dicarboxylic acid may comprise succinic acid or a mixture of succinic acid with adipic acid if polymer mixtures with "soft" or "tough" components, for example polyhydroxybutyrate-co-valerate, are prepared.

A further advantage of succinic acid, azelaic acid, sebacic acid, and brassylic acid is that they are accessible renewable raw materials.

Aromatic dicarboxylic acids a2 which may be mentioned are generally those having from 8 to 12 carbon atoms and preferably those having 8 carbon atoms. By way of example, mention may be made of terephthalic acid, isophthalic acid, 2,6-naphthoic acid and 1,5-naphthoic acid, and also ester-forming derivatives of these. Particular mention may be made here of the di-C1-C6-alkyl esters, e.g. dimethyl, diethyl, di-n-propyl, diisopropyl, di-n-butyl, diisobutyl, di-tert-butyl, di-n-pentyl, diisopentyl, or di n-hexyl esters. The anhydrides of the dicarboxylic acids a2 are also suitable ester-forming derivatives.

However, in principle it is also possible to use aromatic dicarboxylic acids a2) having a greater number of carbon atoms, for example up to 20 carbon atoms.

The aromatic dicarboxylic acids or ester-forming derivatives of these a2) may be used individually or as a mixture of two or more of these.

A compound comprising sulfonate groups a3) is usually one of the alkali metal or alkaline earth metal salts of a sulfonate-containing dicarboxylic acid or ester-forming derivatives thereof, such as alkali metal salts of 5-sulfoisophthalic acid or a mixture of these.

In one embodiment, the acid component A comprises from 40 to 60 mol % of a1, from 40 to 60 mol % of a2 and from 0 to 2 mol % of a3. In another embodiment, the acid component A comprises from 40 to 59.9 mol % of a1, from 40 to 59.9 mol % of a2 and from 0.1 to 1 mol % of a3, in particular from 40 to 59.8 mol % of a1, from 40 to 59.8 mol % of a2 and from 0.2 to 0.5 mol % of a3.

Diols B are generally selected from the group consisting of branched or linear alkanediols having from 2 to 12 carbon atoms, or from the group consisting of cycloalkanediols having from 5 to 10 carbon atoms. Examples of alkanediols are ethylene glycol, 1,2-propanediol, 1,3-propanediol, 1,2- butanediol, 1,4-butanediol, 1,5-pentanediol, 2,4-dimethyl-2-ethyl-1,3-hexanediol, 2,2-dimethyl-1,3-propanediol, 2-ethyl-2-butyl-1,3-propanediol, 2-ethyl-2-isobutyl-1,3-propanediol and 2,2,4-trimethyl-1,6-hexanediol, in particular ethylene glycol, 1,3-propanediol, 1,4-butanediol or 2,2-dimethyl-1,3-propanediol (neopentyl glycol); cyclopentanediol, 1,4-cyclohexanediol, 1,2-cyclohexanedimethanol, 1,3-cyclohexanedimethanol, 1,4-cyclohexanedimethanol or 2,2,4,4-tetramethyl-1,3-cyclobutanediol. Particular preference is given to 1,4-butanediol, in particular in combination with adipic acid as component a1), and 1,3-propanediol, in particular in combination with sebacic acid as component a1). Another advantage of 1,3 propanediol is that it is an available renewable raw material. It is also possible to use mixtures of different alkanediols.

Depending on whether an excess of acid groups or of OH end groups is desired, either component A or component B may be used in excess. In one preferred embodiment, the molar ratio of the components A and B used may be from 0.4:1 to 1.5:1, preferably from 0.6:1 to 1.1:1.

Besides components A and B, the polyesters may comprise other components.

Dihydroxy compounds c1 which may be used are diethylene glycol, triethylene glycol, polyethylene glycol, polypropylene glycol and polytetrahydrofuran (polyTHF), particularly preferably diethylene glycol, triethylene glycol and polyethylene glycol, and mixtures of these may also be used, as may compounds which have different variables n (see formula I), for example polyethylene glycol which comprises propylene units (n=3), obtainable, for example, by using methods of polymerization known per se and polymerizing first with ethylene oxide and then with propylene oxide, and particularly preferably a polymer based on polyethylene glycol with different variables n, where units formed from ethylene oxide predominate. The molar mass (Mn) of the polyethylene glycol is generally selected within the range from 250 to 8000 g/mol, preferably from 600 to 3000 g/mol.

In one embodiment for preparing the semi-aromatic polyesters use may be made, for example, of from 15 to 98 mol %, preferably from 60 to 99.5 mol %, of the diols B and from 2 to 85 mol %, preferably from 0.5 to 40 mol %, of the dihydroxy compounds c1, based on the molar amount of B and c1.

In one preferred embodiment, the hydroxycarboxylic acid c2) used is: glycolic acid, D-, L- or D,L-lactic acid, 6-hydroxyhexanoic acid, cyclic derivatives of these, such as glycolide (1,4-dioxane-2,5-dione), D- or L-dilactide (3,6-dimethyl-1,4-dioxane-2,5-dione), p-hydroxybenzoic acid, or else their oligomers and polymers, such as 3-polyhydroxybutyric acid, polyhydroxyvaleric acid, polylactide (obtainable, for example, as NatureWorks® 4042D (NatureWorks) or else a mixture of 3-polyhydroxybutyric acid and polyhydroxyvaleric acid (obtainable from PHB Industrial, Tianan, or Metabolix) and, for preparing semiaromatic polyesters, particularly preferably the low-molecular-weight and cyclic derivatives thereof.

Examples of amounts which may be used of the hydroxycarboxylic acids are from 0.01 to 50% by weight, preferably from 0.1 to 40% by weight, based on the amount of A and B.

The amino-C2-C12 alkanol or amino-C5-C10 cycloalkanol used (component c3) may include 4-aminomethyl-cyclohexane-methanol, are preferably amino-C2-C6 alkanols, such as 2-aminoethanol, 3-amino-propanol, 4-aminobutanol, 5-aminopentanol or 6-aminohexanol, or else amino-C5-C6 cycloalkanols, such as aminocyclopentanol and aminocyclohexanol, or mixtures of these.

The diamino-C1-C8 alkanes (component c4) used are preferably diamino-C4-C6 alkanes, such as 1,4-diaminobutane, 1,5-diaminopentane or 1,6-diaminohexane (hexamethylenediamine, "HMD").

In one embodiment for preparing the semiaromatic polyesters, use may be made of from 0.5 to 99.5 mol %, preferably from 0.5 to 50 mol %, of c3, based on the molar amount of B, and of from 0 to 50 mol %, preferably from 0 to 35 mol %, of c4, based on the molar amount of B.

The 2,2'-bisoxazolines c5 of the formula III are generally obtainable via the process of Angew. Chem. Int. Edit., Vol. 11 (1972), pp. 287-288. Bisoxazolines are those where R1 is a single bond, (CH2)z-alkylene, where z=2, 3 or 4, for example methylene, ethane-1,2-diyl, propane-1,3-diyl or propane-1,2-diyl, or a phenylene group. Particularly preferred bisoxazolines which may be mentioned are 2,2'-bis(2-oxazoline), bis(2-oxazolinyl)methane, 1,2-bis(2-oxazolinyl)ethane, 1,3-bis(2-oxazolinyl)propane and 1,4-bis(2-oxazolinyl)butane, in particular 1,4-bis(2-oxazolinyl)benzene, 1,2-bis(2-oxazolinyl)benzene or 1,3-bis(2-oxazolinyl)benzene.

In preparing the semiaromatic polyesters use may, for example, be made of from 70 to 98 mol % of B, up to 30 mol % of c3 and from 0.5 to 30 mol % of c4 and from 0.5 to 30 mol % of c5, based in each case on the total of the molar amounts of components B, c3, c4 and c5. In another embodiment, use may be made of from 0.1 to 5% by weight, preferably from 0.2 to 4% by weight, of c5, based on the total weight of A and B.

The component c6 used may be naturally occurring aminocarboxylic acids. These include valine, leucine, isoleucine, threonine, methionine, phenylalanine, tryptophan, lysine, alanine, arginine, aspartamic acid, cysteine, glutamic acid, glycine, histidine, proline, serine, tyrosine, asparagine and glutamine.

Preferred aminocarboxylic acids of the formulae IVa and IVb are those where s is a whole number from 1 to 1000 and t is a whole number from 1 to 4, preferably 1 or 2, and t has been selected from the group consisting of phenylene and —(CH2)u-, where u is 1, 5, or 12.

c6 may also be a polyoxazoline of the formula V. However, c6 may also be a mixture of different aminocarboxylic acids and/or polyoxazolines.

In one embodiment, the amount of c6 used may be from 0.01 to 50% by weight, preferably from 0.1 to 40% by weight, based on the total amount of components A and B.

Among other components which may be used, if desired, for preparing the semiaromatic polyesters are compounds d1 which comprise at least three groups capable of ester formation.

The compounds d1 may comprise from three to ten functional groups which are capable of developing ester bonds. Particularly preferred compounds d1 have from three to six functional groups of this type in the molecule, in particular from three to six hydroxy groups and/or carboxy groups. Examples which should be mentioned are:

tartaric acid, citric acid, maleic acid; trimethylolpropane, trimethylolethane;

pentaerythritol; polyethertriols; glycerol; trimesic acid; trimellitic acid, trimellitic anhydride; pyromellitic acid, pyromellitic dianhydride, and hydroxyisophthalic acid.

The amounts generally used of the compounds d1 are from 0.01 to 15 mol %, preferably from 0.05 to 10 mol %, particularly preferably from 0.1 to 4 mol %, based on component A.

Components d2 used are an isocyanate or a mixture of different isocyanates. Aromatic or aliphatic diisocyanates may be used. However, higher-functionality isocyanates may also be used. Aromatic diisocyanate d2 is especially tolylene 2,4-diisocyanate, tolylene 2,6-diisocyanate, diphenylmethane 2,2'-diisocyanate, diphenylmethane 2,4'-diisocyanate, diphenylmethane 4,4'-diisocyanate, naphthylene 1,5-diisocyanate or xylylene diisocyanate. By way of example, it is possible to use the isocyanates obtainable as Basonat® from BASF SE.

Among these, particular preference is given to diphenylmethane 2,2'-, 2,4'- and 4,4'-diisocyanate as component d2. The latter diisocyanates are generally used as a mixture.

A three-ring isocyanate d2 which may also be used is tri(4-isocyanophenyl)methane. Multi-ringed aromatic diisocyanates arise during the preparation of single- or two-ring diisocyanates, for example.

Component d2 may also comprise subordinate amounts, e.g. up to 5% by weight, based on the total weight of component d2, of uretdione groups, for example for capping the isocyanate groups.

Aliphatic diisocyanate d2 is primarily a linear or branched alkylene diisocyanate or cycloalkylene diisocyanate having from 2 to 20 carbon atoms, preferably from 3 to 12 carbon atoms, e.g. hexamethylene 1,6-diisocyanate, isophorone diisocyanate, or methylenebis(4-isocyanatocyclohexane). Hexamethylene 1,6-diisocyanate and isophorone diisocyanate are particularly preferred aliphatic diisocyanates d2.

Among the preferred isocyanurates are the aliphatic isocyanurates which derive from C2-C20, preferably C3-C12, cycloalkylene diisocyanates or alkylene diisocyanates, e.g. isophorone diisocyanate or methylenebis(4-isocyanatocyclohexane). The alkylene diisocyanates here may be either linear or branched. Particular preference is given to isocyanurates based on n-hexamethylene diisocyanate, for example cyclic trimers, pentamers, or higher oligomers of n-hexamethylene diisocyanate.

The amounts generally used of component d2 are from 0.01 to 5 mol %, preferably from 0.05 to 4 mol %, particularly preferably from 0.1 to 4 mol %, based on the total of the molar amounts of A and B.

Divinyl ethers d3 which may be used are generally any of the customary and commercially available divinyl ethers. Preference is given to the use of 1,4-butanediol divinyl ethers, 1,6-hexanediol divinyl ethers or 1,4-cyclohexanedimethanol divinyl ethers or a mixture of these.

The amounts of the divinyl ethers preferably used are from 0.01 to 5% by weight, especially from 0.2 to 4% by weight, based on the total weight of A and B.

Examples of semiaromatic polyesters are based on the following components: A, B, d1; A, B, d2; A, B, d1, d2; A, B, d3; A, B, c1; A, B, c1, d3; A, B, c3, c4; A, B, c3, c4, c5; A, B, d1, c3, c5; A, B, c3, d3; A, B, c3, d1; A, B, c1, c3, d3; or A, B, c2. Among these, particular preference is given to semiaromatic polyesters based on A, B and d1, or A, B and d2, or on A, B, d1 and d2. In another preferred embodiment, the semiaromatic polyesters are based on A, B, c3, c4 and c5 or A, B, d1, c3 and c5.

While the polyester polymer according to the above disclosure is a biodegradable polyester polymer, it is understood that the polyester polymer may be non-biodegradable without departing from the scope of this invention.

In one suitable example, the carrier material comprises both a polysaccharide material, such as a cellulosic material, and a thermoplastic material, such as a polyester.

For example, in such an embodiment the thermoplastic material may comprise about 20 to about 40 weight % of the bait matrix 124.

Some suitable compositions of the conductive bait matrix according to this invention are shown in Table 1a:

TABLE 1a

| Cellulose | Graphite | Thermoplastic Polyester |
|---|---|---|
| 75 | 5 | 20 |
| 70 | 10 | 20 |
| 65 | 15 | 20 |
| 65 | 5 | 30 |
| 60 | 10 | 30 |
| 55 | 15 | 30 |
| 55 | 5 | 40 |
| 50 | 10 | 40 |
| 45 | 5 | 50 |
| 45 | 15 | 40 |
| 40 | 10 | 50 |
| 35 | 15 | 50 |
| 35 | 5 | 60 |
| 30 | 10 | 60 |
| 25 | 15 | 60 |

It is understood that other suitable manufacturing processes are also contemplated for combining the carrier material and electrically conductive particles to form the conductive bait matrix 123 such as, without limitation, coextrusion, compaction, immersion, molding, suspension and the like.

One preferred embodiment of the invention is a method for making a workpiece that includes:
(1) providing a mixture of
   a. a softened or molten thermoplastic polymer having a softening or melting point below about 220° C.
   b. a phagostimulant material for the target pest and
   c. a material comprising conductive particles;
(2) forming the mixture to provide a workpiece having a desired shape; and
(3) cooling the workpiece to a temperature below the softening or melting point of the plastic to provide a solid composite article.

The workpiece preferably is or comprises the conductive bait matrix.

As used herein, the term "molten" is intended to refer to a state of a thermoplastic material in which the material is fully melted, partially melted, or sufficiently softened or tacky that the polymer can be formed, for example by extrusion or molding and then cooling, into a plastic matrix. Similarly, the term "melting point" as used herein is intended to refer to the temperature at which a given material, polymer or mixture of polymers melts, softens or becomes tacky, and encompasses the glass transition temperature for amorphous polymers. A person skilled in the art will appreciate that the melting point of a given material, polymer or mixture of polymers can be modified by contacting the material, polymer or mixture of polymers with certain solvents and/or other additives. In one embodiment, the workpiece is formed by extrusion.

To make a the solid composite article in accordance with one embodiment, a mixture of a granular or particulate thermoplastic polymer, a phagostimulant material for the target pest and a material comprising a plurality of conductive particles is provided and the mixture is then compounded to mix the components, and extruded or molded at a predetermined temperature and pressure. The polymer, the phagostimulant material and the material comprising a plurality of conductive particles can be combined using standard mixing or compounding techniques to mix the components and drive off excess moisture. For example, the materials can be mixed in a rotational mixer or compounding extruder. Heat is applied if needed to bring the mixture to a temperature sufficiently high to make the thermoplastic polymer pliable or plastic and therefore suitable for shaping, such as by extrusion. In one embodiment, the temperature is at least as high as the melting point of the polymer. In another embodiment, the temperature is at least as high as the glass transition temperature of the polymer.

One skilled in the art will recognize that higher temperatures may be needed, and that the processing temperature may be optimized to allow the polymer to be processed as long as the temperature is not raised to a point that results in substantial harm to other components of the composite, such as, for example, charring the phagostimulant material. A person of ordinary skill in the art will also understand that the inclusion of a solvent in the mixture can modify the softening temperature of the thermoplastic material. In embodiments in which a solvent is present, it is understood that softening at the surface of a polymer, as modified by the solvent, might begin at a temperature that is lower than the natural melting point of the polymer in the absence of the solvent. In other words, temperatures below the natural melting point of the polymer may be suitable molding temperatures in embodiments in which the solvent is effective to soften the surface of the polymer at a temperature below its natural melting point.

A wide variety of extrusion or molding techniques can be used, many examples of which are known in the art. While it is not intended that the present application be limited by any theory, it is believed that, under extrusion or molding conditions applied in methods described herein, the polymer granules become softened, tacky or fully melted. When this occurs, pressure exerted upon the mixture causes softened polymer granules to contact one another and adhere together or causes the polymer to fully melt, whereby the molten polymer forms a continuous phase in the mixture. The temperature at which the compression is applied is a temperature high enough to achieve a desired level of polymer particle adhesion or polymer melting. It is understood that a wide variety of material specifications (such as polymer type, polymer size, granule size distribution and ratio of ingredients) and also a wide variety of process parameters (such as temperature and pressure) can be used to provide articles having various advantageous characteristics. It is within the ability of a skilled person, armed with the description of the present application, to select, without undue experimentation, advantageous combinations of materials and parameters to provide articles having differing amounts of conductive particles and different physical properties.

In one manner of practicing the method, the molten mixture is provided by mixing the polymer, the phagostimulant material and the material comprising a plurality of conductive particles to form a mixture and then compounding said mixture under elevated pressure and temperature to form a molten material.

In another manner of practicing the method, the method includes forming pellets or flakes of the mixture prior to compounding.

In one manner of making the workpiece, all of the components are mixed together and then the mixture is heated above the melting point of the thermoplastic polymer included therein, e.g. up to about 220 degrees centigrade in some embodiments, in a device, such as a twin screw mixer, that is capable of additional mixing followed by extrusion through a die, which imparts a specific cross-sectional profile to the composite material, and then cooling in a water bath or spray.

In another manner of forming the workpiece, the polymer, the phagostimulant material and the material comprising a plurality of conductive particles are combined within an extruder under positive pressure and at elevated temperature and are thereafter extruded to provide an elongated workpiece.

In another manner of forming the workpiece, the thermoplastic polymer and the material comprising a plurality of conductive particles are individually but simultaneously fed upstream into the extruder and the phagostimulant material is added downstream into the extruder.

In another manner of forming the workpiece, the thermoplastic polymer, the material comprising a plurality of conductive particles, and the phagostimulant material are individually but simultaneously fed into the extruder.

In one preferred embodiment, the surface of the finished workpiece is structurally inhomogeneous on a mm to cm scale. In one embodiment the surface comprises a plurality of cavities of a width from 0.1 mm to 100 mm, from 1 mm to 50 mm, from 1 mm to 20 mm, and a depth from 0.1 mm to 10 mm, from 1 mm to 5 mm, from 1 mm to 3 mm. The cavities can be of any shape. The cavities can be interconnected with or separated from each other. Individual cavities on the same workpiece can be different in size and shape.

Figure 16:
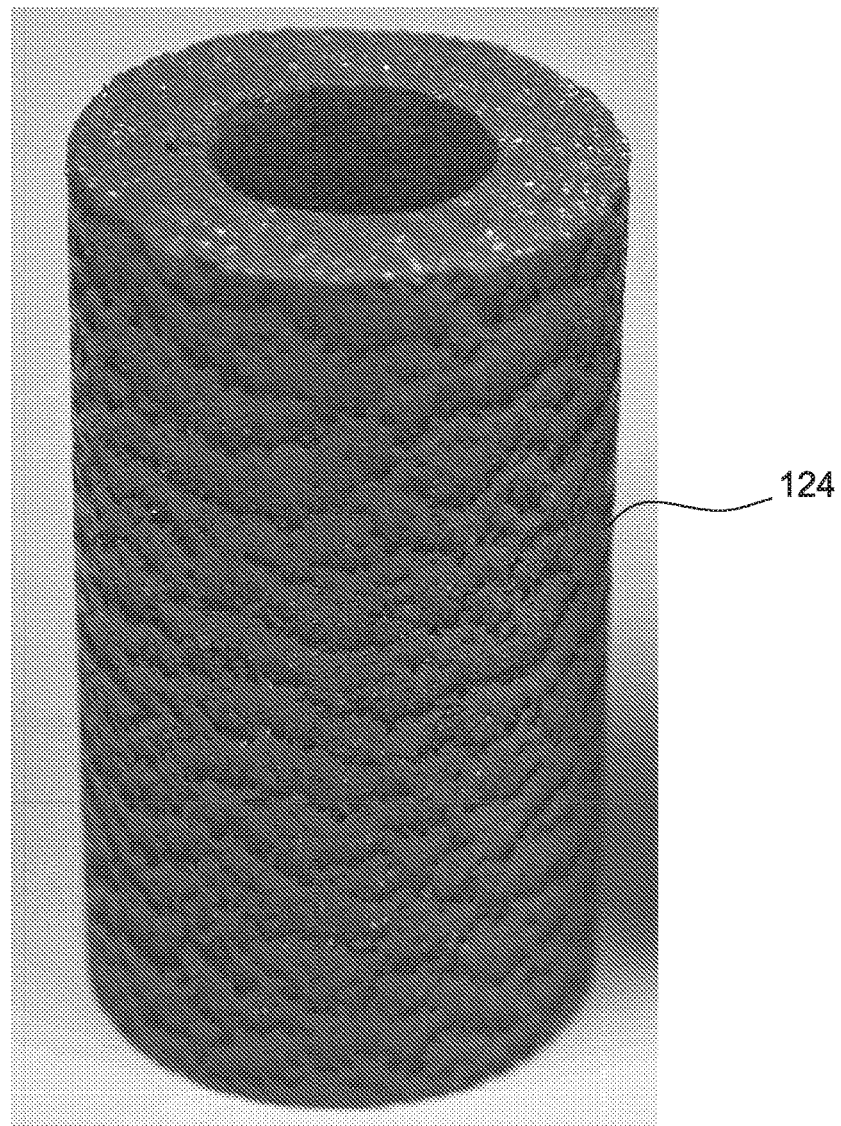
FIG. 16 shows a sample of an extruded conductive bait matrix 123 with structurally inhomogeneous surface prior to exposure to pests.

FIG. 16 shows a conductive bait matrix 123 according to the invention with a structurally inhomogeneous surface.

In one embodiment of the invention, one or more of the parameters of the extrusion process like for example temperature, duration, extrusion velocity, extrusion additives, post-extrusion treatment and the like are chosen so that the surface of the extruded workpiece comprises separated or interconnected cavities of 0.1 mm to 20 mm width and 0.1 mm to 5 mm depth.

The skilled person is knowledgeable as to which parameters of the extrusion process produce imperfect/structurally inhomogeneous surfaces of a workpiece. For example a structurally inhomogeneous surface can be produced by applying extrusion temperatures of at most $T_m+80°$ C. or $T_m+70°$ C. or $T_m+60°$ C., $T_m$ being the extruded thermoplastic semicrystalline polymer's melting temperature.

The cooling can be achieved, for example, by applying a water bath to the workpiece or by spraying the workpiece with water.

In another embodiment of the invention, the surface of the finished workpiece is structurally homogeneous, i.e. does show few or no cavities in the mm to cm scale.

Figure 4:
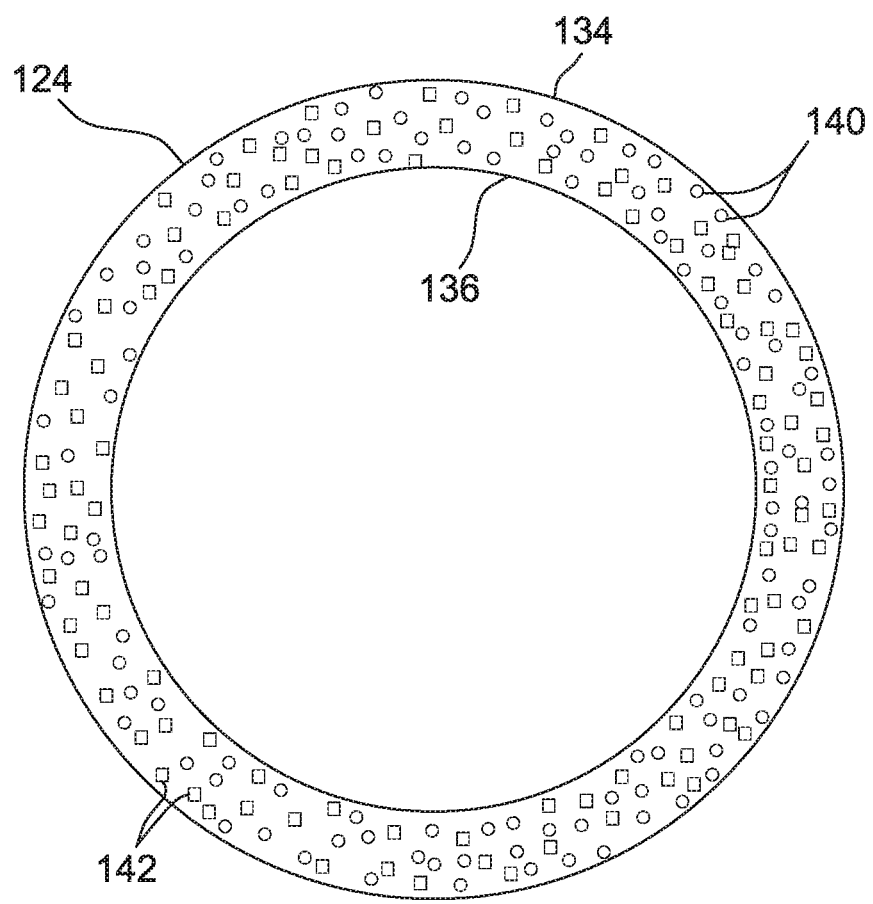
FIG. 4 is a schematic lateral or transverse cross-section of a bait matrix of the bait station of FIG. 2 prior to consumption.

FIG. 4 is a cross-section of the bait matrix 124. As is readily seen, the electrically conductive particles (illustrated schematically as circles 140) and carrier material particles (illustrated schematically as squares 142) are randomly interspersed throughout both the thickness and the height of the bait matrix 124.

In some embodiments, the bait matrix 124 includes an electrically conductive bus member secured thereto, such as by being molded with the bait matrix 124 or thermally secured thereto so that the bus member is held at least in part within the bait matrix 124. In other embodiments the conductive bus member is attached to the bait matrix 124 by suitable attachment techniques. As used herein, a "bus member" refers to a bulk (or non-particle) member having a predetermined disposition (or orderly arrangement) in or on the bait matrix 124 to facilitate enhancing an electrical property of the bait matrix 124. Notably, the bus member may suitably be made continuous or discontinuous without departing from the scope of this invention.

In other contemplated embodiments, the bait matrix 124 may be made by first forming the bait matrix 124 exclusively from electrically non-conductive material. Once the bait matrix 124 is formed, a coating of electrically conductive material is applied to the surface, preferably to the outer surface of the bait matrix 124. For example, in one embodiment where the bait matrix 124 is generally tubular, the bait matrix 124 has opposite end surfaces that are coated with electrically conductive material, e.g., by sputtering, spraying, printing, and/or dipping processes. The coating may be applied at a suitable thickness in a substantially uniform manner or in a suitable pattern.

Figure 5:
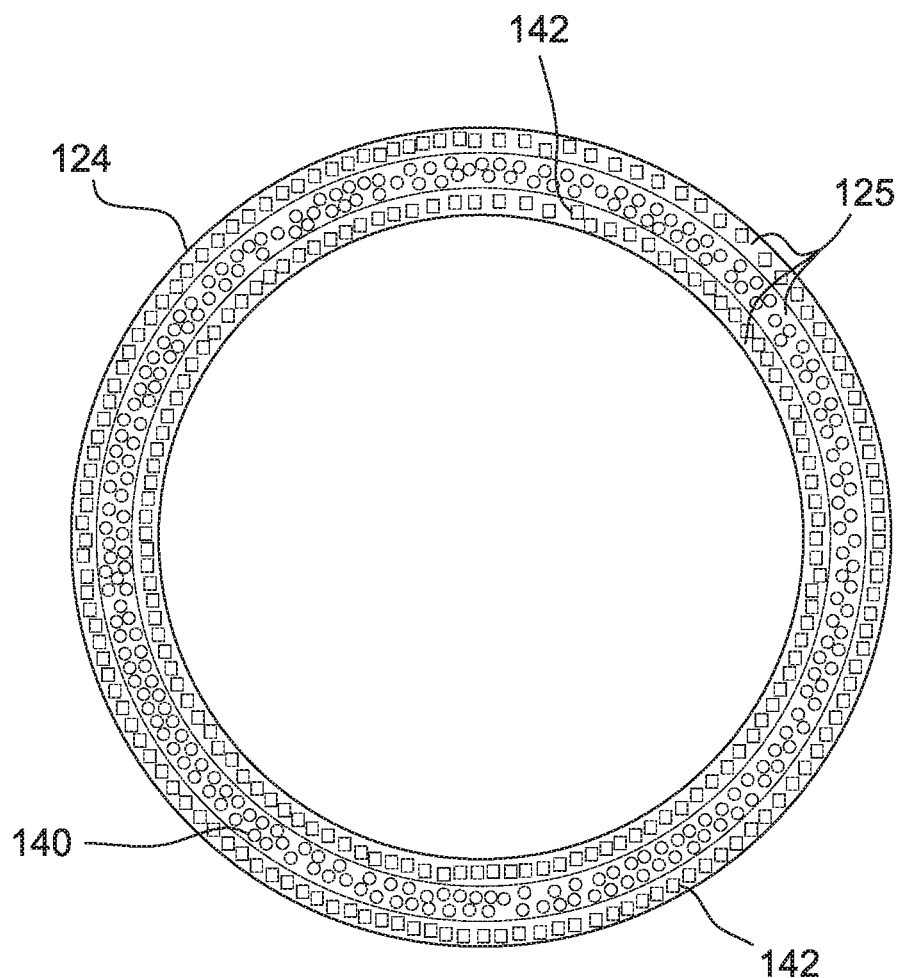
FIG. 5 is a schematic lateral or transverse cross-section of another embodiment of a bait matrix for use in the bait station of FIG. 2 prior to consumption.

As shown in FIG. 5, in another contemplated embodiment of the bait matrix 124, the bait matrix 124 may be formed by a process of co-extrusion such that the bait matrix 124 has a plurality of distinct layers 125. In such an embodiment, a layer of electrically conductive particles 140 would be extruded simultaneous to a layer of carrier material particles 142 such that the layer of carrier material particles 142 cover an outer surface of the layer of electrically conductive particles 140. Optionally, the layer of electrically conductive particles 140 may be sandwiched between layers of carrier material particles 142.

Referring back to FIGS. 2 and 3, in the illustrated embodiment the electrode assembly 126 includes a first electrode 144 and a second electrode 148. The conductive bait matrix 123 is sandwiched between the electrodes 144, 148 such that the first end surface 130 is placed in electrical contact with the first electrode 144, and such that the second end surface 132 is placed in electrical contact with the second electrode 148. In one embodiment, the electrodes 144, 148 are made of a suitable conductive material (e.g. copper) and are generally plate-shaped (e.g., the electrodes 144, 148 may be generally disc-shaped such that the sensor assembly 108 as a whole has a generally cylindrical shape, as shown in FIG. 3). In other embodiments, the electrodes 144, 148 may be made of any suitable material and may have any suitable shape that enable the electrode assembly 126 to function as described herein (e.g., the electrodes 144, 148 may each have a suitable protective and/or electrically conductive coating deposited over the metal material, at the interface between the electrodes 144, 148 and the bait substance 124).

In the illustrated embodiment, the sensor holder 110 includes a pair of electrode covers, namely a first electrode cover 146 and a second electrode cover 150. The covers 146, 150 are made of an electrically insulating material (e.g., a rubber or plastic material) and facilitate isolating the electrodes 144, 148, respectively, from contacting any applicable station housing or other surrounding structure. While the electrode covers 146, 150 are illustrated as overlying only the outer end faces 152, 154 of the electrodes 144, 148, respectively, it is contemplated that in other embodiments the electrode covers 146, 150 may be configured to overlay any suitable surface(s) of the electrodes 144, 148 that facilitates enabling the electrodes 144, 148 to function as described herein.

In the illustrated embodiment, the control unit 128 is disposed at least in part within a hollow compartment 138 of the first cover 146. The control unit 128 is configured to supply the electrode assembly 126, and hence the conductive bait matrix 123, with electrical current. The control unit 128 may also be operable to transmit, in a wired or wireless manner, signal(s) indicative of at least one electrical characteristic of the conductive bait matrix 123 (e.g., the resistance, capacitance, and/or impedance of the conductive bait matrix 123) to the data collection system 104.

The control unit 128 may include any suitable processor-based device (e.g., a microcontroller with associated memory on which executable instructions are stored), or any suitable configuration of a reduced instruction set circuit(s) (RISC), an application-specific integrated circuit(s) (ASICs), and/or a logic circuit(s). Alternatively, the control unit 128 may suitably include any circuit and/or processor that is capable of executing the functions of the control unit 128 as described herein.

Figure 15:
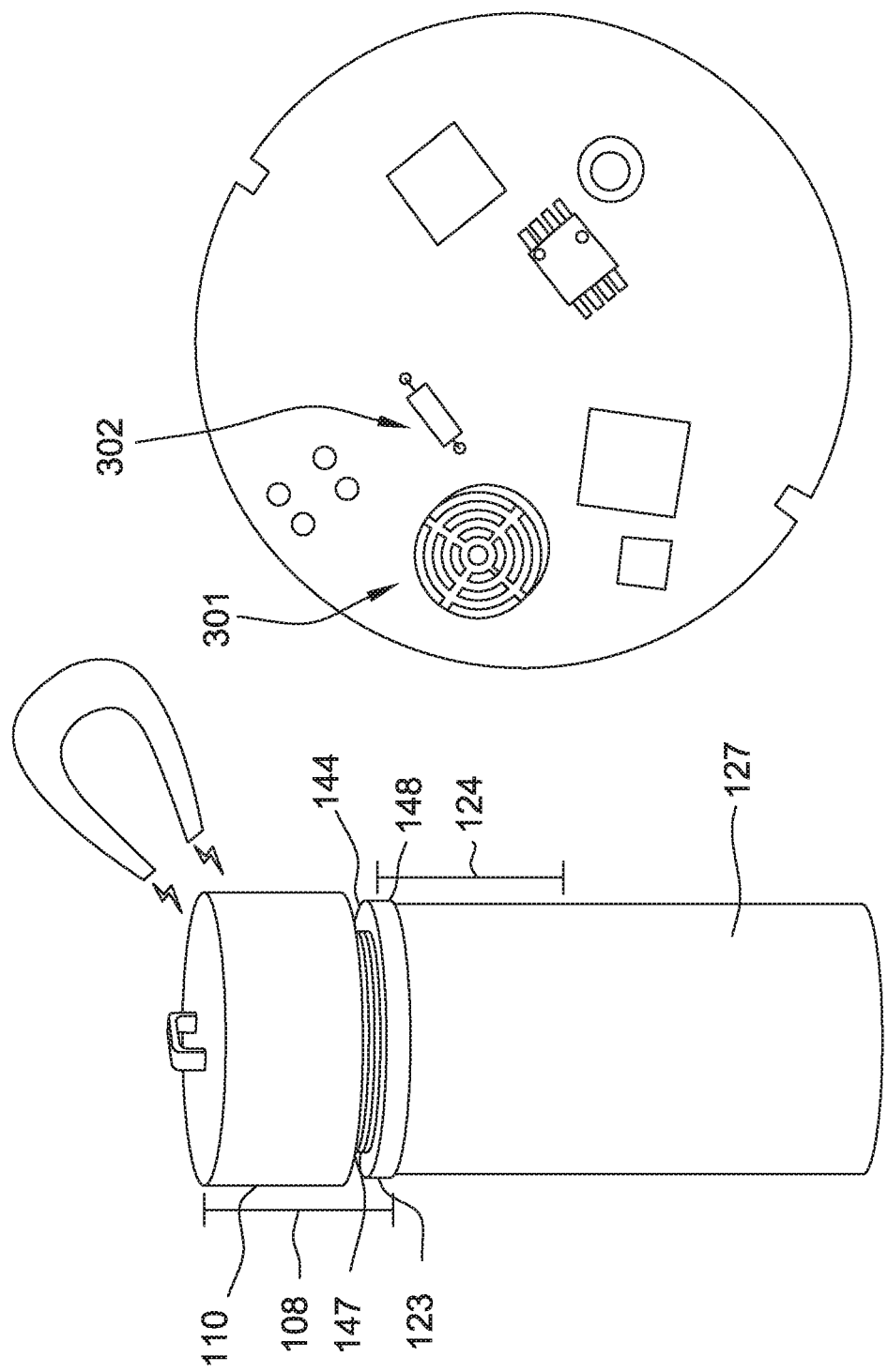
FIG. 15 is an illustration of a past control or detection system 100 using a magnet to activate the magnetic reed switch on a data collection system 104 also comprising an ultrasonic switch.

As shown in FIG. 15, the control unit may also include one or more switches that are capable of turning on, waking up, resetting or initiating other such functions by the bait stations 102 and/or the data collection system 104. Such switches may include magnetic switches, RF switches, ultrasonic switches, manual switches or any other such type of switch that one may choose to add. A passive and/or proximity type switch may be preferred to an active and/or manual type switch given the possible subterranean location of the pest control and/or detection system 100, such as magnetic reed, inductive and capacitive, seismic, infrared, photographic, thermal, electrical field, chemical, and/or ultrasonic switches, etc. . . . .

Optionally, the control unit 128 may also include a suitable power supply (not shown) (e.g., an electrochemical cell) suitably disposed within the hollow compartment 138 of the first cover 146 for powering the control unit 128, and/or for supplying the electrode assembly 126 (and hence the conductive bait matrix 123) with electrical current via a suitable network of wires. The power supply may also be located remotely from the bait station 102 and may be electrically connected to the control unit 128 and/or the electrode assembly 126 in any suitable manner (e.g., a plurality of aboveground or underground terminals may be accessible on the exterior of the bait station 102 for selectively connecting the remote power supply and/or the data collection system 104 to the control unit 128 and/or the electrode assembly 126 via the terminals).

To assemble the bait station 102, the control unit 128 and any associated power supply may suitably be stowed within the hollow compartment 138 of the top cover 146. The conductive bait matrix 123 is then electrically connected to the electrodes 144, 148, and the control unit 128 is operatively connected to the electrodes 144, 148 in a manner that enables the control unit 128 to selectively supply the electrodes 144, 148 with electrical current. Thus, the conductive bait matrix 123 is situated between the electrodes 144, 148, with the first end surface 130 of the bait matrix 124 in electrical contact with the first electrode 144, and the second end surface 132 of the bait matrix in electrical contact with the second electrode 148. It is to be understood that an external power supply may be provided.

Suitably, the sensor assembly 108 may have an apparatus that clamps the conductive bait matrix 123 between the electrodes 144, 148. For example, in the illustrated embodiment, the sensor holder 110 has a core housing 145 which is formed integrally with the first cover 146 and may extend through the conductive bait matrix 123 for suitable connection (e.g., bolted connection) with the second cover 150. In this manner, the conductive bait matrix 123 is retained between the first cover 146 and the second cover 150 of the sensor holder 110. Optionally, the sensor holder 110 may also be provided with a biasing element 147 for urging the first electrode 144 toward the second electrode 148 to maintain electrical contact between the electrodes 144, 148 and the conductive bait matrix 123 during deployment.

Alternatively, the sensor assembly 108 may have any suitable mechanism that facilitates retaining the bait matrix 124 in electrical contact with the electrode assembly 126.

Once the sensor assembly 108 is assembled, it is able to be deployed without containment in a station housing, or may be suitably inserted into a station housing (not shown) which contains at least a portion of the sensor assembly 108 within the station housing. The station housing may be at least partially to completely underground on a site where termite activity is possible, is suspected, or has been detected. Without the use of a station housing, the sensor assembly 108 is to be suitably buried at least partially underground on a site where termite activity is possible, is suspected, or has been detected. On the other hand, the illustrated embodiment of the sensor assembly 108 and/or its station housing may be suitably configured for deployment aboveground to facilitate detecting, deterring, and/or eradicating any suitable type of pest in any suitable manner. For example, the sensor assembly 108 and/or its station housing may be configured for suitable aboveground deployment on the side of a building, on a pole, on a tree, or at other suitable above ground locations.

After the bait station 102 has been deployed, the control unit 128 is operable to supply the electrodes 144, 148 (and hence the conductive bait matrix 123) with an electrical current. While, or after, current is passed through the conductive bait matrix 123, the control unit 128 is operable to transmit signals indicative of an electrical characteristic of the conductive bait matrix 123 to the data collection system 104. Notably, because the distribution of the electrically conductive particles within the bait matrix may not be predetermined (e.g., because the electrically conductive particles 140 (FIG. 4) are randomly interspersed within the bait matrix), the continuous pathway for electrical current through the conductive bait matrix 123 from the first electrode 144 to the second electrode 148 is, likewise, substantially random. In other words, for each comparable pair of conductive bait matrices 123, while both matrices are made to exhibit similar electrical properties (e.g., similar levels of resistance, capacitance, and/or impedance), the pathway for electrical current through the first one of the conductive bait matrices 123 will in general be different (and unpredictable) relative to the pathway for electrical current through the second one of the conductive bait matrices 123.

In one embodiment, the control unit 128 may be configured for autonomous operation, in the sense that it is configured for automatic (e.g., scheduled, intermittent) supplying of the electrodes 144, 148 with electrical current, and automatic (e.g., scheduled) transmitting of associated signals to the data collection system 104. In another embodiment, the control unit 128 may be configured for subservient operation under the direction of a suitable remote control system, in the sense that the control unit 128 may be configured to supply the electrodes 144, 148 with electrical current and/or to transmit associated signals to the data collection system 104 only when instructed to do so by the remote control system. As such, some embodiments of the control unit 128 may transmit signals to the data collection system 104 in real time (e.g., almost immediately after each pulse of electrical current is supplied to the bait substance 124), or other embodiments of the control unit 128 may record events in its memory for transmitting batch-type signals to the data collection system 104 when scheduled or instructed to do so.

While the control unit 128 of the illustrated embodiment is operable to energize the conductive bait matrix 123 via electrical current supplied to the electrodes 144, 148, it is contemplated that in other embodiments the control unit may energize the conductive bait matrix 123 with direct electrical communication with the bait matrix, such as by applying microwave energy or other suitable energy to the conductive bait matrix 123.

Figure 6:
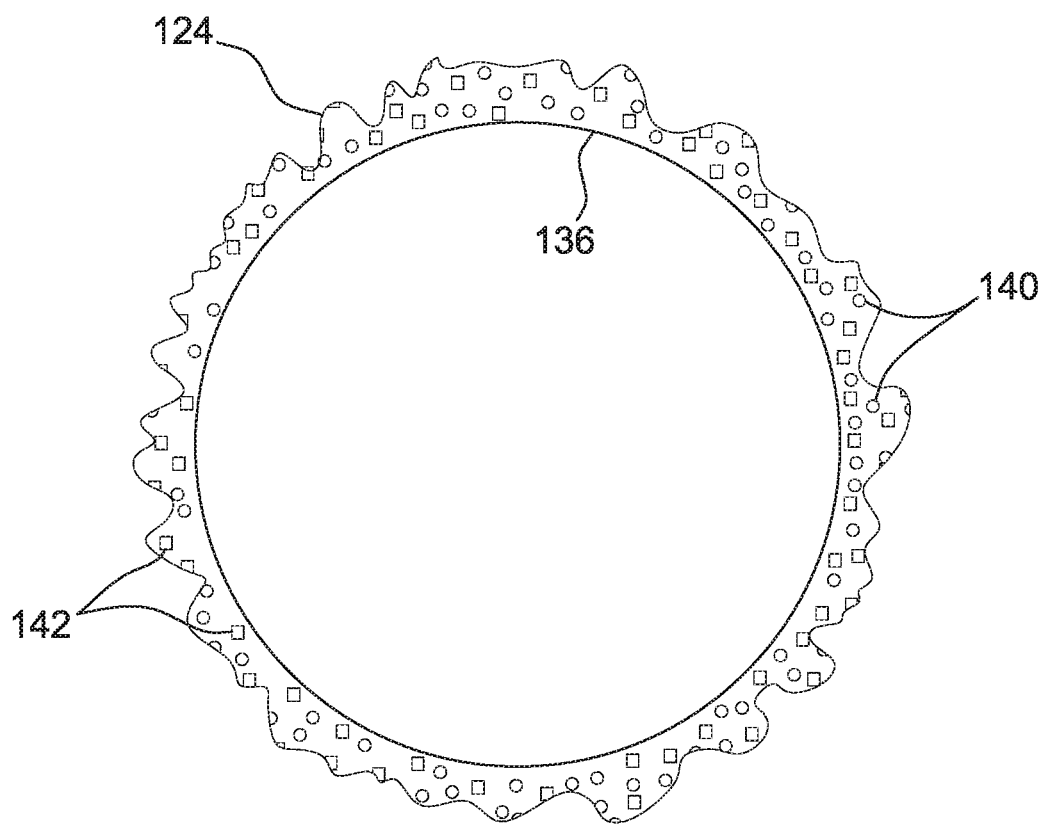
FIG. 6 is a schematic cross-section of the bait matrix embodiment shown in FIG. 4 after portions of the bait matrix have been consumed or otherwise depleted.
Figure 7:
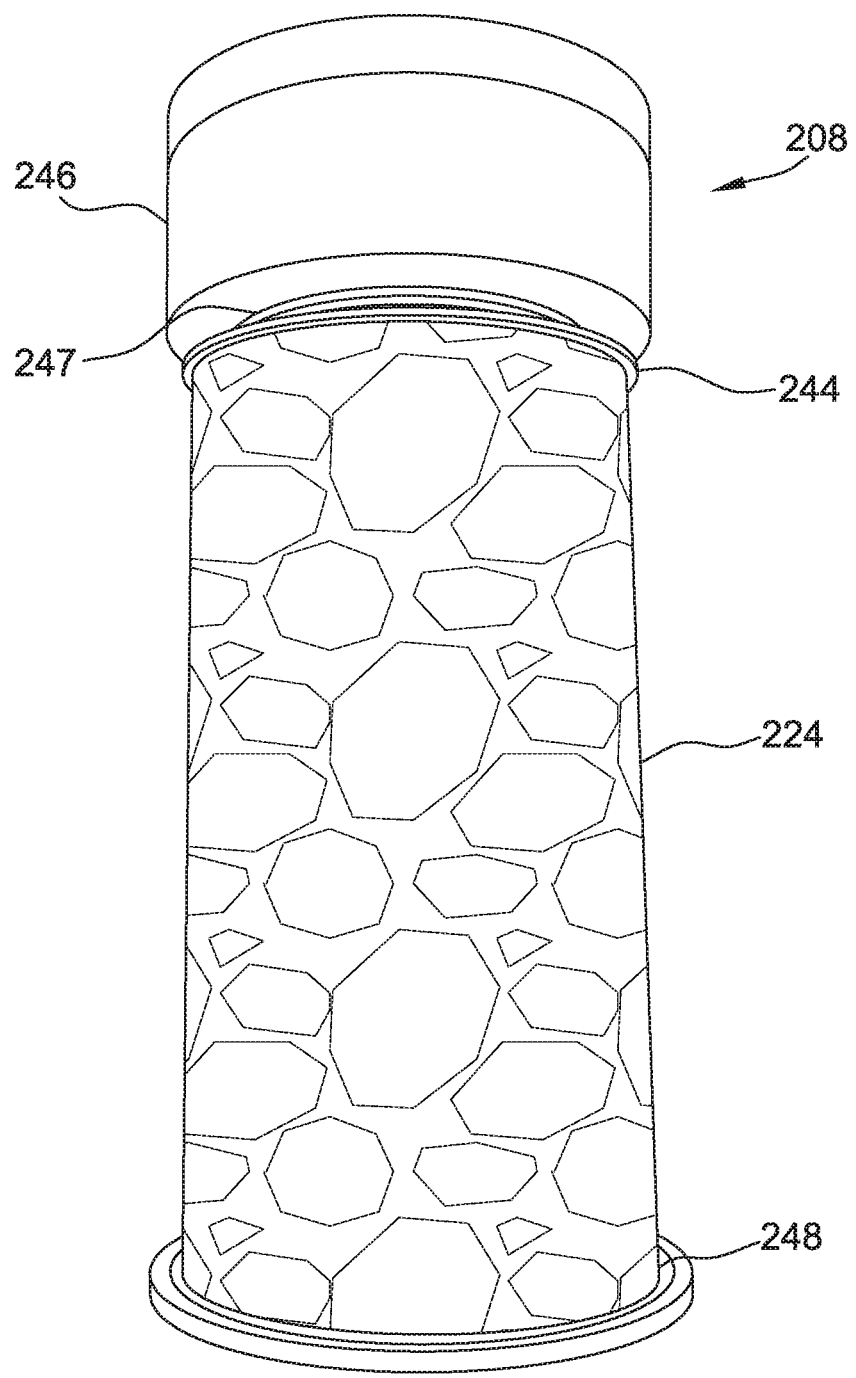
FIG. 7 is a side elevation of a second embodiment of a pest control and/or detection system.
Figure 8:
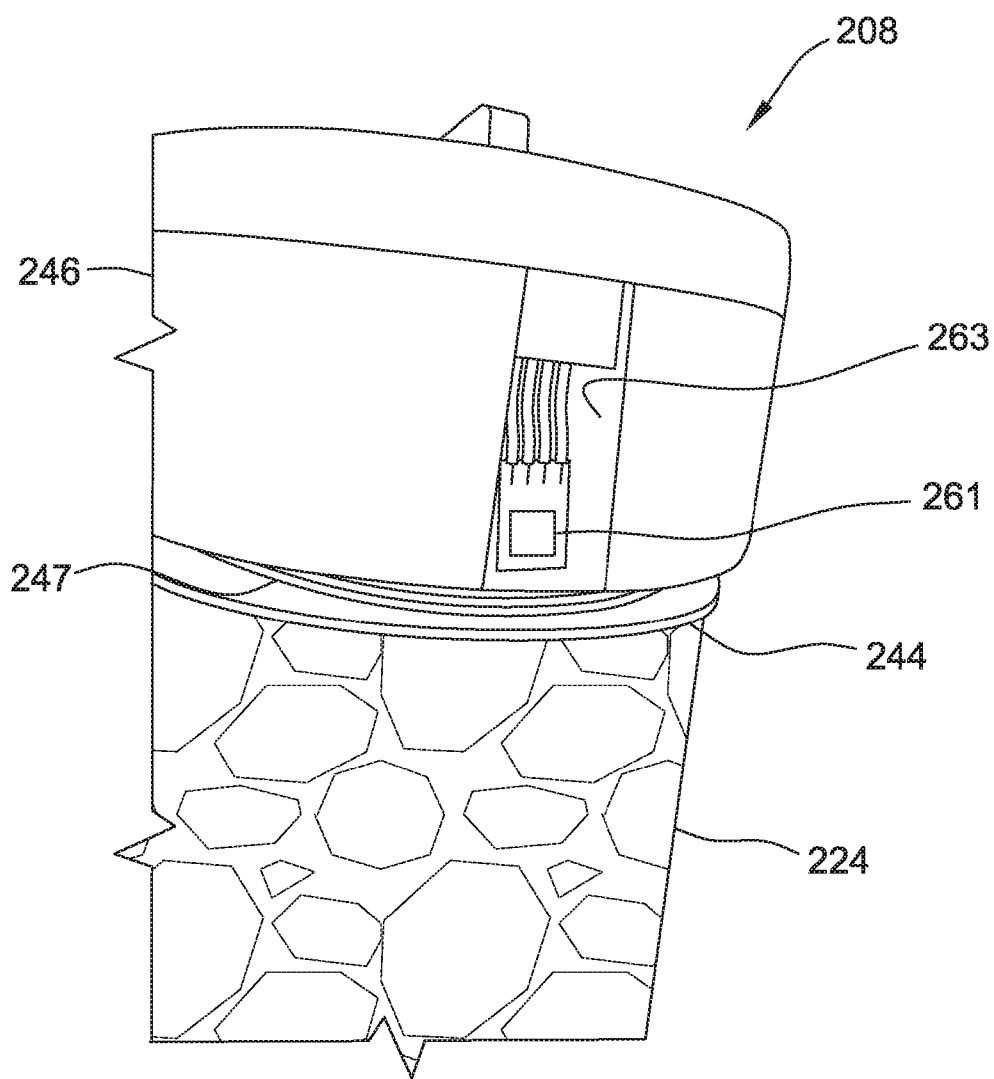
FIG. 8 is an enlarged side perspective of a portion of the pest control and/or detection system of FIG. 7.
Figure 9:
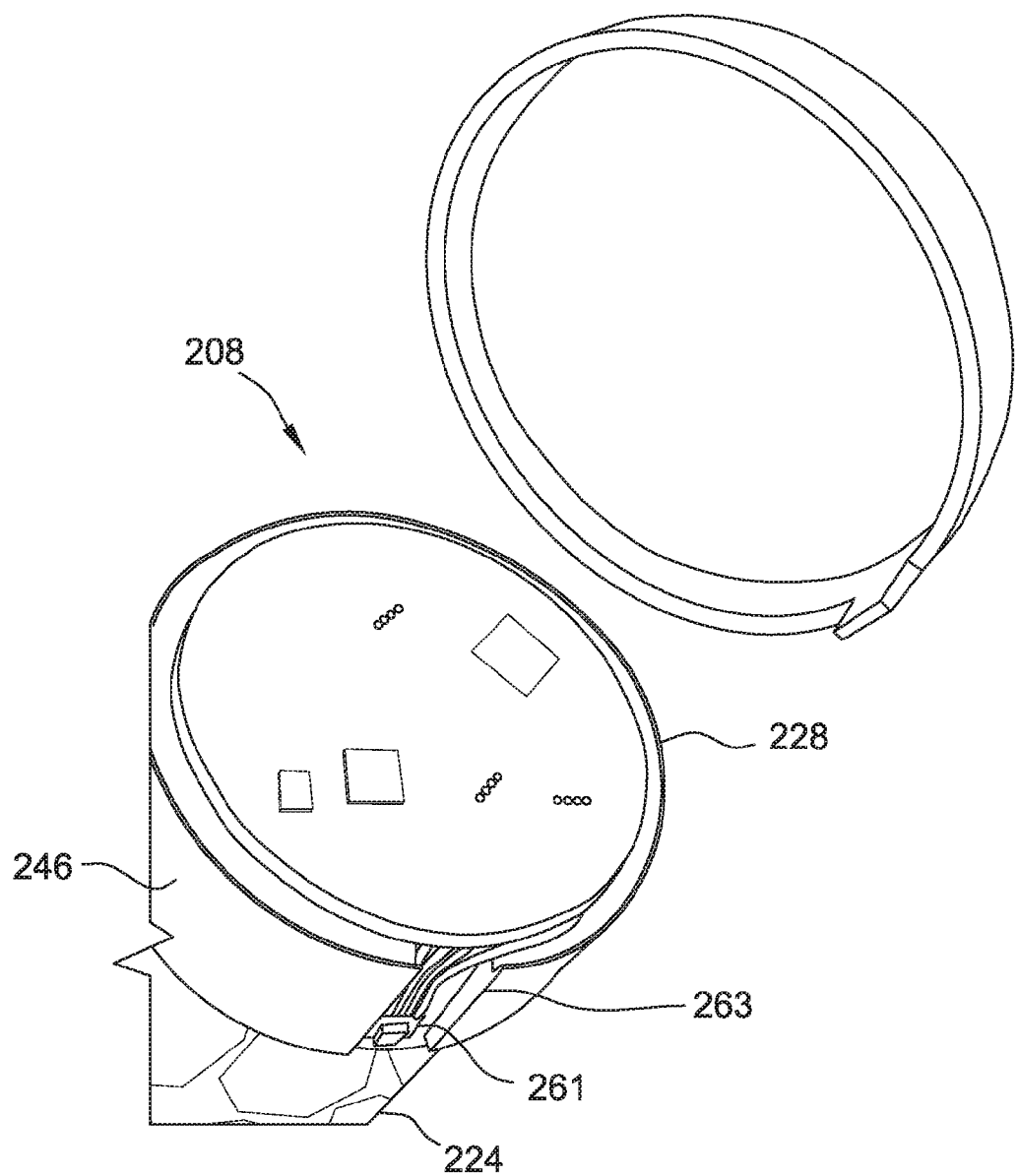
FIG. 9 is an enlarged top perspective of a portion of the pest control and/or detection system of FIG. 7, with a component removed to reveal internal construction.

When the illustrated embodiment of the sensor assembly 108 is deployed, the carrier material and more particularly the carrier material particles 142 of the bait matrix 124 may be detected by termites and found palatable to the termites. As termites chew on the bait matrix 124, they remove (e.g., such as by consuming or displacing) particles from the bait matrix 124 (as illustrated by the uneaten bait matrix 124 of FIG. 4 having been chewed/displaced in the manner shown in FIG. 6 and/or FIG. 16a image (b)). Some particles may be disseminated throughout their colony, feeding and/or foraging area.

As material is removed from or displaced within the bait matrix 124, at least some of the electrically conductive particles 140 are removed from or displaced within the conductive bait matrix 123. As electrically conductive particles 140 are removed or displaced, at least one electrical characteristic of the conductive bait matrix 123 (e.g., its conductivity, its resistance, capacitance, and/or impedance) is changed. That is, as the mass of the conductive bait matrix 123 decreases (e.g., as the thickness of the bait matrix 124 from the radially inner surface 136 outward decreases), at least one electrical characteristic of the conductive bait matrix 123 changes. For example, the electrical resistance through the conductive bait matrix 123 will increase as material is removed from the bait matrix.

In the illustrated embodiment, with each pulse of current supplied to the conductive bait matrix 123 via the electrodes 144, 148, the control unit 128 transmits a signal to the data collection system 104, and the signal is indicative of at least one electrical characteristic of the conductive bait matrix 123. In this manner, the data collection system 104 is configured to associate each signal received from the control unit 128 into a quantitative measurement as to at least one electrical characteristic of the conductive bait matrix 123. Using this determined electrical characteristic, a quantitative measurement as to how much of the conductive bait matrix 123 has been removed by the termites may be determined. It is to be understood that a characteristic of the conductive bait matrix 123 is transmitted and that the conductive bait matrix 123 may be electrically conductive and or conductive by other means. In some instances, to facilitate taking into account the environment of the bait matrix 124 and improving the accuracy of the bait depletion measurement, the control unit 128 may also transmit to the data collection system 104 signals indicative of the historical and/or instantaneous temperature and/or moisture content of the bait matrix 124.

It is contemplated that the control unit 128 may transmit signals indicative of other suitable properties of the bait matrix 124 as well. Moreover, all such properties of the bait matrix 124 and its environment may be utilized by the control unit 128 and/or the data collection system 104 to create predictive models or indicator models through which pest advisories can be provided to the property owner.

In this manner, using the signals received from the control unit 128, the data collection system 104 logs and/or monitors changes to the mass of the conductive bait matrix 123. In one embodiment, the data collection system 104 compares the at least one electrical characteristic of the conductive bait matrix 123, and/or the mass of the conductive bait matrix 123 to a threshold value. Upon meeting or exceeding the threshold value, the data collection system 104 generates a warning (e.g., a message sent to a monitoring entity) that the bait station 102 is in need of inspection, baiting of the station with a toxicant, replacement of the sensor assembly 108 (or simply the bait matrix 124, conductive bait matrix 123 and/or non-conductive bait matrix 127) and/or other appropriate action.

Figure 22:
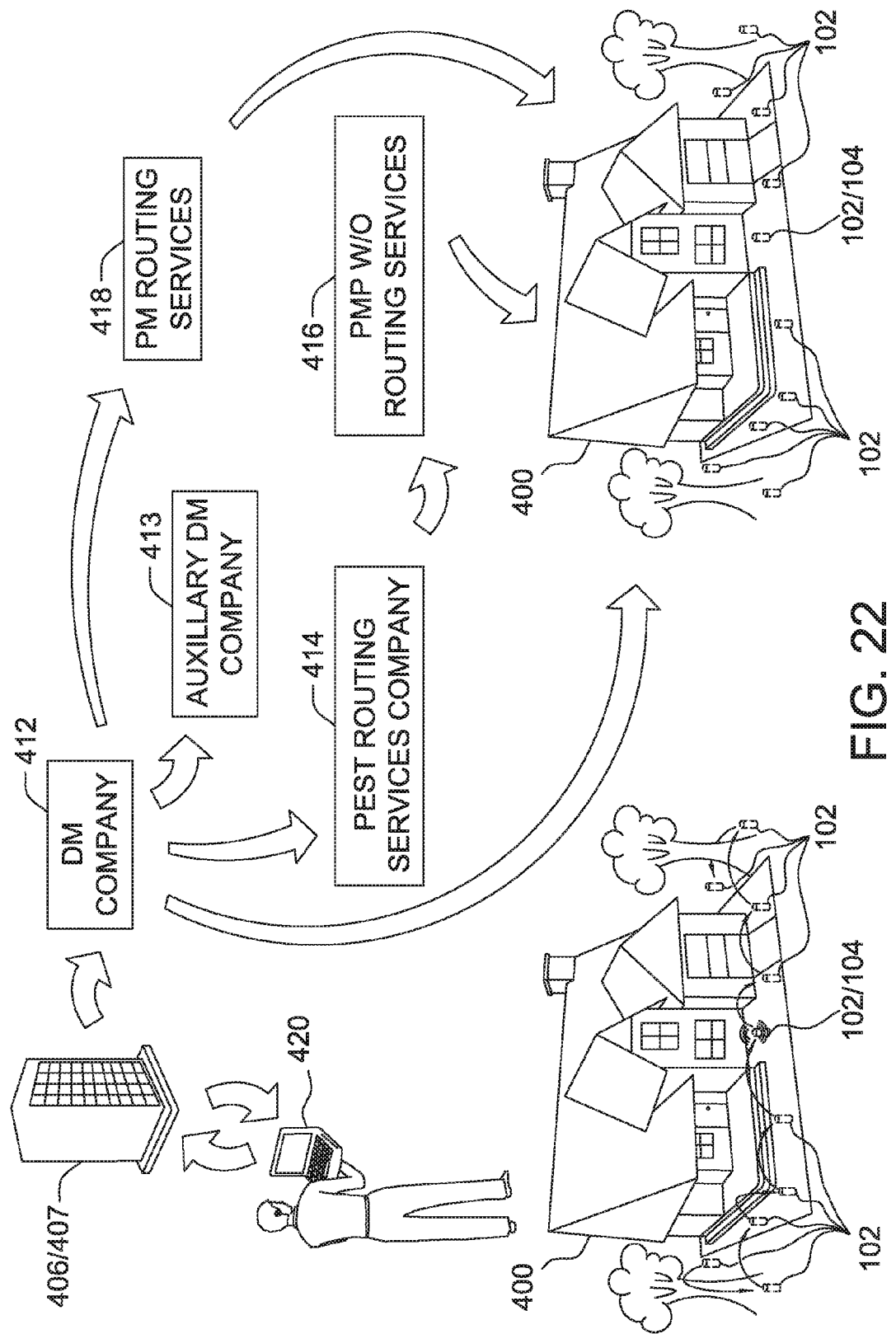
FIG. 22 shows another example of a data communication pathway comprising an On-site inspection using a mobile device as the communication Portal 404 to communicate with gateway 104 to collect reporter 102 sensor data and interact with distributed network 408; a technician at non-programmed time intervals activates gateway 104 using a ultrasonic switch which then transmits pest monitoring/detection data received from stations 102 to technician's mobile device 420; data can then be transmitted to distributed network system/cloud hosted by Home Security Company Data Services 406 or Cloud Services Network provider 407; Data analysis can either be done by Data Management Company 412 and/or by Technician's mobile device 420 itself; Technician's mobile device 420 functions as the Communication Portal 404.

In other embodiments, the data collection system 104 may intermittently monitor the mass of the conductive bait matrix 123 without regard to a threshold. For example, a technician may monitor the mass of the conductive bait matrix 123 daily, weekly, monthly, bi-annularly or other suitable time period to intermittently assess what actions need to be taken for a particular bait station 102 (FIG. 22). In this manner, the pest control and/or detection system 100 facilitates continuously monitoring the status of the bait substance 124, thereby enabling more proactive and/or timely detection of pest activity and corrective action in the case of the presence of pests.

Figure 10:
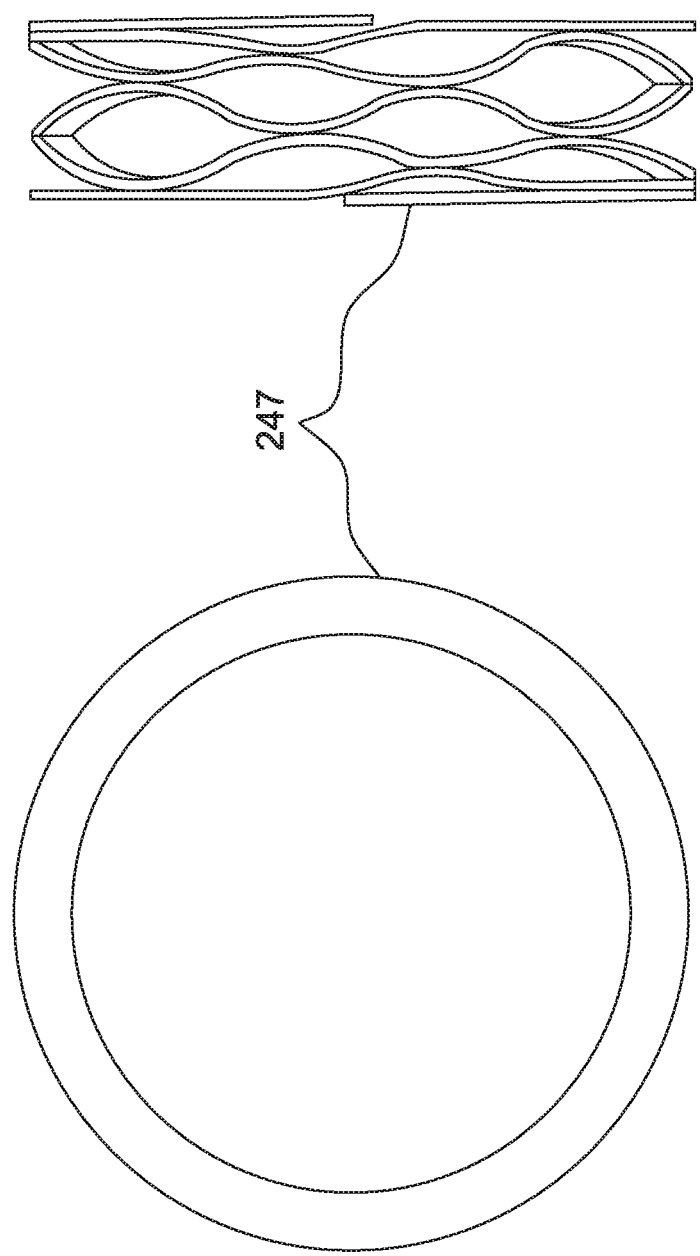
FIG. 10 is a schematic top and front view of a wave spring for use with the pest control and/or detection system of FIG. 7.

FIGS. 7-10 illustrate another embodiment of a sensor assembly 208 that is substantially similar in construction to the sensor assembly 108 of the embodiment of FIGS. 2 and 3. In this embodiment, however, a biasing element 247 is axially (e.g., concentrically in the illustrated embodiment) disposed and compressed between the cover 246 and the first electrode 244 for urging the first electrode 244 down against the top of the bait matrix 224 and for urging the bait matrix down against the second electrode 248 to maintain electrical contact between the electrodes and the conductive bait matrix 123. The biasing element 247 according to one suitable embodiment is in the form of a wave spring, and more suitably a crest-to-crest wave spring, with plain, or flat wire ends as best seen in FIG. 10.

In this embodiment bait matrix 224 is conductive and does not contain a non-conductive bait matrix 127. Because of the manner in which the bait matrix 224 is formed, it is understood that the bait matrix, including the top and bottom of the bait matrix, may not be smooth (e.g., the surface is rough) and may also not be entirely level. The flat wire ends may facilitate flush, 360 degree contact between the biasing element and the first electrode 244 to provide a uniform current distribution therebetween. The wave spring 247 provides a uniform load distribution between the cover 246 and the first electrode 244 while accounting for any surface irregularities or slight taper (e.g., not perfectly level) of the top of the bait matrix 224.

In the illustrated embodiment of FIG. 10, according to one suitable embodiment the wave spring may have a free height of about 0.421 inches, a wire thickness of about 0.012 inches, and 4 active turns (6 total turns including the flat wire ends). The radial width of the wire is in the range of about 0.139 inches to about 0.147 inches. The wave spring 247 is constructed so that its working (e.g., compression) height is about 0.151 inches under a load of about 6.7 to about 8.3 pounds. It is understood that other suitable wave spring dimensions may be used without departing from the scope of this invention.

It is also contemplated that a suitable conductive grease (not shown), such as a carbon conductive grease, may be used between the first electrode 244 and the top of the bait matrix 224 and/or between the second electrode 248 and the bottom of the bait matrix to further account for the irregular surfaces of the top and bottom of the matrix.

The sensor assembly 208 in accordance with one embodiment may further comprise one or more environmental sensors 261 for sensing one or more characteristics of the ambient environment in which the sensor assembly is placed—e.g., within the station housing below ground, directly below ground without a station housing, or any above-ground location (e.g., within a residential or commercial structure). In one particularly suitable embodiment the one or more environmental sensors 261 may comprise one or more moisture sensors for sensing the moisture surrounding the sensor assembly 208. In the illustrated embodiment, the cover 246 includes a window 263 and the environmental (e.g., moisture) sensor 261 is disposed within the cover 246 at the window so that the sensor is openly exposed to the environment surrounding the sensor assembly. In other embodiments the one or more environmental sensors 261 may instead or additionally comprise a temperature sensor.

Moisture or other environmental conditions impact the signals that are indicative of the electrical characteristic (e.g., resistance, capacitance, etc.) of the conductive bait matrix 123. As a result, the signals transmitted by the control unit 228 to the data collection system 104 may not accurately reflect the actual change in electrical characteristic resulting from pests consuming the conductive bait matrix 123. To this end, the one or more environmental sensors 261 generate a signal indicative of the at least one environmental characteristic.

In one embodiment, the signal indicative of the at least one environmental characteristic is transmitted to the data collection system 104 along with the signal indicative of the electrical characteristic. A processor at the data collection system 104 adjusts the electrical characteristic signal as a function of the environmental characteristic signal and then uses the adjusted electrical characteristic signal to determine the electrical characteristic (e.g., resistance, capacitance, impedance). In other suitable embodiments the processor may first determine the electrical resistance as a function of the environmental characteristic signal and then adjust the determined electrical resistance as a function of the environmental characteristic signal. In still other embodiments, it is contemplated that the control unit 228 of the sensor assembly 208 may include a processor that adjusts the electrical characteristic signal as a function of the environmental characteristic signal and then transmits the adjusted electrical characteristic signal to the data collection system 104.

In yet another embodiment of the invention, the pest control and/or detection system may preferably use a magnetic reed switch 302 to wake-up, turn on, and/or reset the one or more bait stations 102 and/or the one or more data collection systems 104. The magnetic reed switch 302 as shown in FIG. 15 may supply power to the circuit board. Given that the pest control and/or detection system may be located in a subsurface environment the magnetic reed switch 302 provides various advantages such as, it is a locking switch, it uses less power than other options such as an ultrasonic switch, and it may be internally located allowing for a more secure sealed housing around it.

Prior to the magnetic reed switch 302 being activated the one or more bait stations 102 and/or the one or more data collection systems 104 may be in a sleeping state or turned-off state to preserve energy. Once the magnetic reed switch 302 is used to provide power to the one or more bait stations 102 and/or the one or more data collection systems 104, the one or more bait stations 102 are now in discovery mode or administration mode and able to search for the one or more data collection systems 104. It is to be understood that another type of switch may be used to wake-up, turn on, and/or reset the one or more bait stations 102 and/or the one or more data collection systems 104.

Figure 13:
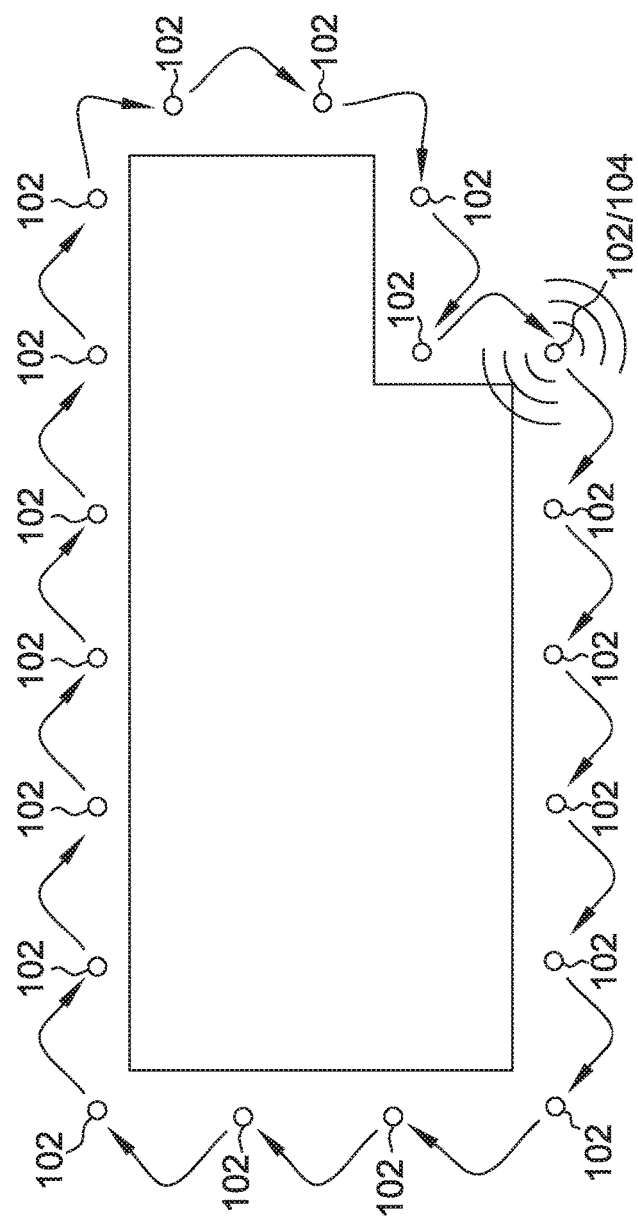
FIG. 13 is an illustration showing one example of the functionality of the mesh network communicating from bait stations 102 to a data collection system 104 and the data collection system 104 then transmitting the data to an external source.

One or more bait stations 102 joining the data collection system 104 may form a mesh network as shown in FIGS. 13 and 14. The mesh network allows the bait stations 102 to send information/data, such as data related to a characteristic of the conductive bait matrix 123, through each other to get to the one or more data collection systems 104. This allows the bait stations 102 further away from the data collection systems 104 to still transmit data to the data collection systems 104 so long as they are close enough to one or more bait stations 102 within the mesh network. Preferably the one or more bait stations 102 do not have electronic addresses or MAC IDs and will not need to be entered into the system. Rather using magnetic reed switch 302 to reset or turn on the bait station 102 and or swiping a magnet over the sensor assembly 108 while in the vicinity of a data collection system 104 that is set to a maintenance or administration mode will allow the bait stations 102 to search for and connect to the data collection system's 104 mesh network. Bait stations 102 have the ability to determine a reset from activation of the magnetic switch or a self-induced (warm) reset. This enables the bait stations 102 to place themselves in a known state for each mesh update period while retaining memory. The bait stations 102 may be in a stateless state, wherein they have no knowledge of the data collection system's 104 IP address. The bait stations 102 may send out data and may not know that they are reporting in a network or who is receiving the data packets they send out. A warm reset means that the circuit is alive at the time of the reset. A warm reset may be used to collect data from the data collection system 104 using a remote device as explained in more detail below.

Figure 14:
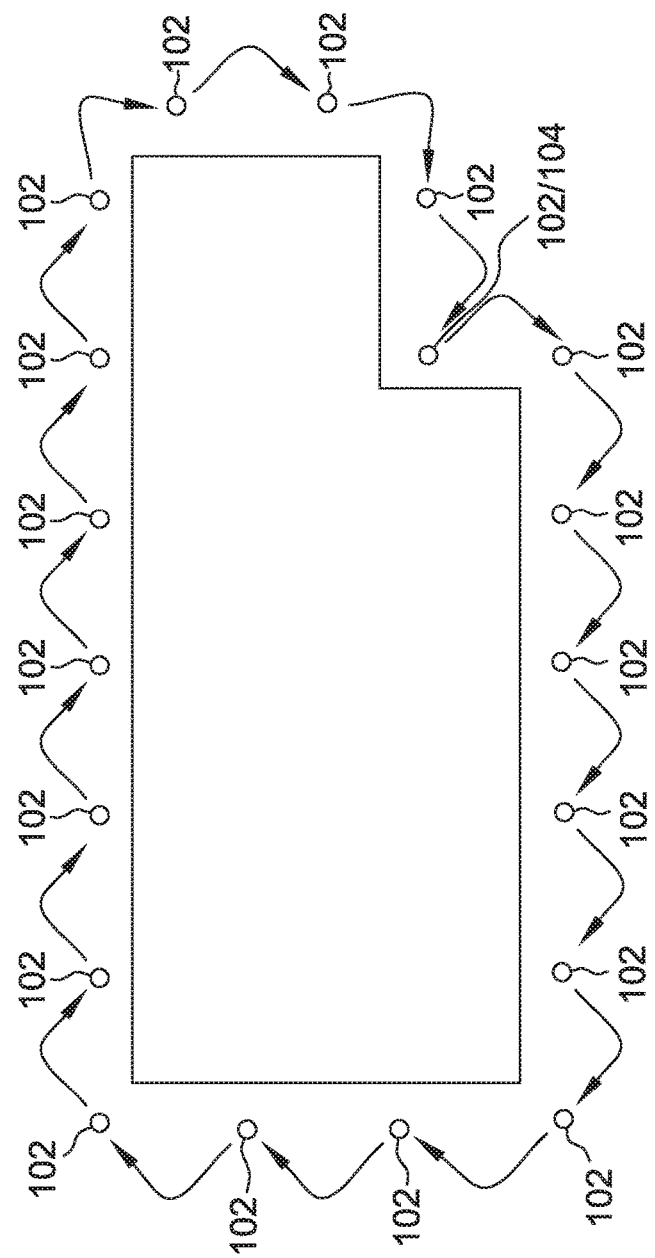
FIG. 14 is an illustration showing one example of the functionality of the mesh network communicating from bait stations 102 to a data collection system 104 and the data collection system 104.

The mesh network is based on the International Engineering Task Force (IETF) RFC6202 "Trickle algorithm", which is a type of flood control algorithm for lossy, low-power networks. Adjusting the transmission window allows the Trickle algorithm to spread new information. It is to be understood that other algorithms may be used to create a mesh network so long that they allow the data to pass along the chain of bait stations 102 as shown in FIGS. 13 and 14 until reaching the data collection system 104.

The mesh network may communicate using IEEE 802.15.4. However, it is to be understood that other forms of communication between the bait stations 102 and the data collection systems 104 within the mesh system may be used. IEEE 802.15.4 is a radio platform that may handle the data transmission within the mesh network. A 2.4-2.5 GHz frequency ISM band may be used to establish bait station 102-to-bait station 102 communication and bait station 102-to-data collection systems 104 communication. It is to be understood that other frequencies may also work such as 5.7-5.8 GHz frequency ISM band. It was unexpected given the nature of radio waves to find that the 2.4-2.5 GHz frequency ISM band was effective for the sub-surface data transmission that is a part of the pest control and/or detection system. It was commonly believed that the sub-surface environment would interfere with the ability of the 2.4-2.5 GHz ISM band to transfer data. It was believed that only higher frequencies would be effective for this type of communication/data transmission due to the high level of interference from the subsurface environment. However, for the current application, it has been determined that within the 2.4-2.5 GHz ISM band, the bait stations 102 are able to transmit data to one another and to the data collection system 104. The code that creates the data packages to be transmitted may be separate from the code controlling communication. The synchronization of the bait stations 102 and the data collection system 104 may assist with the ability to communicate in the subsurface environment at this 2.4-2.5 GHz ISM band as well as the type and size of the data packets being transferred. The data being communicated through the mesh network may include whether or not the resistance level of the conductive bait matrix 123 has reached a set threshold level.

The data collection system 104 may communicate (a) internally and/or (b) externally. The data collection system's 104 internal communication may take place using the mesh network. The data collection system's 104 external communication may be sent to a HS Hub 402 and on to a communication portal 404 as shown in FIGS. 13, and 17-22. It is to be understood that the data collection system 104 and HS Hub 402 may use a WiFi connection and/or a cellular connection and/or any other suitable form of communication means to transmit data externally from the data collection system 104 and/or HS Hub 402 and/or the communication portal 404. The HS Hub 402 and/or the communication portal 404 may be provided by a customer using the pest control and/or detection system and/or by any other external source. The HS Hub 402 and/or the communication portal 404 allow for the periodic logging of sensor/network data to the external host cloud. An Application Program Interface (API) may be used to transmit the data from the data collection system 104 to the cloud. An API may be used to transmit the data from the bait station 102 to the data collection system 104. An API may be used to transmit the data from the cloud to a web interface. An API may be written using a variety of different formats such as JSON, XML, or other such text-based formats or binary serialization such as MessagePack, protobuf, bson, avro or any other such binary format.

The data collection system 104 itself may have two different modes when operating a maintenance or administrative mode or discovery mode that allows the data collection system 104 to detect and add bait stations 102 to the network or a reporting mode. When data collection system 104 is set to the administration mode data collection system 104 is searching for bait stations 102 to add to its network and sends out pings to the bait stations 102 it finds. It may be desired to have the data collection system 104 auto default to this mode when it is first activated. Once a bait station 102 is attached to a data collection system 104 network, the bait station 102 will not look to join any other network unless it is told otherwise and/or reset. It is too be understood both the data collection system 104 and the bait stations 102 may need to be set to the administration or discover mode for the network to be created. A mobile app may also be used to set the data collection system 104 into discovery mode. When setting up the pest control and/or detection system 100 the installer may turn on the data collection system 104 first, ensure that it is in administration mode, and then activate the individual bait stations 102 to form the pest control and/or detection system network. It may be preferred that the pest control and/or detection system 100 communicate using a mesh network as described herein.

The data collection system 104 also may have two different communication modes (a) internal communication over the pest control and/or detection system network to send or receive information with the bait stations 102 or (b) external communication to send or receive information with a remote device and/or the cloud. To receive data from the bait stations 102, the data collection system 104 may ping the individual bait stations 102 on its network. The bait stations 102 may respond and may send out data that is not specifically directed to the data collection system 104, but because they are a part of the same network, the data collection system 104 is able to gather all of the data from the individual bait stations 102.

The data collection system 104 may have knowledge of which bait stations 102 belong in its network, while the bait stations 102 themselves do not recognize who specifically it is talking to. The data collection system 104 is configured to store the data sent to it from the bait stations 102 at least until the data is sent to an external location and/or device by the data collection system 104. The data collection system 104 will preferably send the data to the cloud or external source, upon receipt of instructions to do so and/or upon time intervals programmed into the firmware of the bait stations 102 and/or the data collection systems 104. It is to be understood that the data collection system 104 may send data to the cloud and/or external source at programmed time intervals and/or upon request from mobile application used on a remote device as described in more detail below.

It is to be understood that the data collection system 104 may function as both a bait station 102 and/or as a data collection system 104 and may comprise the ability to communicate both internally with the other bait stations 102 and/or data collection systems 104 as well as externally.

A power-down SYNC frame is broadcast over the mesh network to the bait stations 102 by the data collection system 104 in order to synchronize their wake-up. This allows all bait stations 102 and the data collection system 104 to wake-up at the same time in the future (e.g., in 60 minutes) to make sensor readings and to communicate those readings over the mesh to the data collection system 104. The bait stations 102 and data collection systems 104 may wake-up once a minute, once and hour, once a day etc. or any such time chosen, for a synchronization signal. Than fall back to sleep. The bait station 102 and/or data collection system 104 internal clocks can drift. Accordingly, the system may use wake-up checks just to confirm that all the components are on same time. This step of ensuring that all components are on the same time allows for simultaneous data transfer. Data transfer may occur hourly, daily, weekly, monthly or any such time period as so desired etc.

Data collection system 104 operates as "master" node within mesh network. The data collection system 104 queries each bait station 102 one-by-one over the mesh network. All components are awake at the same time. The data collection system 104 communicates with each bait station 102 on its network to avoid collision. This allows each bait station 102 to have full use of the mesh network to expedite transfers and to reduce collisions and contention between bait stations.

As shown in FIG. 15, the data collection system 104 may have a magnetic reed switch 302 and/or an ultrasonic switch 301. An ultra-sonic sensor may power an ultrasonic switch 301 on the data collection system 104 and may be used for the rest/wake-up cycle of the data collection system 104. The ultrasonic switch 301 may allow for the remote wake-up of the data collection system 104 using a remote device. This would allow one to instantaneously download the data stored on the data collection system 104 at that time rather than waiting for the data collection system 104 to send data out per its scheduled download. It is to be understood that the data stored on the data collection system 104 may be the last reported data from the bait stations 102 to the data collection system 104.

It is to be understood that a mobile client such as a phone or hand-held device may perform the following operations: (a) obtain a list of all bait stations 102 connected to the data collection system 104; (b) reset the bait stations and/or data collection system 104; (c) linking the data collection system 104 to the customer's home network (such as WiFi network or cellular network or the like); (d) configure host cloud reporting; (e) check customers home network; (f) delete a bait station 102 from the mesh network; (g) place a bait station 102 and or data collection system 104 into discover mode; and/or (h) erase the entire mesh network.

It is to be understood that an ultrasonic switch 301 may be preferred to other types of switches such as infra-red switches due to its ability to work better in a subsurface environment. The ultrasonic switch 301/device relies on a combination of an ultrasonic transmitter and ultrasonic receiver. The transmitter emits an ultrasonic signal that is transmitted wirelessly to the ultrasonic receiver which then converts the ultrasonic signal into an electronic signal that may be used for various functions. In the case of the pest control and/or detection system 100 that is the subject of the current invention, the ultrasonic switch 301 or device resides within a housing or container 110 that is part of the pest control and/or detection system 100. The data collection system 104 and/or bait station 102 present in the pest control and/or detection system 100 may be placed within a plastic sensor housing (not shown) that is used to form a cavity within the ground. The pest control and/or detection system 100 components may also be placed in the ground without the use of a plastic sensor housing as well. The signal emitted by the ultrasonic transmitter must pass through the covering of the sensor as well as any sensor housing material. Additionally the ultrasonic signal may have to pass through soil, mulch or other materials (i.e., organic or inorganic). It is preferred to use ultrasonic signals versus infrared due to their increased ability to transmit through the subsurface environment as well as the plastic material surrounding the device. The use of the ultrasonic switch 301/device has been tested in the field and has proven to be effective in enabling the activation of the required operational function within the pest control and/or detection system. It is to be understood that the ultrasonic transmitter may be a hand held device of any type that is capable of emitting an ultrasonic signal.

In one embodiment, exemplified in FIGS. 17-22, the pest control and/or detection system 100 can be integrated directly into a connected system or HS Hub 402. It is to be understood that for purposes of this application connected system means any automated or wireless interconnected and/or connected system within a residential and/or commercial structure. A connected system may have a central point of communication or device to gather the communication from all of the devices, such as a HS Hub 402. In addition, it is to be understood that a connected system allows various devices within a residential or commercial structure to communicate with one another or to communicate to a central location. Such devices may include but are not limited to fire/smoke detectors, intrusion detectors, medical alert devices, energy management devices, water/leak detection devices, irrigation systems, smart appliances, lighting features, door locks, window sensors, video/audio devices etc. In addition, it is to be understood that a connected system may communicate externally through the HS Hub 402 and/or a communication portal 404 from the structure 400 to a distributed network system or communication portal 404 or another external source, such as the cloud or single server systems or anything similar etc.

The pest control and/or detection system 100 may be compatible with a residential and/or commercial connected system, and/or distributed network system. The pest control and/or detection system 100 may be directly installed and integrated by service providers into existing and/or as part of a connected system by individuals, including but not limited to, home security providers, builders, pest management professionals, other technology service providers and/or structure owners.

As described previously, the pest control and/or detection system 100 is designed to detect pest activity on a consumable and/or displaceable bait matrix 124. One or more bait stations 102 and at least one data collection system 104 may be installed, in proximity to commercial and/or residential structure spaced at distances determined to be effective in detecting pest activity. Such spacing between the various bait stations 102 and/or data collection systems 104 may be between 5-30 feet, 5-15 feet, and 1-100 feet.

Pest removal of a portion of the conductive bait matrix 123 may trigger a signal that may be communicated from individual bait stations 102 to the one or more data collection systems 104 as described in more detail previously and as shown in FIGS. 13-14. In addition further transmission from the one or more data collection system 104 to a distributed network system for, but not limited to, data management, storage, analysis and/or communication to authorized parties, including but not limited to, the technology provider, installation company, and structure owner. The signal may be transmitted from the data collection system 104 through the HS Hub of the connected system 402 to a communication portal 404 and onward as shown in FIGS. 17-22. The signal indicating pest activity may be further routed by the service provider for the connected system (406, 412) to appropriate recipients (410, 413, 414, 416, 418 etc) including but not limited to the technology owner, an authorized service provider and/or the structure/property owner (400). An authorized service provider (414, 416) may be notified and requested to respond to the potential pest threat.

Utilization of, but not limited to, existing technology, infrastructure, and expertise common to the security and monitoring industries eliminates complexity of the monitoring process, communicates threat and facilitates response to the threat. Integration of the pest control and/or detection system 100 into, including but not limited to, a connected system may provide a similar level of structural protection and peace-of-mind originally offered by the security and monitoring industries, including but not limited to life safety (fire, intrusion, medical) and/or lifestyle (temperature, lights, doors, etc.) management without the need for conventional visual inspection for pest activity. Incorporating pest control with additional home security/monitoring systems provides a broader range of comfort and security to the property owner. It is to be understood when pests are detected by the pest control and/or detection system 100, the alert may go directly to the security company and they may transmit the alert to one or more of the following: a pest control provider; the contact, manager or owner of the structure being monitored; and/or the company providing the pest control and/or detection system.

It is to be understood that communication of the data gathered by the data collection system 104 may occur through a variety of means and may include communication to one or more of the following: a) HS Hub 402 which receives the data from the data collection system 104, b) communication portal 404 which may enable the data transmission from the source (with or without the presence of the HS Hub 402) to the cloud and may comprise a WiFi router, a cell phone or other such devices, c) HS Company Data Service 406, which may host the cloud data which may have been transmitted from the communication portal, d) Home Security Company or other such service provider 410, e) DM Company or Data Management Company 412/413, f) Pest Management Professional "PMP" with or without routing services 414/416 who may take care of any pest detected, g) PM routing service 418 which notifies the PMP, h) Home or property owner 400, i) cloud service network provider 407. FIGS. 17-22 provide examples of various communication pathways. It is to be understood that the pathways may be adjusted and that the general goal of the pest control and/or detection system 100 is to provide data regarding the conductive characteristics of the conductive bait matrix 123 indicative of the presence of pests from the location of the system 100 ultimately to the home owner and/or pest management professional or other such service provider. It is to be understood that various intermediate communication pathways may be used to achieve this purpose.

Another embodiment of this invention is a method to determine, after having deployed traditional or conventional bait at the site, whether the termites (or other insects) that are consuming the bait are the same termites (or other insects) that are infesting the structure on the site. It would be useful, therefore, to provide bait which facilitates making such a determination.

In one embodiment, an insect bait generally comprises a polysaccharide carrier material and a marker material mixed with the carrier material. The marker material is consumable by an insect and contains a substance which facilitates determining, upon viewing the insect, that the insect is actively feeding on the bait.

In another embodiment, a method of controlling insects generally comprises deploying a bait at a first location on a site, wherein the bait contains a marker material which facilitates determining that insects are actively feeding on the bait. The method also comprises monitoring insect activity at the bait, detecting a level of insect activity at the bait as a result of the monitoring, and visually inspecting a second location on the site for insect activity as a result of the detection. The method further comprises determining, by viewing an insect at the second location, that the insect consumed the marker material and is actively feeding on the bait.

Figure 24:
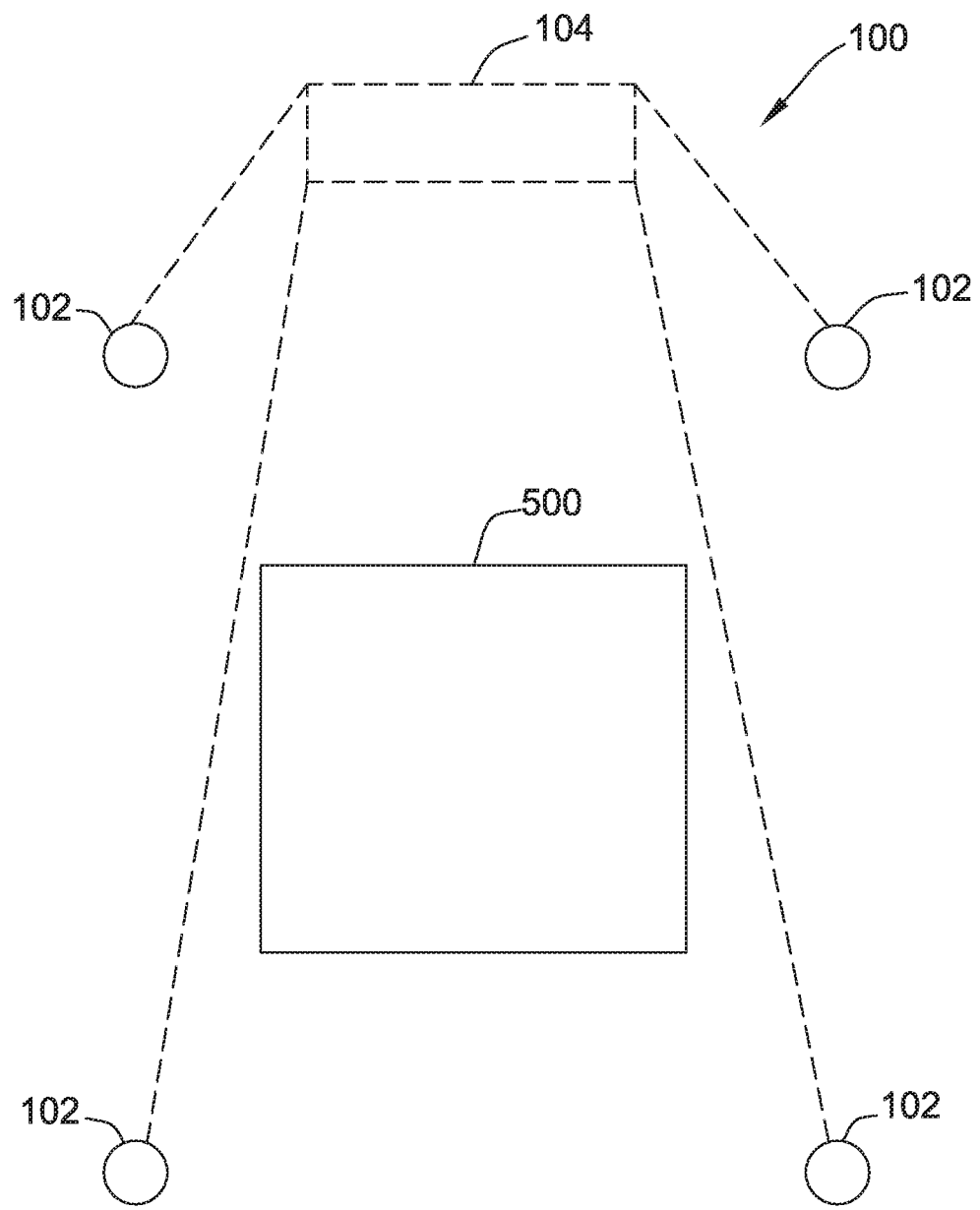
FIG. 24 is a schematic illustration of a pest control and/or detection system having at least one bait station deployed at a site.

Referring now to the drawings, and in particular to FIG. 24, a pest control and/or detection system according to one embodiment is generally indicated by reference numeral 100. The system 100 has at least one bait station 102 deployed at a site for monitoring and/or controlling pest activity (e.g., the perimeter around a home 500). For example, in some embodiments, the bait station 102 is configured for at least monitoring, and in some embodiments controlling, termites. In other contemplated embodiments, however, the system 100 may be configured for monitoring, and in some embodiments controlling, other pests such as, for example and without limitation, cockroaches, ants or other insects, rats, mice, voles or other rodents, birds, bats, etc. In this manner, the bait station(s) 102 may be suitably configured for underground, surface-level, or aboveground deployment as desired.

Figure 25:
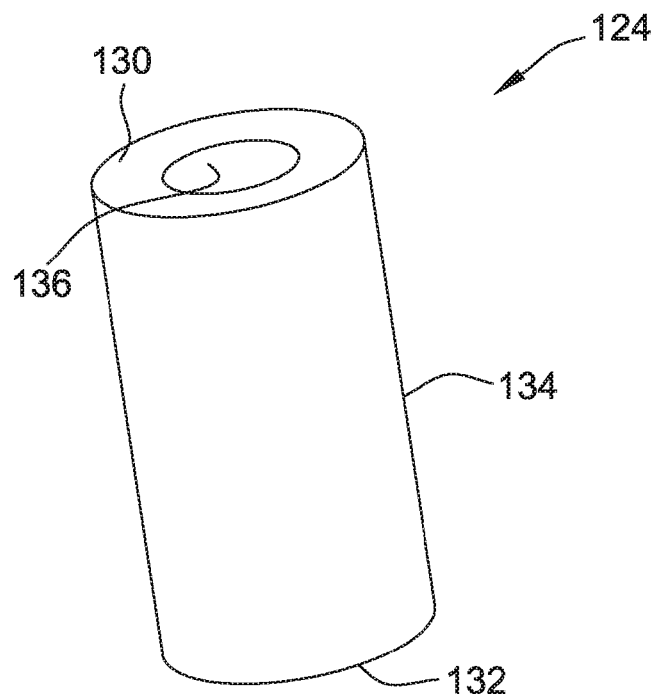
FIG. 25 is a perspective view of an embodiment of bait for use in each of the bait stations of FIG. 24.
Figure 26:
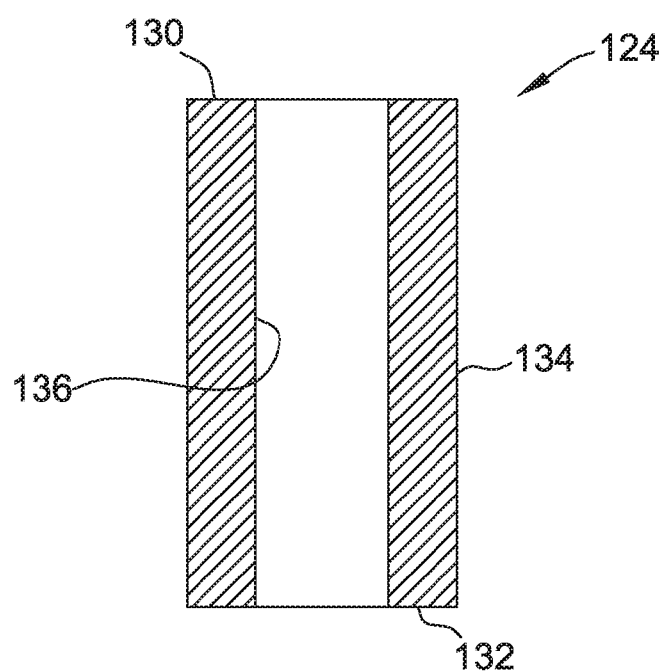
FIG. 26 is a longitudinal cross-section of the bait of FIG. 25.

As shown in FIGS. 25 and 26, each bait station 102 has a bait matrix (indicated generally by the reference numeral 124) configured for consumption by pests, and the bait matrix 124 may have any suitable size and shape. For example, in the illustrated embodiment, the bait matrix 124 is generally tubular (e.g., cylindrical) and has a first end surface 130, a second end surface 132, a circumferential outer surface 134, and a circumferential inner surface 136 defining an internal cavity of the bait matrix 124. The illustrated bait matrix 124 is of an extruded type, and is therefore of a generally solid construction. In other embodiments, however, the bait matrix 124 may instead be fabricated in any suitable manner to be of any suitable consistency (e.g., an overall semi-solid state, such as a gel, or an overall liquid state, such as a fluid suspension).

Figure 27:
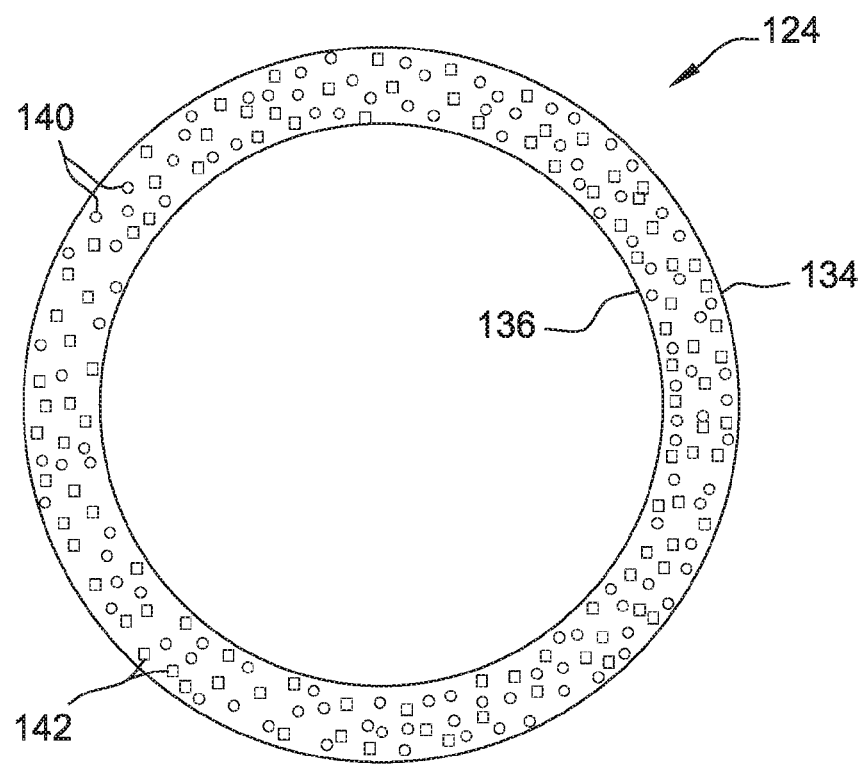
FIG. 27 is a schematic lateral or transverse cross-section of the bait of FIG. 25 prior to consumption.
Figure 28:
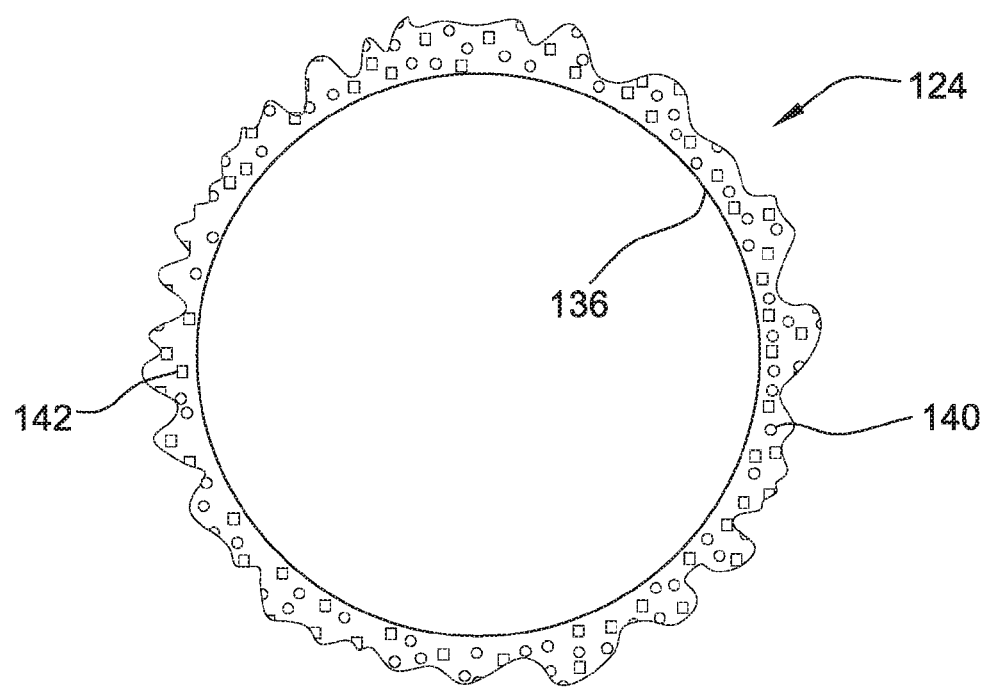
FIG. 28 is a schematic cross-section of the bait of FIG. 27 after portions of the bait have been consumed or otherwise depleted.

Referring now to FIGS. 27 and 28, the bait matrix 124 comprises a marker material (illustrated schematically in particulate form as circles 140) and a carrier material (illustrated schematically in particulate form as squares 142). Notably, while both are illustrated schematically in particulate form, neither the carrier material 142 nor the marker material 140 needs to be in particulate form to be within the scope of this invention.

Referring to FIGS. 27 and 28, the carrier material 142 of the illustrated bait matrix 124 is, at least in part, an consumable material (e.g., a material that is consumable and digestible by a pest being monitored using the bait matrix 124). For example, in one particularly suitable embodiment, the carrier material 142 is a polysaccharide material (e.g., a cellulosic material such as wood flour, wood starch, alpha cellulose, microcrystalline cellulose, or other suitable cellulose material consumable by termites). It is understood that the carrier material 142 may comprise other consumable materials without departing from the scope of this invention. For example, it is also contemplated that the carrier material 142 may comprise a consumable, but non-digestible or essentially non-digestible, material (e.g., a material that is consumable, but not digestible, by a pest being monitored and/or controlled using the bait matrix 124). In one example, a suitable consumable and non-digestible material used as the carrier material 142 may be a resin-type (e.g., thermoplastic) material which is capable of melting and being mixed with the marker material 140 (and a digestible carrier material, if desired) for extrusion together to form the bait matrix 124. In other embodiments, the bait matrix 124 may include a toxicant (e.g., a pesticide active ingredient). Other suitable manufacturing processes are also contemplated for combining the carrier material 142, the marker material 140, and any other desired material(s) to form the bait matrix 124 such as, without limitation, coextrusion, compaction, immersion, molding, suspension and the like.

Referring to FIGS. 27 and 28, the illustrated marker material 140 is a material which is consumable by a pest (e.g., a material which is suitable for termite ingestion) and has a color which renders it visible through the transparent or translucent cuticle, exoskeleton, or shell, and one or more digestive system organ(s), of the pest when the marker material 140 is passing through the digestive system of the pest (e.g., when the marker material 140 is contained in the gut of the pest). In the illustrated embodiment, the marker material 140 is a fat-insoluble material (i.e., the marker material 140 is a material that cannot be stored in the fat of a pest such as, for example, that of a termite). It is also contemplated that, in lieu of or in addition to being fat-insoluble, the marker material 140 may be water-insoluble so as to facilitate ensuring that the marker material 140 does not leave the digestive system of the pest.

In some embodiments, the marker material 140 may be a material that is electrically insulating by nature. In one such embodiment, the marker material 140 may be a polyester-type material (e.g., polyethylene terephthalate (PET), polyethylene (PE), high density polyethylene (HDPE), polypropylene (PP), polycarbonate (PC), polyurethane (PU), etc.) in the form of beads, pellets, or flakes, for example. In another embodiment, the marker material 140 may be a vinyl-type material (e.g., polyvinyl chloride (PVC)) in the form of beads, pellets, or flakes, for example. In yet another embodiment, the marker material 140 may be a plastics-type material (e.g., a wire coating) in the form of beads, pellets, or flakes, for example. In yet another embodiment, the marker material 140 may be a nylon-type (e.g., dark) material in the form of beads, pellets, or flakes, for example. In yet another embodiment, the marker material 140 may be a sand-type material (e.g., lava) in the form of fine or smooth granules, for example. In yet another embodiment, the marker material 140 may be a gravel or shale-type material (e.g., polished gravel or shale) in the form of beads, for example. In yet another embodiment, the marker material 140 may be a glass and/or ceramic-type material (e.g., milled/polished glass and/or ceramic) in the form of beads, for example. In yet another embodiment, the marker material 140 may be a wood-type material (e.g., barbecue/dark wood) in the form of wood fines, for example. Alternatively, the marker material 140 may be a recyclables-type material (e.g., rubber, packaging, etc.) in the form of fine particles, for example.

As is readily seen in FIG. 27, the marker material 140 and the carrier material 142 (e.g., the particles thereof) are randomly interspersed throughout both the thickness and the height of the bait matrix 124 in some embodiments. Moreover, the relative amounts of the marker material 140 vs. the carrier material 142 in the bait matrix 124 may vary in accordance with the desired marking strategy. For example, in some contemplated embodiments, the bait matrix 124 may contain about 0.5% to about 25% (preferably about 12%) by weight of the marker material 140. The remainder of the bait matrix 124 in such embodiments would be the carrier material 142, which could be of both the cellulose-type and the resin-type (e.g., cellulose acetate propionate (CAP), cellulose acetate butyrate (CAB) and/or polybutyrate (PBAT) such as that sold under the trademark Ecoflex®). For example, the carrier material 142 of the resin-type could be about 20-40% by weight of the bait matrix 124. Thus, in some embodiments, if the bait matrix 124 has 90% carrier material 142 by weight, there could be 35% by weight of resin-type and 55% by weight of cellulose-type materials as the carrier material 142. Hence, 10% of the bait matrix 124 by weight would be the marker material 140 in such embodiments. Notably, if the marker material 140 and/or the carrier material 142 are provided in particulate form, it is contemplated that the carrier particles may be sized at about 5-250 microns, and it is contemplated that the marker particles may be sized at about 5 nanometers-250 microns. Other sizes may also be suitable.

When the illustrated embodiment of the bait matrix 124 is deployed, the carrier material 142 in the bait matrix 124 is at least one of palatable, phagostimulant and/or consumable and/or displaceable by pests. As the pests chew on the bait matrix 124, they ingest (or consume) both the carrier material 142 and the marker material 140 of the bait matrix 124, effectively removing material from and decreasing the size of the bait matrix 124 (which is indicative when comparing the unchewed state of the bait matrix 124 shown in FIG. 27, with the chewed state of the bait matrix 124 shown in FIG. 28).

Figure 29:
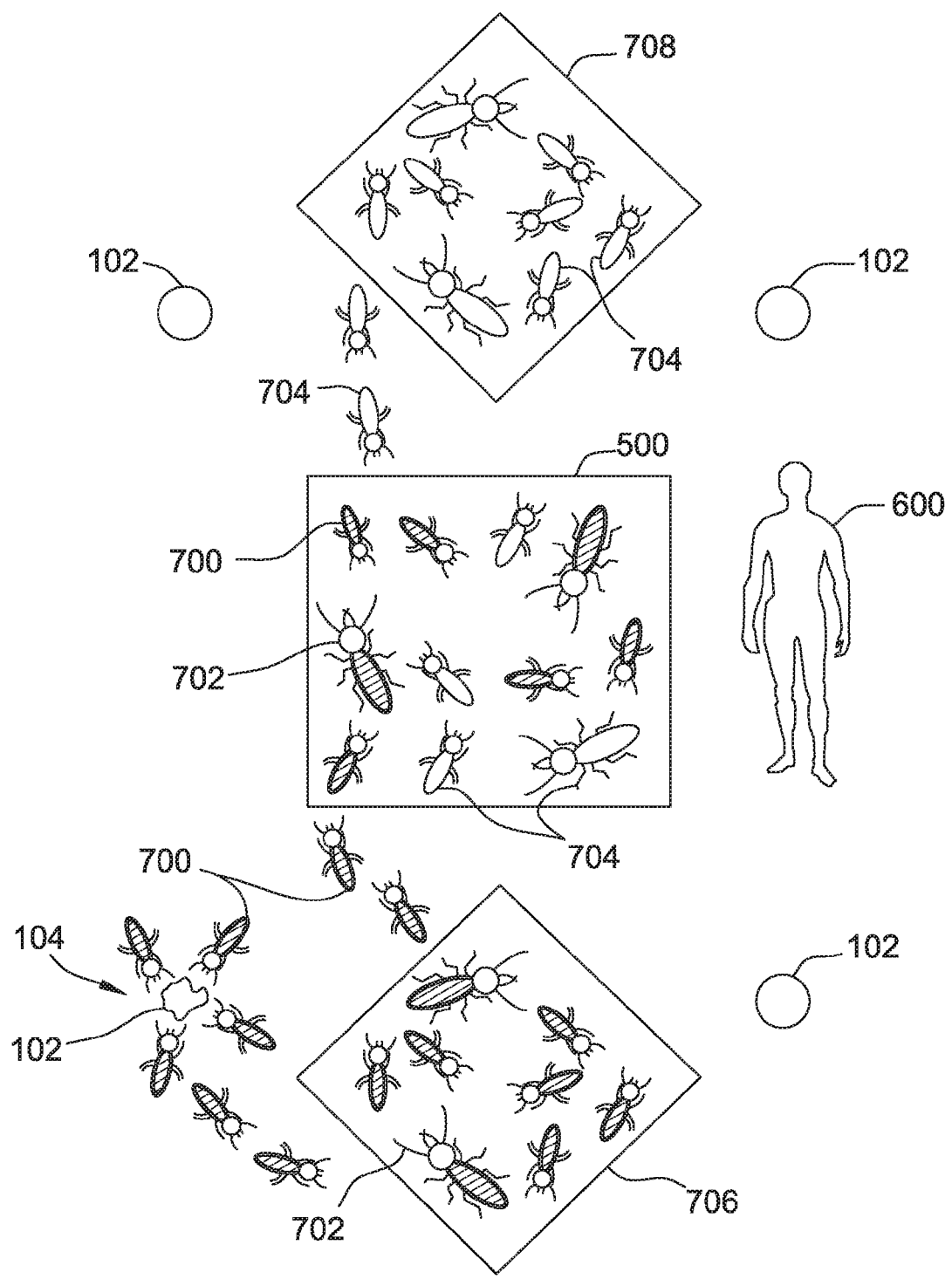
FIG. 29 is a schematic illustration of a technique for inspecting the site shown in FIG. 24 for pest infestation after the pest control and/or detection system of FIG. 24 has been deployed at the site.

As shown in FIG. 29, for example, the pest control and/or detection system 100 can be used by deploying at least one bait station 102 on the site of FIG. 24 (e.g., near the perimeter of the home 500). In the embodiment illustrated in FIG. 29, four bait stations 102 are deployed. However, any suitable number of bait stations 102 may be deployed in other embodiments. Notably, each of the bait stations 102 contains its own bait matrix 124. In this manner, the bait stations 102 can be monitored (e.g., remotely monitored, as set forth in more detail below) for pest activity such that, when a sufficient (e.g., predetermined) level of pest activity has been detected, an inspector 600 may visit the site to physically inspect the site.

In any suitable manner, the inspector 600 (FIG. 29) may note that pests (e.g., termites) are targeting (e.g., consuming the bait matrix 124 of) at least one of the bait stations 102 (a targeted bait station 102 being indicated generally in FIG. 29b by reference numeral 104). Moreover, upon inspection of the home 500 (whether remotely or by being on-site), the inspector 600 may also note that pests (e.g., termites) are infesting the home 500. Under these circumstances, it would have been difficult for the inspector 600 to correlate activity at the targeted base station 104 with activity inside or nearby the home 500 using conventional pest control and/or detection systems (e.g., it would have been difficult for the inspector 600 to know with a higher level of certainty that the pests consuming the bait matrix 124 of the targeted bait station 104 are the same as, or are otherwise associated with, the pests that are infesting the home 500).

Configured in the manner set forth herein, however, the pest control and/or detection system 100 facilitates assisting the inspector 600 in confidently making such a correlation. More specifically, as pests consume the bait matrix 124 of the targeted bait station 104, the pests ingest the marker material 140 (these pests being referred to below as 'marked pests' 700). Because some types of pests (e.g., termites) have a transparent and/or translucent shell and digestive system organ(s), the consumed marker material 140 tends to be visible inside of the marked pests 700 when the inspector 600 views the marked pests 700.

Moreover, because the marker material 140 of the bait matrix 124 is fat-insoluble, the marker material 140 will only be viewable inside of the marked pests 700 when the marker material 140 is passing through the digestive system of the marked pests 700 (i.e., the marker material 140 cannot be stored in the fat of the marked pests 700 for viewing after the marker material 140 has left the digestive system of the marked pests 700).

In this manner, the marker material 140 will only be present inside the digestive system of a marked pest 700 for a limited time (e.g., only a few days). Hence, upon locating marked pests 700 inside or nearby the infested home 500, the inspector 600 can readily determine that the home 500 is infested by pests that are actively feeding on the bait matrix 124 of the targeted bait station 104 (e.g., the inspector 600 can readily identify that the marked pests 700 have consumed the bait matrix 124 of the targeted bait station 104 within the few days preceding the inspection).

As used herein, a pest is said to be 'actively feeding' on the bait matrix 124 if the pest has fed on the bait matrix 124 within the three-day period preceding the occurrence of the pest being viewed by an interested party, such as the inspector 600 (e.g., within 48 hours of the viewing occurrence, or within 24 hours of the viewing occurrence). Such 'active feeding' by a pest is to be distinguished from the type of feeding which is determinable using conventional, fat-soluble dyeing techniques. More specifically, conventional dyeing techniques cannot be used to confidently correlate the fact that a pest has been marked with the fact that the pest has been actively feeding, in that a pest which has consumed conventional dye can remain marked for weeks thereafter (e.g., for up to a month, or 30 days, thereafter). In this manner, when viewing a pest which has been marked as a result of having fed on bait containing conventional dye, for example, it may be equally possible that: (1) the pest consumed the dye just one day prior to viewing; and (2) the pest consumed the dye 25 days prior to viewing. Hence, unlike using the bait matrix 124 to mark a pest, the marking of a pest using conventional dyes is unreliable for making determinations of active feeding as defined herein.

Referring to FIG. 29, upon determining that the home 500 is infested by pests that are actively feeding on the bait matrix 124 of the targeted bait station 104, the inspector 600 can more confidently know, and convey to the owner of the infested home 600, that pests which are infesting the home 500 are also actively and/or continually consuming the bait matrix 124 of the targeted bait station 104 and will soon be controlled and/or eradicated as a result thereof, or as a result of other suitable eradication procedures which will subsequently be taken by the inspector 600. For example, the inspector 600 may replace or supplement the bait matrix 124 of the targeted bait station 104 with a toxicant to be consumed by the pests which are actively feeding at the targeted bait station 104. Generally, an indication of acceptance and consumption of the bait matrix 124 by pests can be confirmed using the marking techniques set forth herein.

Moreover, some species of pests have different castes, at least one of which may be considered a dependent caste because it is for the most part incapable of feeding itself. If the inspector 600, upon inspecting the infested home 500 views, inside or nearby the infested home 500, marked pests 702 that are of a dependent caste, the inspector 600 can determine that the consumed bait matrix 124 is being shared (e.g., by trophallaxis) throughout the broader colony of pests. Upon making such a determination, the inspector 600 can more confidently know, and convey to the owner of the infested home 500, that the colony associated with the marked pests 700 is also actively consuming the bait matrix 124 of the targeted bait station 104 and will soon be controlled and/or eradicated as a result thereof, or as a result of other suitable control and/or eradication procedures to be taken by the inspector 600 in the manner set forth above, for example.

Similarly, upon viewing unmarked pests 704 inside or nearby the infested home 500, the inspector 600 can determine that more than one colony of pests (e.g., more than one colony of termites) may be infesting the home 500. More specifically, the inspector 600 can determine that one such colony of pests (e.g., a first colony 706 of pests) is actively feeding on the bait matrix 124 of the targeted bait station 104, while another such colony of pests (e.g., a second colony 708 of pests) is not actively feeding on the bait matrix 124 of the targeted bait station 104. As a result, the inspector 600 can take a suitable course of action to facilitate locating, and controlling and/or eradicating, the colony of pests that is not actively feeding at the targeted bait station 104.

It is to be understood that this marker material embodiment may be used in combination with the other embodiments disclosed in this application, particularly the conductive bait and pest control and/or detection system embodiment. To facilitate monitoring the bait station(s) 102 using the data collection system 104, the marker material 140 of the bait matrix 124 may in some embodiments be an electrically conductive material. In one contemplated embodiment, the marker material 140 may be a blackish, carbon-based material in particulate form (such as, without limitation, graphite particles, carbon nanotube fragments, carbon black particles, coke particles, or carbonized-charcoal powder). For example, in one particularly suitable embodiment, the marker material 140 may be in the form of graphite particles (e.g., Asbury 4848 graphite particles). In another contemplated embodiment, the marker material 140 may be a colorful metal or alloy of metals in particulate form such as, for example and without limitation, iron, zinc, magnesium, copper, silver, aluminum, or stainless steel particles (e.g., the particles of the marker material 140 may be in a suitable particulate form such as dust, oxide, filings, slag, flakes or otherwise). Alternatively, the marker material 140 may be different than the electrically conductive material, such that the bait matrix 124 is made from the carrier material 142, the marker material 140, and a suitable electrically conductive material (all of which may be in particulate form and extruded or compressed together as a single, monolithic bait matrix structure in some embodiments). Other suitable electrically conductive materials may also be used and remain within the scope of this invention.

EXAMPLES

Termite Preference for Particular Bait Matrix Compounds

Example 1

Termite Preference for Graphite (Conductive Bait Matrix)

Arenas consisted of 100 mm×20 mm polystyrene dishes filled (ca. 5 mm depth) with QuickStone® Laboratory Stone (Whip Mix Corp., Louisville Ky.) mixed as per the manufacturer's instructions. The QuickStone® was cured for 24 hours (h) prior to use. For initial hydration, 5 ml purified water was added to each arena and excess water was poured off after 2 h. The surface was then lightly blotted. Uniformly sized bait sections from two different bait matrix compositions comprising Ecoflex® and graphite or Ecoflex® and no graphite, approximately 1.0×1.0×0.5 cm (10 replicates of each composition), were weighed and placed individually into plastic weigh dishes (4 cm×4 cm, with openings cut into opposite sidewalls for termite access). A non-nutritive 5% agar plug (ca. 0.5 cm×1.0 cm) was added to each arena as a water source. Agar plugs were replaced every 3-4 days (d) and approximately 0.25 ml purified water was added to the surface of each arena every 4 d. About one hundred termites (workers and approximately 10% soldiers, determined by weight) were transferred into each arena. The assay was maintained at 27° C. and 80% RH. After two weeks, bait samples were removed from arenas and oven dried at 110° F. for approximately 24 h. The baits were weighed and the differences in pre and post weights, resulting from bait removal by termites, were compared as an indicator of bait acceptance. Bait removal resulted from a combination of consumption, provisioning (feeding of soldiers by workers), and the application of bait to the surfaces of the arena.

Conclusions

As shown by the data in Table 2, matrix acceptance of Ecoflex® (containing graphite) was significantly greater than that of Ecoflex® (which contained no graphite).

TABLE 2. Comparative consumption data for the "conductive portion of the assembly" ("KA", which includes a mixture of ecoflex®, Lattice® NT 100 (a form of microcrystalline cellulose) and graphite (Asbury® 4848)) and "non-conductive portion of the assembly" ("HW", which includes ecoflex® and Lattice® NT 100 (a form of microcrystalline cellulose)). Acceptance of KA was significantly greater than that of HW in the no choice assay (t test, 0.05% level).

| | Single dish, no choice | | | | | | |
|---|---|---|---|---|---|---|---|
| | KA - ecoflex ® (graphite) | | | | HW - ecoflex ® (no graphite) | | |
| Rep. | pre | post | Δ (g) | Rep. | pre | post | Δ (g) |
| 1 | 0.6313 | 0.5615 | 0.0698 | 1 | 0.8213 | 0.7801 | 0.0412 |
| 2 | 0.6964 | 0.582 | 0.1144 | 2 | 0.8989 | 0.8814 | 0.0175 |
| 3 | 0.7273 | 0.6462 | 0.0811 | 3 | 0.7233 | 0.6849 | 0.0384 |
| 4 | 0.6752 | 0.5329 | 0.1423 | 4 | 0.7364 | 0.688 | 0.0484 |
| 5 | 0.6911 | 0.6017 | 0.0894 | 5 | 0.8481 | 0.8257 | 0.0224 |
| 6 | 0.6775 | 0.6331 | 0.0444 | 6 | 0.6539 | 0.6247 | 0.0292 |
| 7 | 0.6643 | 0.5994 | 0.0649 | 7 | 0.7415 | 0.701 | 0.0405 |
| 8 | 0.6951 | 0.6157 | 0.0794 | 8 | 0.7382 | 0.6934 | 0.0448 |
| 9 | 0.5989 | 0.5058 | 0.0931 | 9 | 0.8413 | 0.7896 | 0.0517 |
| 10 | 0.6214 | 0.5787 | 0.0427 | 10 | 0.6687 | 0.6228 | 0.0459 |
| Avg. → | — | — | 0.08215 | — | — | — | 0.038 |

Example 2

Termite Preference for Ecoflex® Material

Objective

To determine whether Formosan subterranean termites, *Coptotermes formosanus*, and eastern subterranean termites, *Reticulitermes flavipes* had a preference for particular bait matrices components three prototype bait matrices as set forth in Table 3, were presented to the termites via no choice and single-dish choice methodologies.

TABLE 3

Prototype matrices evaluated for acceptance by C. formosanus and R. flavipes

| ecoflex ® | CAB | CAP |
|---|---|---|
| ecoflex ® F Blend X % | CE 24647 (CAB) X % | CE 26627 (CAP) X % |

TABLE 3-continued

Prototype matrices evaluated for acceptance by C. formosanus and R. flavipes

| ecoflex® | CAB | CAP |
|---|---|---|
| NT 100 Y %<br>Graphite Z % | NT 100 Y %<br>Graphite Z % | NT 100 Y %<br>Graphite Z % |

NT 100 = Lattice ® NT 100

Graphite used was Asbury® 4848

Equal percentages (X %) of Ecoflex®, CAB and CAP were used in each respective type of bait sample and combined with the same percentages of NT 100 (Y %) and graphite (Z %) where X, Y and Z each represent a specific percentage of the bait composition and are consistent between the samples, e.g. X % is the same between bait samples (Ecoflex®, CAB and CAP).

No Choice Assay Test:

Arenas consisted of 100 mm×20 mm polystyrene dishes filled (ca. 5 mm depth) with QuickStone® Laboratory Stone (Whip Mix Corp., Louisville Ky.) mixed as per the manufacturer's instructions. The QuickStone® was cured for 24 hours (h) prior to use. For initial hydration, 5 ml purified water was added to each arena and excess water was poured off after 2 h. The surface was then lightly blotted. Uniformly sized bait sections (10 replicates) or pine sections (4 replicates) were weighed and placed individually into plastic weigh dishes (4 cm×4 cm, with openings cut into opposite sidewalls for termite access). A non-nutritive 5% agar plug (ca. 0.5 cm×1.0 cm) was added to each arena as a water source. Agar plugs were replaced every 3-4 days (d) and approximately 0.25 ml purified water was added to the surface of each arena every 4 d. One hundred termites (workers and approximately 10% soldiers, determined by weight) were transferred into each arena. The assay was maintained at 27° C. and 80% relative humidity. After two weeks, bait/pine samples were removed from arenas and oven dried at 110° F. for approximately 24 h. The baits were weighed and the differences in pre and post weights, resulting from bait removal by termites, were compared as an indicator of bait acceptance. Bait removal resulted from a combination of consumption, provisioning (feeding of soldiers by workers), and the application of bait to the surfaces of the arena.

Single-Dish Choice Assay Test:

The single-dish choice replicates (three) were included to determine if termites would accept/consume the bait in the presence of wood. The same method was followed as was described for the no choice assay with the addition to the arena of a section of wood.

Results

General observations: For the duration of the evaluation, termites of both species were observed walking and aggregating on the three prototype baits. After 48 h, bait (marked with graphite) was visible through the body wall in most termites in all arenas as exemplified in FIG. 29. Two weeks after infestation, there appeared to be more bait visible in termites in the Ecoflex® arenas compared to those in the CAB and CAP arenas.

Coptotermes formosanus (Table 4)

No Choice Assay:

Bait acceptance, as indicated by the amount of material removed from the subsample, of ecoflex® was significantly greater than that of CAB, CAP, and pine.

Acceptance of CAP was significantly lower than that of ecoflex®, CAB, and pine.

There was no significant difference between acceptance of CAB and pine.

Single-Dish Choice Assay:

Termites removed more Ecoflex® (59.37 mg) compared to pine (20.97 mg).

Termites removed less CAB (0.83 mg) compared to pine (56.43 mg).

Termites removed less CAP (0.93 mg) compared to pine (41.60 mg).

Reticulitermes flavipes (Table 4)

No Choice Assay:

There were no significant differences in the acceptance of ecoflex®, CAB, and pine.

Acceptance of CAP was significantly lower than that of ecoflex®, CAB, and pine.

Single-Dish Choice Assay:

Termites removed more ecoflex® (66.63 mg) compared to pine (11.03 mg).

Termites removed less CAB (35.37 mg) compared to pine (59.17 mg).

Termites removed less CAP (11.83 mg) compared to pine (74.30 mg).

Conclusions ecoflex® was readily accepted by Formosan subterranean termites, Coptotermes formosanus, and eastern subterranean termites, Reticulitermes flavipes in both no choice and single-dish choice (bait and pine) laboratory methodologies.

Bait acceptance of CAP (containing CE polymer 26627) was significantly lower than ecoflex® and CAB (containing CE polymer 24647) in the no choice assay.

Bait acceptance of CAB and CAP was greatly reduced when paired with a pine food source in a single-dish choice laboratory assay.

Bait acceptance of ecoflex® was greater than that of a pine food source in a single-dish choice laboratory assay.

Table 4. Acceptance[1] of three prototype Trelona™ MY Termite Bait matrices, ecoflex® (thermoplastic material=ecoflex®), CAB (thermoplastic material=CAB), and CAP (thermoplastic material=CAP) by Formosan subterranean termites, Coptotermes formosanus, and eastern subterranean termites, Reticulitermes flavipes

| | | Avg.[3] weight change (mg) 14 d post infestation | |
|---|---|---|---|
| Arena | Treatment[2] | C. formosanus | R. flavipes |
| No choice | KA (Ecoftex ®) | 77.48 A | 64.18 A |
| | KG(CAB) | 42.48B | 55.82 A |
| | HV(CAP) | 16.92C | 21.22 B |
| | Wood (pine) | 44.20 B | 63.73 A |
| Single-dish choice | KA (Ecoftex ®) | 59.37 | 66.63 |
| | Wood (pine) | 20.97 | 11.03 |
| | KG (CAB) | 0.83 | 35.37 |
| | Wood (pine) | 56.43 | 59.17 |
| | HV (CAP) | 0.93 | 11.83 |
| | Wood (pine) | 41.60 | 74.30 |

[1]Acceptance is determined by the change in bait weight resulting from the removal of bait by consumption, provisioning (feeding of soldiers by workers), and the application of bait to the surfaces of the arena.

[2]Table 3 summarizes the general composition.

[3]Average of 10 replicates of no choice ecoflex®, Cab and CAP;

[4]replicates of no choice pine, 3 replicates of single-dish choice.

Values followed by the same letter are not significantly different at the 0.05% level, means separated by Tukey's HSD.

Assay initiated on 1 Sep. 2015, C. Leichter NB 33587 p. 96.

Example 3

Figure 16A:
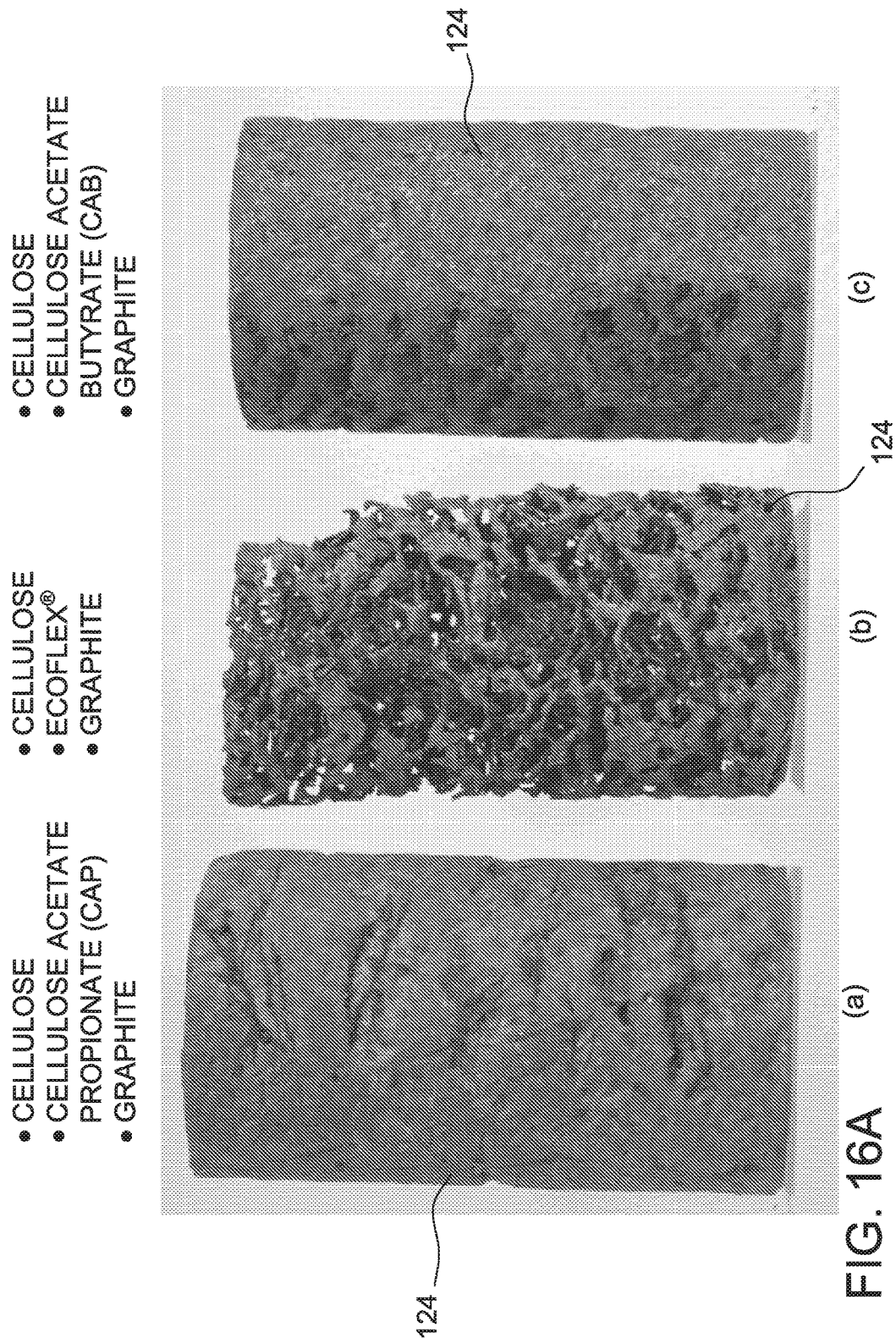
FIG. 16a shows samples of conductive bait matrices 123 after 4 weeks of exposure to *Coptotermes formosanus*.
Figure 17:
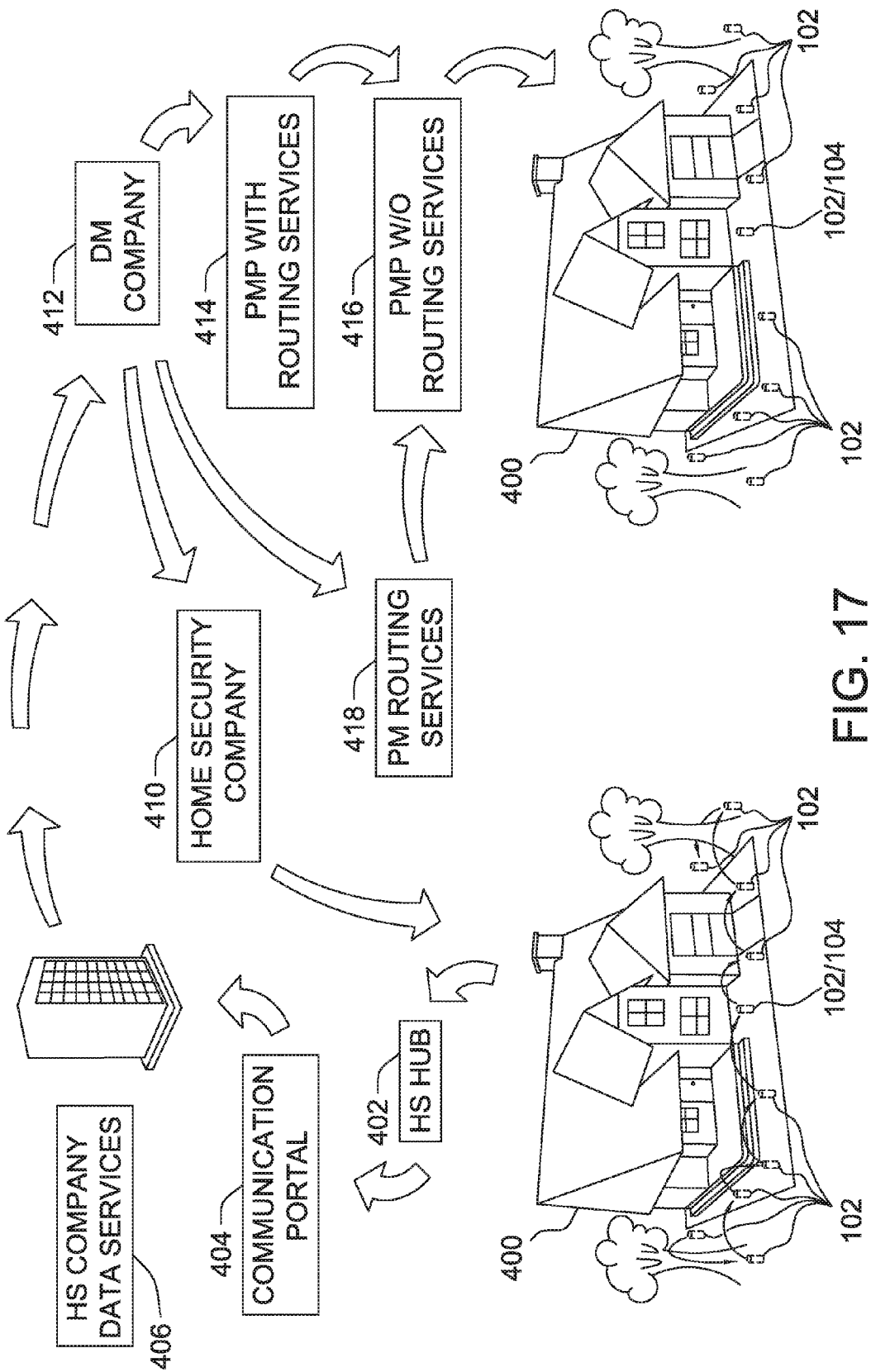
FIG. 17 shows one example of a data communication pathway for the pest control and or detection system 100 when data is hosted on and flow through a Home Security Company's data network to a Data Management Company 412; Station data 102 is received via wireless connection by gateway 104; data is transmitted via WiFi to Home Security Network hub 402; Home Security Network hub 402 communicates via Communication Portal 404 to distributed network servers or cloud hosted by Home Security Company Data Services 406; Pest monitoring/detection data is accessible by Data Management Company 412; after data analytics being performed, pest detection status or alerts are transmitted via Application Programming Interface (API) to Home Security Company 410 and then to Owner of Site 400; pest detection status or alerts are also being sent to Pest Management Routing Services 418 and/or to Pest Management Professional with Routing Services 414; Pest Management Professional w/o (without) Routing Services 416 are making use of data being sent to 418 to decide on measures to be provided to Site 400; Pest Management Professional with Routing Services 414 directly decides on measures to be provided to Site 400 without using Pest Management Routing Services 418.
Figure 18:
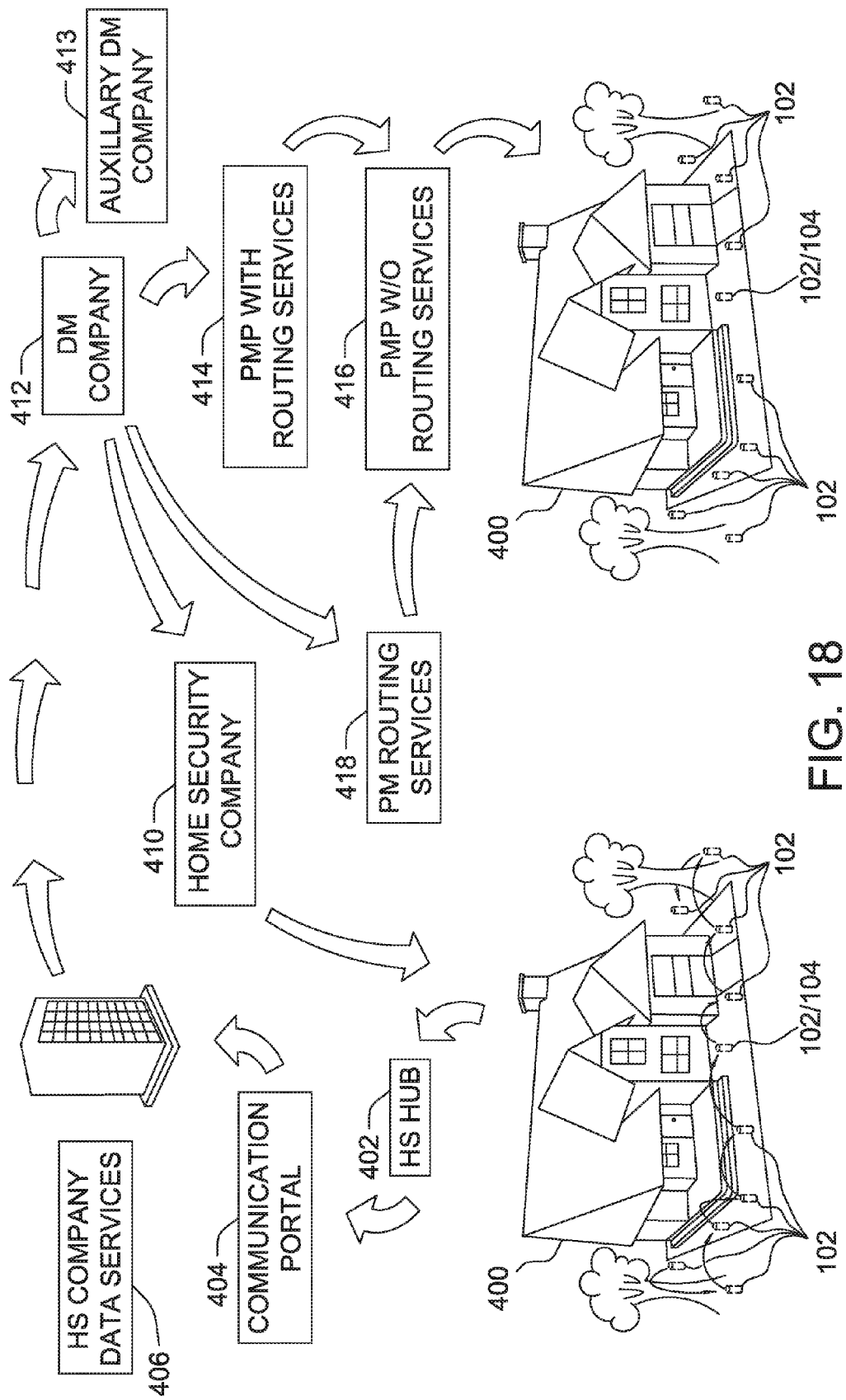
FIG. 18 shows another example of a data communication pathway that differs from the process of FIG. 17 in that an auxiliary data management company 413 also receives Pest monitoring/detection data.
Figure 19:
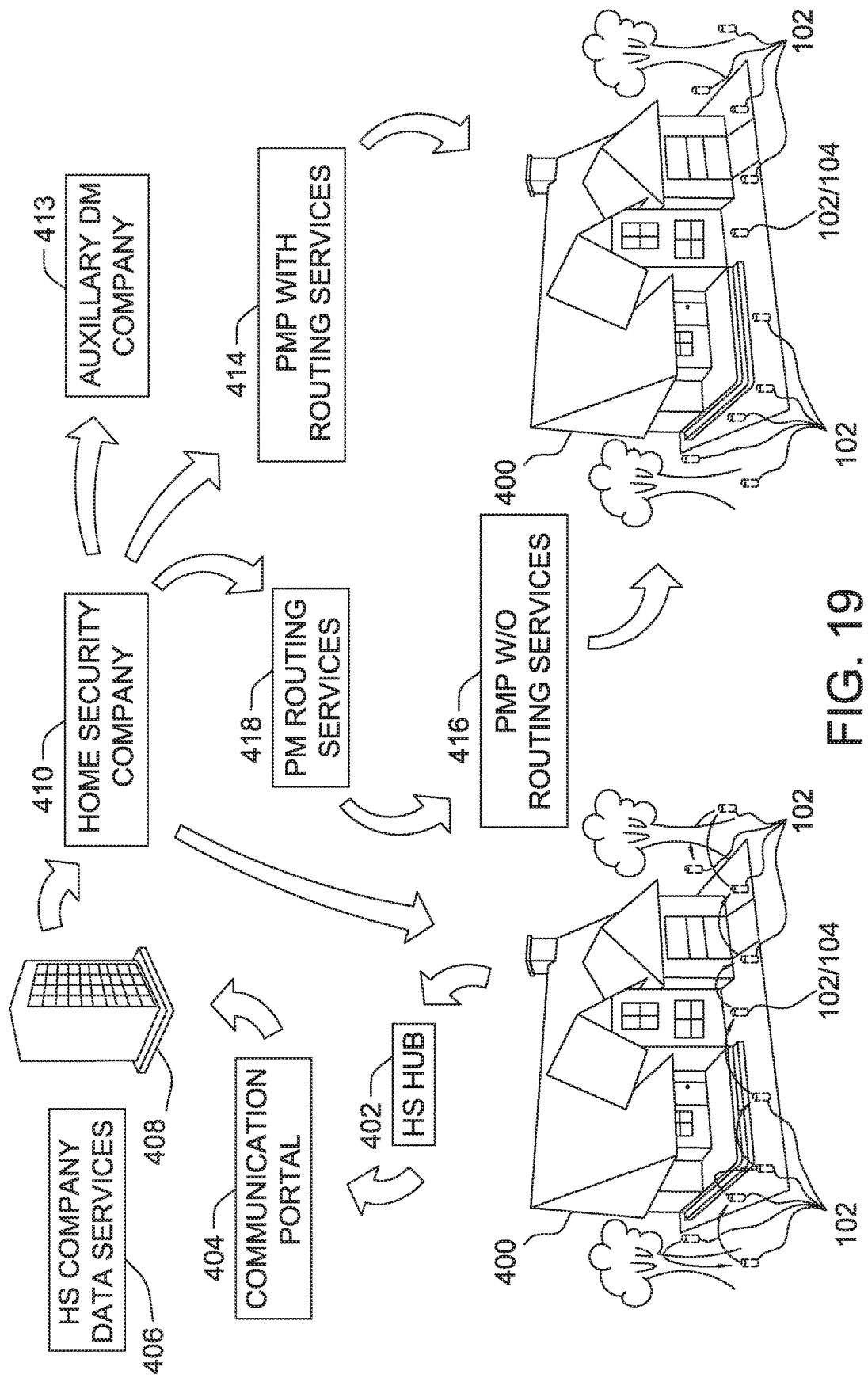
FIG. 19 shows another example of a data communication pathway that differs from the process of FIG. 17 in that the Pest monitoring/detection data is managed by the Home Security Company 410 itself, i.e. without using an additional Data Management Company 412; data may also be forwarded to an auxiliary data management company 413.
Figure 20:
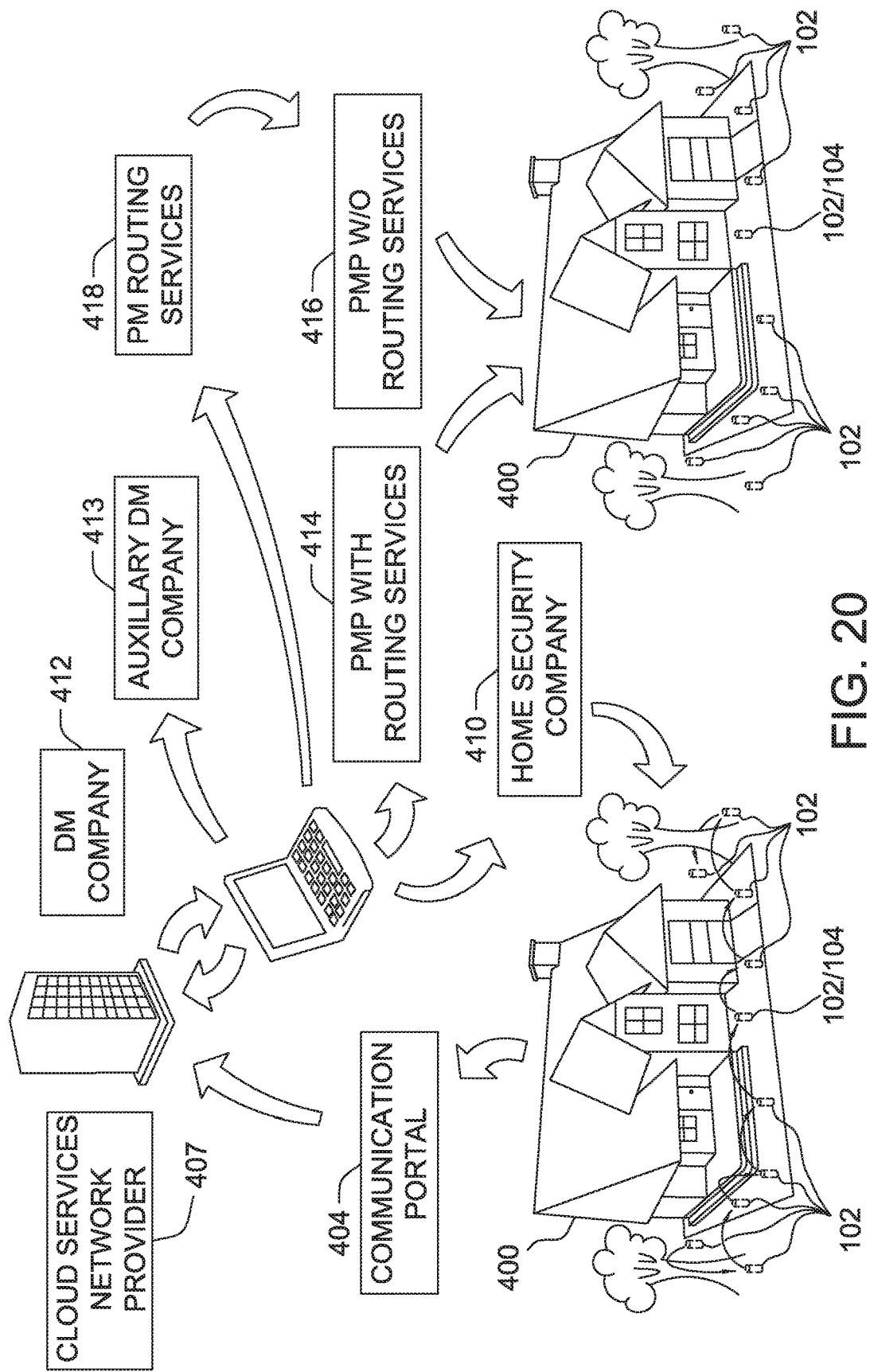
FIG. 20 shows another example of a data communication pathway where Station data 102 is received via wireless connection by gateway 104; data is transmitted via WiFi to Communication 404; 404 may be a WiFi router or a wireless router that acts as a mobile WiFi hotspot (as e.g. MiFi®); data is then forwarded to a distributed network system/cloud which is owned by a Cloud Services Network provider 407; Data Management Company 412 analyzes data located in the distributed network system/cloud; Home Security Company 410 gets involved only after data have been analyzed by Data Management Company 412.
Figure 21:
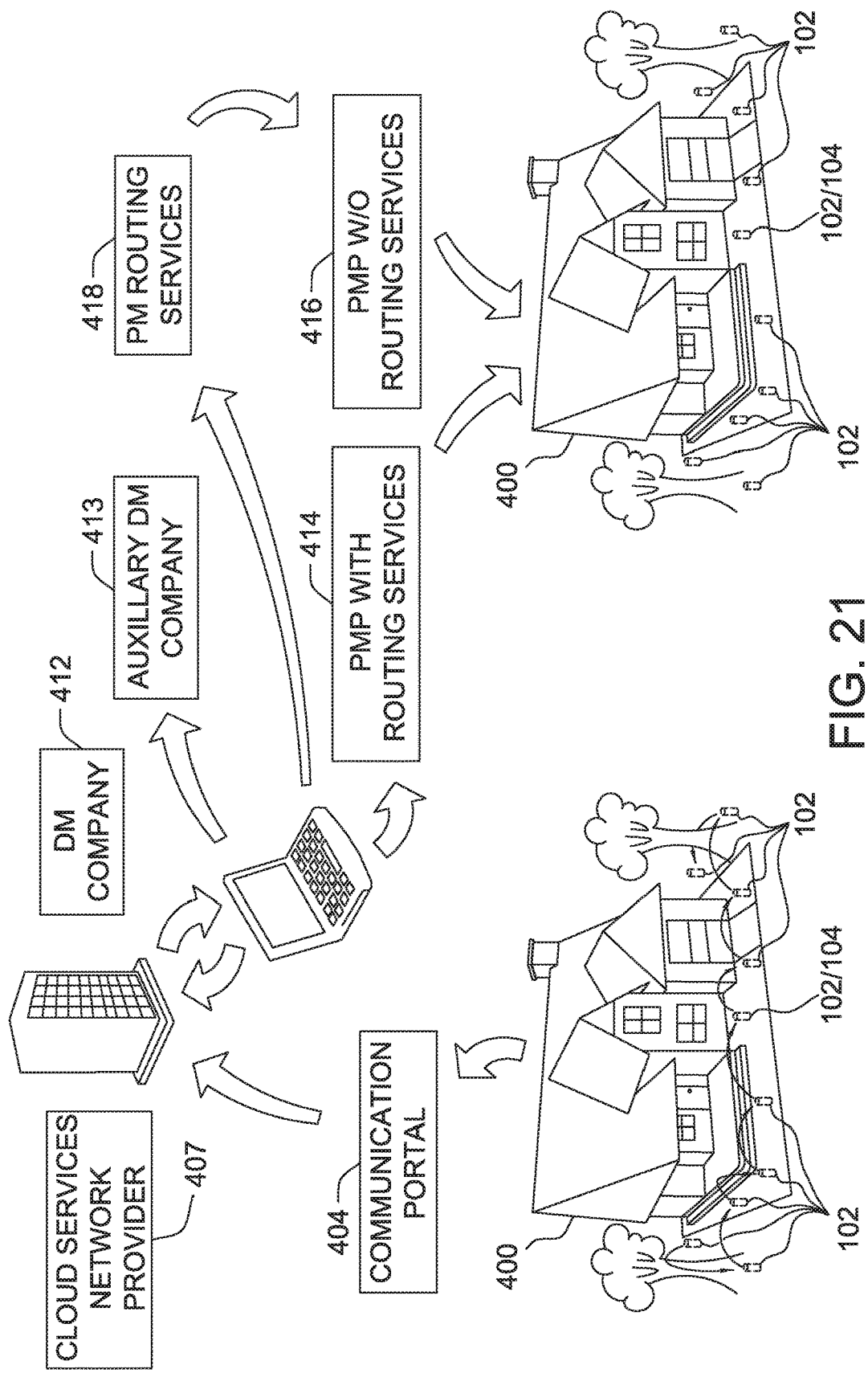
FIG. 21 shows another example of a data communication pathway that differs from process of FIG. 20 in that no Home Security Company 412 would be involved.

Additional preference for an ecoflex® bait matrix is shown in FIGS. 16 and 16a and the data set forth in Table 5 below. FIG. 16 is an example of a bait matrix prior to exposure to the termites. FIG. 16a is an example of the three types of bait matrix compositions following four week of exposure to *Coptotermes formosanus* in a field study. The three baits used were a) a mixture of cellulose (Y%), cellulose acetate propionate CAP (X%), and graphite (Z%), b) a mixture of cellulose (Y%), ecoflex® (X%), and graphite (Z%) and c) a mixture of cellulose (Y%), cellulose acetate butyrate CAB (X%), and graphite (Z %)—where X, Y and Z each represent a specific percentage of the bait composition and are consistent between the samples, e.g. X % is the same between bait a), b) and c). Replicates of the three different baits were placed in buckets in the ground and colonies of termites were allowed to feed on them for a period of thirty days. An estimated number of termites introduced to the buckets was provided at the beginning and an estimated number of termites remaining in the buckets was provided at the completion of the study. Some buckets contained multiple bait matrices as shown in the table below. Other buckets contained individual matrices. Buckets 3-6 were placed near each other surrounding the same location (a tree) and buckets 7-10 were placed near each other surrounding the same location (a second tree). Following the thirty day period, the baits were removed from the buckets and consumption was observed, rated and baits were then weighed.

Conclusion: The termites showed a clear preference for Bait (b)—the ecoflex® blend over the Bait (a)—the CAP blend and Bait (c)—the CAB blend regardless of colony size and whether the baits were presented individually or in combination with one another.

TABLE 5

Preference data from field trial comparing termite preference for (a) CAP blend bait, (b) an ecoflex ® blend bait, and (c) a CAB blend bait after 30 days consumption.
Preference Field Trials

| Bucket # | Treatment | Installation weight (g) | Final Weight (g) | % Bait Consumption | Estimated # Termites at Install/completion |
|---|---|---|---|---|---|
| 1* | Bait (b) | 202.1 | 144.6 | 28.45 | 5000/3,000 |
|  | Bait (b) | 202.0 | 144 | 28.71 |  |
|  | Bait (b) | 200.5 | 126.8 | 36.76 |  |
|  | Bait (b) | 200.6 | 136.1 | 32.15 |  |
|  | Bait (a) | 204.0 | 218 | −6.86 |  |
|  | Bait (a) | 199.9 | 214.8 | −7.45 |  |
|  | Bait (c) | 213.9 | 227.9 | −6.55 |  |
|  | Bait (c) | 209.8 | 222.7 | −6.15 |  |
| 2 | Bait (b) | 200.4 | 18.6 | 90.72 | 15,000/10,000 |
|  | Bait (b) | 200.4 | 17.9 | 91.07 |  |
|  | Bait (b) | 202.8 | 19.1 | 90.58 |  |
|  | Bait (b) | 199.2 | 18.6 | 90.66 |  |
|  | Bait (a) | 202.3 | 218.2 | −7.86 |  |
|  | Bait (a) | 202.6 | 220.6 | −8.88 |  |
|  | Bait (c) | 205.5 | 221 | −7.54 |  |
|  | Bait (c) | 209.5 | 223.2 | −6.54 |  |
| 3 | Bait (b) | 201.0 | 5.6 | 97.21 | 100/200 |
| 4 | Bait (b) | 204.7 | 18 | 91.21 | 200/300 |
| 5 | Bait (a) | 204.1 | 222.3 | −8.92 | 200/0 |
| 6 | Bait (c) | 211.1 | 215.4 | −2.04 | 150/100 |
| 7 | Bait (b) | 200.0 | 14.3 | 92.85 | 100/500 |
| 8 | Bait (b) | 201.3 | 62.2 | 69.10 | 50/400 |
| 9 | Bait (a) | 205.4 | 217.9 | −6.09 | 300/0 |
| 10 | Bait (c) | 208.2 | 217.6 | −4.51 | 50/150 |

*Bucket 1 and its contents were noted to be very wet upon the completion of the study.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A pest control and detection system comprising:
an electrically conductive bait matrix comprising:
at least one carrier material that is at least one of palatable, a phagostimulant, consumable, and displaceable by pests, and a plurality of electrically conductive particles, the electrically conductive particles being substantially randomly interspersed throughout the at least one carrier material, the at least one carrier material comprising at least one of a thermoplastic and a resin-type material.

2. The pest control and detection system of claim 1 where the thermoplastic material is a polyester.

3. The pest control and detection system of claim 1 where the at least one carrier material further comprises a cellulosic material.

4. The pest control and detection system of claim 1 wherein the electrically conductive particles comprise at least one of metallic particles, graphite, carbon nanotube fragments, carbon black, coke and carbonized charcoal powder.

5. The pest control and detection system of claim 1 wherein the at least one of the thermoplastic and the resin-type material comprises about 20 to about 40 percent by weight of the electrically conductive bait matrix.

6. The pest control and detection system of claim 5 wherein the at least one carrier material further comprises a cellulosic material comprising about 20 to about 80 percent by weight of the electrically conductive bait matrix.

\* \* \* \* \*